(12) United States Patent
Clawson et al.

(10) Patent No.: US 11,937,160 B2
(45) Date of Patent: Mar. 19, 2024

(54) SYSTEM AND METHOD FOR EMERGENCY DISPATCH

(71) Applicants: Jeffrey J. Clawson, Millcreek, UT (US); PRIORITY DISPATCH CORPORATION, Salt Lake City, UT (US)

(72) Inventors: Jeffrey J. Clawson, Millcreek, UT (US); Ronald McDaniel, Salt Lake City, UT (US)

( * ) Notice: Subject to any disclaimer, the term of this patent is extended or adjusted under 35 U.S.C. 154(b) by 0 days.

(21) Appl. No.: 17/238,843

(22) Filed: Apr. 23, 2021

(65) Prior Publication Data

US 2022/0345868 A1    Oct. 27, 2022

(51) Int. Cl.
| | |
|---|---|
| *H04W 4/90* | (2018.01) |
| *A61B 5/00* | (2006.01) |
| *A61B 5/01* | (2006.01) |
| *A61B 5/0205* | (2006.01) |
| *A61B 5/024* | (2006.01) |

(Continued)

(52) U.S. Cl.
CPC ............ *H04W 4/90* (2018.02); *A61B 5/0022* (2013.01); *A61B 5/0077* (2013.01); *A61B 5/01* (2013.01); *A61B 5/02055* (2013.01); *A61B 5/024* (2013.01); *A61B 5/0816* (2013.01); *A61B 5/1112* (2013.01); *A61B 5/7275* (2013.01); *A61B 5/747* (2013.01); *G06V 20/40* (2022.01); *G10L 25/51* (2013.01); *H04W 4/14* (2013.01); *A61B 2560/0252* (2013.01); *A61B 2562/0204* (2013.01); *A61B 2562/0219* (2013.01)

(58) Field of Classification Search
CPC .............................. G01S 5/0236; H04W 4/029
See application file for complete search history.

(56) References Cited

U.S. PATENT DOCUMENTS

| | | | |
|---|---|---|---|
| 3,799,147 A | 3/1974 | Adolph et al. | |
| 4,130,881 A | 12/1978 | Haessler et al. | |

(Continued)

FOREIGN PATENT DOCUMENTS

| | | |
|---|---|---|
| CN | 1674685 A | 9/2005 |
| CN | 101169840 A | 4/2008 |

(Continued)

OTHER PUBLICATIONS

U.S. Appl. No. 09/685,697, Non-Final Office Action, dated Apr. 10, 2007, 9 pages.

(Continued)

*Primary Examiner* — Fabricio R Murillo Garcia
(74) *Attorney, Agent, or Firm* — Stoel Rives LLP

(57) ABSTRACT

A computer device generates a response to an emergency being reported by a plurality of sensor devices. The memory contains a sensor data engine and a determinant code calculator. The computer device determines the likelihood of an emergency based on received sensor data and, in some embodiments, answers received from an information provider. The sensor data engine receives external sensor data, determines data values associated with the external sensor data, and calculates an emergency likelihood based on the data values. The determinant code calculator generates a determinant code based on the calculated likelihood, and provides the code to an emergency responder system to generate an emergency dispatch response.

46 Claims, 27 Drawing Sheets

(51) Int. Cl.
*A61B 5/08* (2006.01)
*A61B 5/11* (2006.01)
*G06V 20/40* (2022.01)
*G10L 25/51* (2013.01)
*H04W 4/14* (2009.01)

(56) References Cited

U.S. PATENT DOCUMENTS

| | | |
|---|---|---|
| 4,164,320 A | 8/1979 | Irazoqui et al. |
| 4,237,344 A | 12/1980 | Moore |
| 4,290,114 A | 9/1981 | Sinay |
| 4,338,493 A | 7/1982 | Stenhuis et al. |
| 4,360,345 A | 11/1982 | Hon |
| 4,455,548 A | 6/1984 | Burnett |
| 4,489,387 A | 12/1984 | Amb et al. |
| 4,731,725 A | 3/1988 | Suto et al. |
| 4,839,822 A | 6/1989 | Dormond et al. |
| 4,858,121 A | 8/1989 | Barber et al. |
| 4,865,549 A | 9/1989 | Sonsteby |
| 4,922,514 A | 5/1990 | Bergeron et al. |
| 4,926,495 A | 5/1990 | Comroe et al. |
| 4,945,476 A | 7/1990 | Bodick et al. |
| 4,967,754 A | 11/1990 | Rossi |
| 5,063,522 A | 11/1991 | Winters |
| 5,065,315 A | 11/1991 | Garcia |
| 5,072,383 A | 12/1991 | Brimm et al. |
| 5,077,666 A | 12/1991 | Brimm et al. |
| 5,086,391 A | 2/1992 | Chambers |
| 5,109,399 A | 4/1992 | Thompson |
| 5,122,959 A | 6/1992 | Nathanson et al. |
| 5,193,855 A | 3/1993 | Shamos |
| 5,228,449 A | 7/1993 | Christ et al. |
| 5,253,164 A | 10/1993 | Holloway et al. |
| 5,255,187 A | 10/1993 | Sorensen |
| 5,291,399 A | 3/1994 | Chaco |
| 5,323,444 A | 6/1994 | Ertz et al. |
| 5,339,351 A | 8/1994 | Hoskinson et al. |
| 5,348,008 A | 9/1994 | Bomn et al. |
| 5,379,337 A | 1/1995 | Castillo et al. |
| 5,404,292 A | 4/1995 | Hendrickson |
| 5,410,471 A | 4/1995 | Alyfuku et al. |
| 5,423,061 A | 6/1995 | Fumarolo et al. |
| 5,438,996 A | 8/1995 | Kemper et al. |
| 5,441,047 A | 8/1995 | David |
| 5,462,051 A | 10/1995 | Oka |
| 5,471,382 A | 11/1995 | Tallman et al. |
| 5,502,726 A | 3/1996 | Fischer |
| 5,513,993 A | 5/1996 | Lindley et al. |
| 5,516,702 A | 5/1996 | Senyei et al. |
| 5,521,812 A | 5/1996 | Feder et al. |
| 5,536,084 A | 7/1996 | Curtis et al. |
| 5,544,649 A | 8/1996 | David et al. |
| 5,554,031 A | 9/1996 | Moir et al. |
| 5,590,269 A | 12/1996 | Kruse et al. |
| 5,593,426 A | 1/1997 | Morgan et al. |
| 5,594,638 A | 1/1997 | Iliff |
| 5,594,786 A | 1/1997 | Chaco et al. |
| 5,596,994 A | 1/1997 | Bro |
| 5,630,125 A | 5/1997 | Zellweger |
| 5,636,873 A | 6/1997 | Sonsteby |
| 5,650,995 A | 7/1997 | Kent |
| 5,660,176 A | 8/1997 | Iliff |
| 5,675,372 A | 10/1997 | Aguayo, Jr. et al. |
| 5,682,419 A | 10/1997 | Grube et al. |
| 5,684,860 A | 11/1997 | Milani et al. |
| 5,689,229 A | 11/1997 | Chaco et al. |
| 5,719,918 A | 2/1998 | Serbetciouglu et al. |
| 5,722,418 A | 3/1998 | Bro |
| 5,724,983 A | 3/1998 | Selker et al. |
| 5,734,706 A | 3/1998 | Windsor et al. |
| 5,745,532 A | 4/1998 | Campana, Jr. |
| 5,748,907 A | 5/1998 | Crane |
| 5,754,960 A | 5/1998 | Downs et al. |
| 5,759,044 A | 6/1998 | Redmond |
| 5,761,278 A | 6/1998 | Pickett et al. |
| 5,761,493 A | 6/1998 | Blakeley et al. |
| 5,764,923 A | 6/1998 | Tallman et al. |
| 5,787,429 A | 7/1998 | Nikolin, Jr. et al. |
| 5,805,670 A | 9/1998 | Pons et al. |
| 5,809,493 A | 9/1998 | Ahamed et al. |
| 5,822,544 A | 10/1998 | Chaco et al. |
| 5,823,948 A | 10/1998 | Ross, Jr. et al. |
| 5,826,077 A | 10/1998 | Blakeley et al. |
| 5,832,187 A | 11/1998 | Pedersen et al. |
| 5,842,173 A | 11/1998 | Strum et al. |
| 5,844,817 A | 12/1998 | Lobley et al. |
| 5,850,611 A | 12/1998 | Krebs |
| 5,857,966 A | 1/1999 | Clawson |
| 5,901,214 A | 5/1999 | Shaffer et al. |
| 5,902,234 A | 5/1999 | Webb |
| 5,910,987 A | 6/1999 | Ginter |
| 5,912,818 A | 6/1999 | Mcgrady et al. |
| 5,915,019 A | 6/1999 | Ginter et al. |
| 5,926,526 A | 7/1999 | Rapaport et al. |
| 5,933,780 A | 8/1999 | Connor et al. |
| 5,961,446 A | 10/1999 | Beller et al. |
| 5,962,891 A | 10/1999 | Arai |
| 5,964,700 A | 10/1999 | Tallman et al. |
| 5,986,543 A | 11/1999 | Johnson |
| 5,989,187 A | 11/1999 | Clawson |
| 5,991,730 A | 11/1999 | Lubin et al. |
| 5,991,751 A | 11/1999 | Rivette et al. |
| 6,004,266 A | 12/1999 | Clawson |
| 6,010,451 A | 1/2000 | Clawson |
| 6,022,315 A | 2/2000 | Iliff |
| 6,035,187 A | 3/2000 | Franza |
| 6,040,770 A | 3/2000 | Britton |
| 6,052,574 A | 4/2000 | Smith, Jr. |
| 6,053,864 A | 4/2000 | Clawson |
| 6,058,179 A | 5/2000 | Shaffer et al. |
| 6,074,345 A | 6/2000 | Van Oostrom et al. |
| 6,076,065 A | 6/2000 | Clawson |
| 6,078,894 A | 6/2000 | Clawson et al. |
| 6,084,510 A | 7/2000 | Lemelson et al. |
| 6,106,459 A | 8/2000 | Clawson |
| 6,112,083 A | 8/2000 | Sweet et al. |
| 6,115,646 A | 9/2000 | Fiszman et al. |
| 6,117,073 A | 9/2000 | Jones et al. |
| 6,118,866 A | 9/2000 | Shtivelman |
| 6,127,975 A | 10/2000 | Maloney |
| 6,134,105 A | 10/2000 | Lueker |
| 6,292,542 B1 | 9/2001 | Bilder |
| 6,370,234 B1 | 4/2002 | Kroll |
| 6,535,121 B2 | 3/2003 | Matheny |
| 6,594,634 B1 | 7/2003 | Hampton et al. |
| 6,607,481 B1 | 8/2003 | Clawson |
| 6,610,012 B2 | 8/2003 | Mault |
| 6,696,956 B1 | 2/2004 | Uchida et al. |
| 6,710,711 B2 | 3/2004 | Berry |
| 6,771,163 B2 | 8/2004 | Linnett et al. |
| 6,879,819 B2 | 4/2005 | Brooks |
| 6,901,397 B1 | 5/2005 | Moldenhauer et al. |
| 6,931,112 B1 | 8/2005 | Mcfarland et al. |
| 6,968,375 B1 | 11/2005 | Brown |
| 7,043,262 B2 | 5/2006 | Nageli |
| 7,106,835 B2 | 9/2006 | Saalsaa |
| 7,194,395 B2 | 3/2007 | Genovese |
| 7,289,944 B1 | 10/2007 | Genovese |
| 7,428,301 B1 | 9/2008 | Clawson |
| 7,436,937 B2 | 10/2008 | Clawson |
| 7,438,301 B2 | 10/2008 | Schilling et al. |
| 7,645,234 B2 | 1/2010 | Clawson |
| 7,703,020 B2 | 4/2010 | Bhattaru |
| 7,783,586 B2 | 8/2010 | Friedlander et al. |
| 7,978,826 B2 | 7/2011 | Salafia et al. |
| 8,066,638 B2 | 11/2011 | Clawson |
| 8,081,951 B1 | 12/2011 | Blum |
| 8,103,523 B2 | 1/2012 | Clawson |
| 8,294,570 B2 | 10/2012 | Clawson |
| 8,335,298 B2 | 12/2012 | Clawson |
| 8,346,942 B2 | 1/2013 | Ezerzer et al. |
| 8,355,483 B2 | 1/2013 | Clawson |
| 8,396,191 B2 | 3/2013 | Clawson |
| 8,417,533 B2 | 4/2013 | Clawson |

(56) References Cited

U.S. PATENT DOCUMENTS

| | | |
|---|---|---|
| 8,462,914 B2 | 6/2013 | Ragno et al. |
| 8,488,748 B2 | 7/2013 | Clawson |
| 8,494,868 B2 | 7/2013 | Saalsaa |
| 8,538,374 B1 | 9/2013 | Haimo et al. |
| 8,670,526 B2 | 3/2014 | Clawson |
| 8,712,020 B2 | 4/2014 | Clawson |
| 8,761,719 B1 | 6/2014 | Hines, III et al. |
| 8,873,719 B2 | 10/2014 | Clawson |
| 8,971,501 B2 | 3/2015 | Jeffrey |
| 9,319,859 B2 | 4/2016 | Clawson |
| 9,875,514 B2 | 1/2018 | Smallwood |
| 9,877,171 B2 | 1/2018 | Clawson |
| 2002/0004729 A1 | 1/2002 | Zak et al. |
| 2002/0022492 A1 | 2/2002 | Barak et al. |
| 2002/0106059 A1 | 8/2002 | Kroll et al. |
| 2003/0025602 A1 | 2/2003 | Medema et al. |
| 2003/0028536 A1 | 2/2003 | Singh et al. |
| 2003/0050538 A1 | 3/2003 | Naghavi et al. |
| 2003/0179862 A1 | 9/2003 | Sierra et al. |
| 2003/0187615 A1 | 10/2003 | Epler |
| 2003/0195394 A1 | 10/2003 | Saalsaa |
| 2003/0211856 A1 | 11/2003 | Zilliacus |
| 2003/0212575 A1 | 11/2003 | Saalsaa et al. |
| 2004/0070515 A1 | 4/2004 | Burkley et al. |
| 2004/0219927 A1 | 11/2004 | Sumner |
| 2005/0015115 A1 | 1/2005 | Sullivan et al. |
| 2005/0038696 A1 | 2/2005 | Kalevik et al. |
| 2005/0065813 A1 | 3/2005 | Mishelevich et al. |
| 2006/0031097 A1 | 2/2006 | Lipscher |
| 2006/0038674 A1 | 2/2006 | Sumcad et al. |
| 2006/0059423 A1 | 3/2006 | Lehmann et al. |
| 2006/0122520 A1 | 6/2006 | Banet et al. |
| 2006/0152372 A1 | 7/2006 | Stout |
| 2006/0167346 A1 | 7/2006 | Sarel |
| 2006/0173500 A1 | 8/2006 | Walker et al. |
| 2006/0178908 A1 | 8/2006 | Rappaport |
| 2006/0212315 A1 | 9/2006 | Wiggins |
| 2006/0224357 A1* | 10/2006 | Taware .......... G07C 5/085 702/179 |
| 2006/0225213 A1 | 10/2006 | Tomcany |
| 2007/0055559 A1 | 3/2007 | Clawson |
| 2007/0111702 A1 | 5/2007 | Sanzelius et al. |
| 2007/0112275 A1 | 5/2007 | Cooke et al. |
| 2007/0116189 A1 | 5/2007 | Clawson |
| 2007/0189480 A1 | 8/2007 | Salafia et al. |
| 2007/0201664 A1 | 8/2007 | Salafia et al. |
| 2008/0183493 A1 | 7/2008 | Bogue |
| 2008/0208801 A1 | 8/2008 | Friedlander et al. |
| 2008/0310600 A1 | 12/2008 | Clawson |
| 2009/0005052 A1* | 1/2009 | Abusch-Magder ... H04W 24/02 455/446 |
| 2009/0037374 A1 | 2/2009 | Delia et al. |
| 2009/0067585 A1 | 3/2009 | Clawson |
| 2009/0168975 A1 | 7/2009 | Clawson |
| 2009/0179756 A1 | 7/2009 | Stout |
| 2009/0191529 A1 | 7/2009 | Mozingo et al. |
| 2009/0233631 A1 | 9/2009 | Butler, Sr. et al. |
| 2009/0276489 A1 | 11/2009 | Ragno et al. |
| 2010/0004710 A1 | 1/2010 | Kellum |
| 2010/0088135 A1 | 4/2010 | Nielsen et al. |
| 2010/0121156 A1 | 5/2010 | Yoo |
| 2010/0152800 A1 | 6/2010 | Walker et al. |
| 2010/0198755 A1 | 8/2010 | Soll et al. |
| 2010/0257250 A1 | 10/2010 | Salafia et al. |
| 2010/0260325 A1* | 10/2010 | Clawson .......... G16H 40/20 379/45 |
| 2011/0006600 A1 | 3/2011 | Clawson |
| 2011/0050417 A1 | 3/2011 | Piccioni |
| 2011/0064204 A1 | 3/2011 | Clawson |
| 2011/0066002 A1 | 3/2011 | Clawson |
| 2011/0071880 A1 | 3/2011 | Spector |
| 2011/0099031 A1 | 4/2011 | Nair |
| 2011/0205052 A1 | 8/2011 | Clawson |
| 2011/0215930 A1 | 9/2011 | Lee |
| 2012/0034897 A1 | 2/2012 | Kreitzer et al. |
| 2012/0066345 A1 | 3/2012 | Rayan et al. |
| 2012/0171989 A1 | 7/2012 | Matsuo et al. |
| 2012/0183128 A1 | 7/2012 | Clawson |
| 2012/0207286 A1 | 8/2012 | Clawson |
| 2012/0210271 A1 | 8/2012 | Clawson |
| 2013/0072145 A1 | 3/2013 | Dantu |
| 2013/0100268 A1 | 4/2013 | Mihailidis et al. |
| 2014/0031885 A1 | 1/2014 | Elghazzawi et al. |
| 2014/0064462 A1 | 3/2014 | Clawson |
| 2014/0211927 A1 | 7/2014 | Clawson |
| 2014/0213212 A1 | 7/2014 | Clawson |
| 2014/0243749 A1 | 8/2014 | Edwards et al. |
| 2015/0116126 A1 | 4/2015 | Hyde et al. |
| 2015/0289121 A1 | 10/2015 | Lesage et al. |
| 2015/0289122 A1 | 10/2015 | Friesen |
| 2015/0343229 A1 | 12/2015 | Peterson et al. |
| 2016/0088455 A1 | 3/2016 | Bozik et al. |
| 2016/0148490 A1 | 5/2016 | Barnes et al. |
| 2016/0173689 A1* | 6/2016 | Klaban .......... H04M 7/0075 455/404.1 |
| 2016/0174913 A1* | 6/2016 | Somanath .......... A61B 5/747 600/301 |
| 2016/0196387 A1 | 7/2016 | Whannel et al. |
| 2016/0212605 A1 | 7/2016 | Clawson |
| 2016/0302050 A1 | 10/2016 | Blando et al. |
| 2016/0309026 A1 | 10/2016 | Sterman |
| 2016/0352898 A1 | 12/2016 | Clawson |
| 2017/0028767 A1 | 2/2017 | Tiberius |
| 2017/0124853 A1 | 5/2017 | Mehta et al. |
| 2017/0187878 A1 | 6/2017 | Clawson |
| 2017/0262614 A1 | 9/2017 | Vishnubhatla et al. |
| 2017/0295477 A1 | 10/2017 | Clawson |
| 2018/0053401 A1* | 2/2018 | Martin .......... H04L 67/10 |
| 2018/0174430 A1 | 6/2018 | Sieja |
| 2018/0310159 A1 | 10/2018 | Katz et al. |
| 2019/0313230 A1 | 10/2019 | Macgabann |
| 2019/0318290 A1 | 10/2019 | Clawson et al. |
| 2019/0325726 A1 | 10/2019 | Clawson |
| 2019/0378397 A1 | 12/2019 | Williams, II et al. |
| 2020/0278216 A1 | 9/2020 | Gotschall et al. |

FOREIGN PATENT DOCUMENTS

| | | |
|---|---|---|
| CN | 201117055 Y | 9/2008 |
| CN | 101322392 | 12/2008 |
| CN | 101541234 | 9/2009 |
| CN | 102341799 | 2/2012 |
| CN | 102388599 | 3/2012 |
| CN | 102497484 | 6/2012 |
| CN | 102714524 A | 10/2012 |
| CN | 103330554 | 10/2013 |
| CN | 108293176 B | 11/2020 |
| EP | 2476092 A1 | 3/2011 |
| GB | 2471960 | 1/2011 |
| GB | 2478171 A | 8/2011 |
| GB | 2482741 A | 2/2012 |
| GB | 2489875 A | 10/2012 |
| JP | 2002049693 | 2/2002 |
| JP | 2003109162 A | 4/2003 |
| JP | 2003111735 | 4/2003 |
| JP | 2003187003 A | 7/2003 |
| JP | 2003256963 A | 12/2003 |
| JP | 2010033201 A | 12/2010 |
| KR | 1020050085778 | 8/2005 |
| KR | 1020060084866 | 7/2006 |
| KR | 20070043337 A | 4/2007 |
| KR | 1020080004125 | 1/2008 |
| KR | 1020090014837 A | 2/2009 |
| KR | 100986982 | 10/2010 |
| WO | 2004030259 | 4/2004 |
| WO | 2005039406 A1 | 5/2005 |
| WO | 2006015229 A2 | 2/2006 |
| WO | 2007121237 A2 | 10/2007 |
| WO | 2008014398 A2 | 1/2008 |
| WO | 2008156876 A1 | 12/2008 |
| WO | 2010101580 | 9/2010 |
| WO | 2010120321 A1 | 10/2010 |
| WO | 2011031382 | 3/2011 |
| WO | 2011031383 | 3/2011 |

(56) References Cited

FOREIGN PATENT DOCUMENTS

| WO | 2011106036 | | 9/2011 |
|---|---|---|---|
| WO | 2012100052 | | 7/2012 |
| WO | 2012108897 | | 8/2012 |
| WO | 2012108898 | A1 | 8/2012 |
| WO | 2014039228 | | 3/2014 |
| WO | 2014120428 | | 8/2014 |
| WO | 2014121010 | | 8/2014 |
| WO | 2016109855 | | 7/2016 |
| WO | 2016190962 | | 12/2016 |
| WO | 2017112392 | | 6/2017 |
| WO | 2017176417 | | 10/2017 |
| WO | 2019200019 | A1 | 10/2019 |
| WO | 2019204746 | | 10/2019 |

OTHER PUBLICATIONS

U.S. Appl. No. 09/685,697, Final Office Action, dated Feb. 3, 2004, 5 pages.
U.S. Appl. No. 09/685,697, Non-Final Office Action, dated Jan. 4, 2005, 5 pages.
U.S. Appl. No. 09/685,697, Non-Final Office Action , dated Jul. 18, 2003, 8 pages.
U.S. Appl. No. 09/685,697, Non-Final Office Action, dated Jun. 26, 2006, 8 pages.
U.S. Appl. No. 09/685,697, Advisory Action, dated Mar. 13, 2006, 4 pages.
U.S. Appl. No. 09/685,697, Final Office Action, dated Oct. 4, 2005, 7 pages.
U.S. Appl. No. 09/685,697, Final Office Action, dated Oct. 9, 2007, 11 pages.
U.S. Appl. No. 10/140,635, Non-Final Office Action, dated Apr. 19, 2005, 11 pages.
U.S. Appl. No. 10/140,635, Final Office Action, dated Jan. 17, 2006, 13 pages.
U.S. Appl. No. 10/140,635, Final Office Action, dated Jul. 16, 2004, 11 pages.
U.S. Appl. No. 10/140,635, Final Office Action, dated Jun. 21, 2007, 15 pages.
U.S. Appl. No. 10/140,635, Non-Final Office Action, dated Oct. 3, 2003, 9 pages.
U.S. Appl. No. 10/140,635, Non-Final Office Action, dated Sep. 20, 2006, 15 pages.
U.S. Appl. No. 10/255,901, Non-Final Office Action, dated Jun. 7, 2006, 8 pages.
U.S. Appl. No. 10/255,905, Advisory Action, dated Aug. 11, 2006, 3 pages.
U.S. Appl. No. 10/255,901, Non-Final Office Action, dated Dec. 31, 2003, 8 pages.
U.S. Appl. No. 10/255,901, Advisory Action, dated Feb. 14, 2006, 3 pages.
U.S. Appl. No. 10/255,901, Notice of Allowance, dated Feb. 20, 2013, 9 pages.
U.S. Appl. No. 10/255,901, Final Office Action, dated Feb. 27, 2007, 8 pages.
U.S. Appl. No. 10/255,901, Final Office Action, dated Jun. 29, 2005, 7 pages.
U.S. Appl. No. 10/255,901, Final Office Action , dated Oct. 13, 2004, 8 pages.
U.S. Appl. No. 10/255,901, Non-Final Office Action, dated Sep. 6, 2007, 9 pages.
U.S. Appl. No. 10/255,905, Final Office Action, dated Feb. 9, 2006, 8 pages.
U.S. Appl. No. 10/255,905, Non-Final Office Action, dated Jan. 30, 2007, 7 pages.
U.S. Appl. No. 10/255,905, Notice of Non-Compliant Amendment, dated Jul. 9, 2007, 4 pages.
U.S. Appl. No. 10/255,905, Non-Final Office Action, dated May 19, 2004, 7 pages.
U.S. Appl. No. 10/255,905, Non-Final Office Action, dated May 26, 2005, 5 pages.
U.S. Appl. No. 10/255,905, Final Office Action, dated Oct. 5, 2007, 7 pages.
U.S. Appl. No. 12/268,963, Non-Final Office Action, dated Jul. 29, 2011, 18 pages.
U.S. Appl. No. 12/396,201, Non-Final Office Action, dated Mar. 8, 2011, 23 pages.
U.S. Appl. No. 12/422,561, Notice of Allowance, dated Dec. 9, 2014, 12 pages.
U.S. Appl. No. 12/422,561, Final Office Action, dated Feb. 1, 2013, 26 pages.
U.S. Appl. No. 12/422,561, Non-Final Office Action, dated Jul. 3, 2012, 21 pages.
U.S. Appl. No. 12/558,045, Non-Final Office Action, dated Mar. 22, 2012, 9 pages.
U.S. Appl. No. 12/558,808, Non-Final Office Action, dated Apr. 23, 2012, 9 pages.
U.S. Appl. No. 13/026,043, Notice of Allowance, dated Jan. 13, 2014, 9 pages.
U.S. Appl. No. 13/026,043, Non-Final Office Action, dated Oct. 10, 2013, 27 pages.
U.S. Appl. No. 13/026,055, Notice of Allowance, dated Jan. 24, 2013, 27 pages.
U.S. Appl. No. 13/354,116, Non-Final Office Action, dated Jan. 22, 2013, 9 pages.
U.S. Appl. No. 13/354,116, Notice of Allowance, dated Jun. 7, 2013, 7 pages.
U.S. Appl. No. 13/605,501, Notice of Allowance, dated Mar. 6, 2014, 7 pages.
U.S. Appl. No. 13/605,501, Non-Final Office Action, dated Nov. 18, 2013, 29 pages.
U.S. Appl. No. 13/755,793, Non-Final Office Action, dated Jul. 21, 2014, 17 pages.
U.S. Appl. No. 13/755,793, Notice of Allowance, dated Sep. 22, 2014.
1315206.1, European Examination Report, dated Mar. 20, 2019, 4 pages.
1315206.1, European Examination Report, dated Sep. 30, 2013, 2 pages.
13835875.9, European Examination Report, dated May 15, 2019,6 pages.
U.S. Appl. No. 14/169,302, Notice of Allowance, dated Mar. 4, 2016, 13 pages.
U.S. Appl. No. 14/169,302, Non-Final Office Action, dated Sep. 25, 2015, 46 pages.
U.S. Appl. No. 14/723,947, Non-Final Office Action, dated Mar. 31, 2016, 33 pages.
U.S. Appl. No. 14/723,947, Notice of Allowance, dated Oct. 24, 2016, 29 pages.
U.S. Appl. No. 14/757,797, Non-Final Office Action, dated Aug. 29, 2019, 20 pages.
U.S. Appl. No. 14/757,797, Final Office Action, dated Aug. 30, 2018, 25 pages.
U.S. Appl. No. 14/757,797, Non-Final Office Action, dated Dec. 1, 2017, 13 pgs.
U.S. Appl. No. 14/757,797, Notice of Allowance, dated Mar. 30, 2020, 12 pages.
U.S. Appl. No. 15/083,810, Non-Final Office Action, dated Jul. 15, 2016, 28 pages.
U.S. Appl. No. 15/083,810, Notice of Allowance, dated Sep. 23, 2016, 14 pages.
U.S. Appl. No. 15/094,424, Notice of Allowance, dated Feb. 23, 2018, 5 pages.
U.S. Appl. No. 15/094,424, Non-Final Office Action, dated May 31, 2017, 68 pages.
U.S. Appl. No. 15/094,424, Advisory Action, dated Oct. 16, 2017, 4 pages.
U.S. Appl. No. 15/094,424, Final Office Action , dated Sep. 5, 2017, 35 pages.
U.S. Appl. No. 15/953,297, Final Office Action, dated Apr. 21, 2021, 45 pages.

(56) References Cited

OTHER PUBLICATIONS

U.S. Appl. No. 15/953,297, Non-Final Office Action, dated Aug. 27, 2020, 41 pages.
U.S. Appl. No. 16/389,610, Non-Final Office Action, dated Mar. 2, 2020 , dated Mar. 2, 2020.
16800400.6, Extended European Search Report Issued in European Appl. No. 16800400.6, dated Nov. 15, 2018, 8 pages.
16879853.6, Extended European Search Report, dated May 20, 2019, 8 pages.
17779496.3, Supplementary Extended European Search Report, dated Jun. 21, 2019, 9 pages.
Anonymous, "Suburban Chicago towns centralize 911 services, Communications News", v31 n10 , Oct. 1994 ,2 apges.
Associated Press, "The Simpson Murder Case: Nicole Simpson's 911 Calls", The Los Angeles Times ,Jun. 23, 1994 ,8 pages.
Best,Wendy "999 United Emergency services share life-saving Role to boost response", Western Daily Press, WOP Severnside ed. ,May 27, 1999 ,2 pages.
CBS Web Page News Story,"911 Operator: It's got to be Hell (excerpts from 911 operators' actions during the attacks on Sep. 11, 2001)",, ,Mar. 31, 2006 ,3 pages.
Clark University, "Active Shooter Emergency Plan", ,Jan. 11, 2013, 11 pages.
Crowley,Mark "Learning from CAD System Implementation", Communications, v29 n8 ,Aug. 1992 ,5 pages.
Esch,Trevor "Geac Completes Software Install", Wireless Week, Nov. 18, 1996, 3 pages.
Harris,Roger "Updated 911 Phone System Top Concern of Residents", Business First-Louisville, v9 n19 s1,Dec. 1992 ,3 pages.
Hawai'i Police Department, ,"Proper Use of 911, https://www.hawaiipolice.com/dispatch-911", Feb. 6, 2015 ,1 pages.
Holroyd,Brian Medical Control; Quality Assurance in Prehospital Care, JAMA, the Journal of American Medical Association, v256, n8 ,Aug. 1986 ,pp. 1027-1031.
Jamb Innovations, Llc, uBurn, https://web.archive.org/web/20120506154615/https://itunes.apple.com/us/app/uburn/id327057175?mt=8 ,May 6, 2012 ,2 pages.
Kothari,R. U. "Cincinnati Prehospital Stroke Scale: Reproducibility and Validity", Annals of Emergency Medicine,33/3, https://www.ncbi.nlm.nih.gov/pubmed/10092713 ,Apr. 30, 1999 ,pp. 373-378.
Liferidge,Aisha T.,"Ability of Laypersons to Use the Cincinnati Prehospital Stroke Scale", Prehospital Emergency Care, Elsevier, vol. 8, No. 4 ,Oct. 1, 2004 ,pp. 384-387.
Nor,A. M.,"Agreement Between Ambulance Paramedic- and Physician-Recorded Neurological Signs With Face Arm Speech Test (FAST) in Acute Stroke Patients", http://stroke.ahajournals.org/content/35/6/1355, visited Nov. 17, 2013 ,Apr. 29, 2004 , 3 pages.
Nordberg,Marie,"Dispatch Disasters, Emergency Medicine", Aug. 1995 ,10 pages.
Paho, et al.,"Triage: Prioritizing Care to Reduce Deaths", https://www.paho.org/disasters/index.php?option=com_docman&view=download&category_slug=tools&alias=5 31-pandinflu-leadershipduring-tool-5&Itemid=1179&lang=en ,Nov. 13, 2003 ,7 pages.
PCT/US2008/054987, International Search Report and Written Opinion , dated Oct. 8, 2008 ,11 pages.
PCT/US2009/040909, International Search Report and Written Opinion , dated Jun. 10, 2009 ,10 pages.
PCT/US2009/48577, International Search Report and Written Opinion , dated Aug. 7, 2009 ,9 pages.
PCT/US2010/043308, International Search Report and Written Opinion , dated Jan. 19, 2011 ,9 pages.
PCT/US2010/043311, International Search Report and Written Opinion , dated Jan. 19, 2011 ,3 pages.
PCT/US2010/050402, International Search Report and Written Opinion , dated Apr. 27, 2011 ,9 pages.
PCT/US2011/042543, International Search Report and Written Opinion , dated Feb. 9, 2012 ,11 pages.
PCT/US2011/042582, International Search Report and Written Opinion , dated Feb. 9, 2012 ,8 pages.
PCT/US2012/021867, International Search Report and Written Opinion , dated Aug. 30, 2012 ,8 pages.
PCT/US2013/055537, International Search Report and Written Opinion , dated Nov. 22, 2013 ,10 pages.
PCT/US2014/011405, International Search Report and Written Opinion , dated Apr. 25, 2014 ,10 pages.
PCT/US2014/014029, International Search Report and Written Opinion , dated May 16, 2014 ,12 pages.
PCT/US2016/064719, International Search Report and Written Opinion , dated Feb. 16, 2017 ,16 pages.
PCT/US2017/021519, International Search Report and Written Opinion , dated May 22, 2017 ,17 pages.
PCT/US2019/026855, International Search Report and Written Opinion , dated Jul. 2, 2019 ,9 pages.
PCT/US2019/028347, International Search Report and Written Opinion , dated Jul. 9, 2019 ,11 pages.
Peck, et al., "Got a Minute? You Could Diagnose a Stroke", WebMD Health News, http://www.webmd.com/stroke/news/20030213/got-minute-you-could-diagnose-stroke ,Feb. 13, 2003 ,3 pages.
Poellmitz,William C. et al.,"Wireless technology keeps public safety a step ahead", Nation's Cities Weekly, v21 n17 ,Apr. 27, 1998 ,3 pages.
Qamar,Robert et al.,"Dictaphone introduces Windows-based Computer-Aided Dispatch (CAD) system", Business Wire, (in commercial use in 1995) ,Apr. 23, 1996 ,2 pages.
Radosevich,Lynda et al.,"Network holds sway on life, death", Computerworld, v27 n21 ,May 24, 1993 ,2 pages.
Meyer, Michael J., et al., "Wireless Enhanced 9-1-1 Service—Making It a Reality", Bell Labs Technical Journal, Autumn 1996, pp. 188-202.
U.S. Appl. No. 15/953,297 , Non-Final Office Action, dated Nov. 10, 2021, 56 pages.
Notice of Allowance and Fee(s) Due for U.S. Appl. No. 17/238,892 filed April 23, 2021, and mailed from the USPTO dated October 26, 2023, 11 pages.
International Preliminary Report on Patentability for International PCT Application No. PCT/US2022/071884, dated Oct. 24, 2023, 11 pages.
International Preliminary Report on Patentability for International PCT Application No. PCT/US2022/071885, dated Oct. 24, 2023, 18 pages.

* cited by examiner

─ 680

| Paramount for Emergencies | ⊠ |
|---|---|
| File  View  Spec Logs  Options  Go to Language  Tabs  Version  About ProQA | |

24:41

Location: 123 Cherry Tree Lane, Chicago IL 55555     602

Name/User ID: D.Jones_5487     606

Search Results
```
Daves_VitalWatch  pul/btemp/breath/acc/user  36d4:9630:17bd:2972:849:e4dc:6713:b885  0.0 mi
Sentinel EA-RG7532         Img/vid/mic      3b38:19d3:c4ff:eTle:39f5:eb5e...        0.1 mi
                                                                                       610
```

Sensor Readings
```
Daves_VitalWatch reports:
  o  0 breaths per minute
  o  Sudden drop .76 minutes ago
  o  Pulse at 22 BPM                                                                   612
Sentinel EA-RG7532 reports: Impact Detected
```

Collected Results
```
  o  IMPACT DETECTED
  o  0 breaths per minute
  o  Sudden Drop .76 minutes ago
  o  Pulse at 22 BPM                                                                   616
```

Chief Complaint Likelihood

HIGHLY LIKELY                                                                          618

Determinant Code

A-1                                                                                    620

Personal Information
```
  o  Name:  Daniel Jones
  o  Allergies:  None
  o  Diabetic                                                                          650
```

| O: NAE<br>C: NAE | Person Collapsed | 636 |

| Paramount for Emergencies | ✕ |
|---|---|

File  View  Spec Logs  Options  Go to Language  Tabs  Version  About ProQA

27:05

| Entry | KQ | PDI/CEI | DLS | Summary |
|---|---|---|---|---|

← | Send: 38-D-2 →

Chief Complaint: Person Collapsed    710

KQ Answers
1. The problem category is injuries (TRAUMA).
2. An caller reports an injury to a POSSIBLY DANGEROUS body area.
3. An caller reports he is completely alert (responding appropriately).
4. He is having difficulty breathing.
5. There is no bleeding now.

702

Sensor Data
○ 33 people in area
○ 0 breaths per minute

704

| Determinants | Responses (user-defined) |
|---|---|
| 3 Seizure | |
| 4 STROKE | |
| 5 Serious illness | |
| 6 Unknown status (MEDICAL) | |
| D 0 Override | |
| 1 Reported EXCITED DELIRIUM | |
| 2 HIGH VELOCITY impact | |
| 3 Critical injuries     708 | |
| 4 Multiple victims | |
| 5 Unconscious | |
| 6 Not alert | |
| 7 Difficulty breathing | Delta |

| O: NAE | Person Collapsed |
| C: NAE | |

FIG. 7

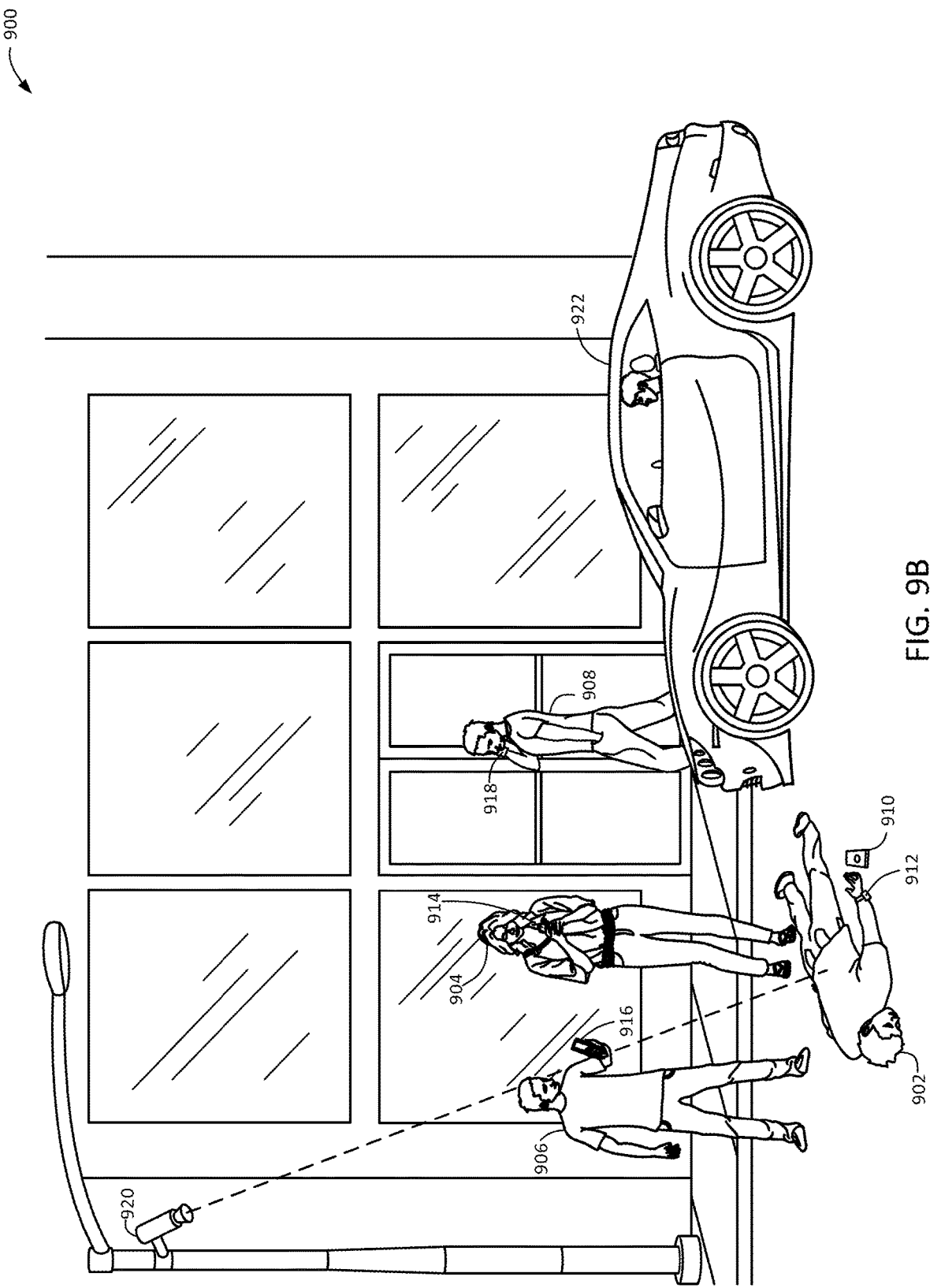

SYSTEM AND METHOD FOR EMERGENCY DISPATCH

COPYRIGHT NOTICE

© 2021 Priority Dispatch Corp. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

The present disclosure relates to computer systems and methods for providing emergency interrogation, information collection, instruction, and dispatch. More specifically, the disclosure is directed to computer-implemented protocols to enable a dispatcher and dispatch system to process emergency response requests in an accurate, consistent, and systematic manner by guiding the dispatcher during interrogation of an information provider in conjunction with the use of relevant external sensor data. In an alternative embodiment, a dispatch system processes emergency responses relying on information collected by sensor-equipped devices.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIGS. 6A-6D illustrate a user interface in accordance with one embodiment.

FIG. 7 illustrates a user interface in accordance with one embodiment.

FIGS. 9A-9B illustrate a scenario in which the systems and methods associated with an emergency response system may be employed.

DETAILED DESCRIPTION

Figure 1:
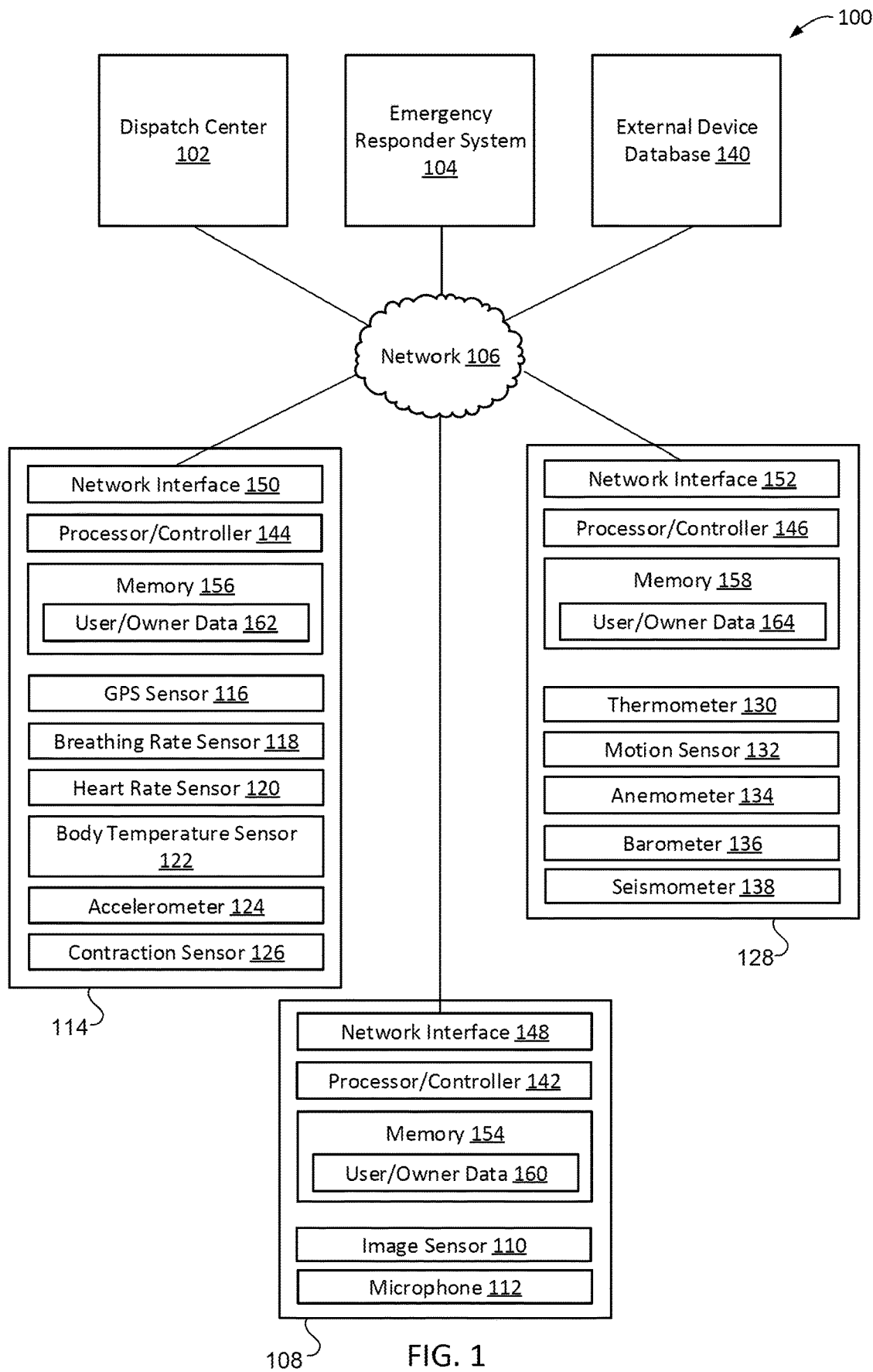
FIG. 1 illustrates an emergency response system in accordance with one embodiment.

Emergency dispatch services that operate dispatch centers may employ dispatchers at the dispatch center(s) to receive reports about emergencies from human information providers that have contacted the dispatch center. Emergency dispatch services greatly benefit from the use of emergency dispatch protocols which standardize the interaction(s) between a dispatcher and an information provider, providing more uniform and consistent results. Emergency dispatch protocols used by dispatchers may include a systematic method of interrogation of information providers with pre-programmed inquiries. This eliminates variability due to different skills of individual dispatchers and eliminates the need for the dispatcher to attempt to recall the appropriate inquiries and instructions each time a call (or other communication) is received. Emergency dispatch protocols allow emergency dispatchers to send (or cause to be sent) appropriate response personnel, emergency vehicles, and/or emergency equipment, etc. to the site of an emergency according to the type of emergency. These protocols may also allow emergency dispatchers to send (or cause to be sent) these personnel, vehicles, equipment, etc., according to a certain priority (which may impact in which order to respond to multiple incidents, whether vehicles sent use lights-and-siren responses, etc.). This allows reasonable use of resources while still appropriately treating each incident with the proper importance (e.g., the protocol may determine that in a given instance a lights-and-siren response is not necessary, reducing the risk of collision). Overall, the use of emergency dispatch protocols improves the accuracy and collection speed of gathered information, and uses that gathered information to appropriately respond to emergencies (e.g., by appropriately dispatching available resources to the most critical emergencies at any given time).

However, an emergency dispatch protocol that considers only the responses of an information provider is limited by the quality and/or quantity of the information that can be gathered from the information provider. This may be problematic in cases where the information provider is in a state of stress (e.g., due to the emergency) and is (at least temporarily) not fully capable of clear thought and communication (or at least, cannot think/communicate as quickly as they normally would when not stressed). It may also be problematic in cases where an information provider is not trained in emergency analysis and/or response and therefore must be instructed about how to analyze a perceived emergency and/or how to respond to an emergency, which takes time. It can also be problematic in cases where the information provider is mistaken or is not being truthful about the nature of a supposed emergency. In these (and other) cases, it may be desirable to augment/supplement the information being provided by the information provider with additional data, if that additional data can be received in time to be used with the emergency dispatch protocol to inform decision-making before dispatching a response. Alternatively, it may be desirable to receive data and provide an emergency dispatch response based on the data and without an information provider.

Modern sensor technology allows for the collection of this relevant additional data in the form of external sensor data. As will be described below, an external device (e.g., a device which is located externally to the dispatch center) including one or more external sensors (e.g., sensors located on or within an external device, or otherwise in communication with the external device) with a known characteristic (a known location, a known association with an information provider or a victim of an incident, etc.) may be able to use its sensors to gather external sensor data related to an incident. The incident may be concurrently reported by an information provider to a dispatcher of the dispatch center. Modern communications network technology further presents an avenue for transporting this external sensor data from the device to the dispatch center in time to be used by the emergency dispatch protocol. Sensor-equipped Internet of Things (IOT) devices (e.g., devices capable of being identified/addressed on a communications network (such as the Internet) and of further communicating their sensor readings to other devices on that communications network) provide the accuracy and utility in gathering external sensor data, which corresponds (in time) to a report of an information provider and may be used when making dispatch decisions. IOT devices may also provide the only input data in determining an emergency response.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures, or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Emergency dispatch protocols disclosed herein may be computer-implemented in whole or in part on a digital computer device (such as, e.g., a digital computer). The computer device may include a processor performing the required computations. The computer device may further include a memory in electronic communication with the processor for storing a computer operating system. The computer operating systems may include MS-DOS, Windows, Unix, AIX, CLIX, QNX, OS/2, and Apple. Alternatively, it is expected that future embodiments will be adapted to execute on other future operating systems. The memory may also store application programs including a computer-aided dispatch (CAD) system, an emergency dispatch protocol, a user interface program, and data storage. The computer device may further include an output device, such as a display unit, for viewing the displayed instructions and inquiries and an input device for inputting response data.

FIG. 1 illustrates an emergency response system 100 in accordance with one embodiment. The emergency response system 100 may include a dispatch center 102, an emergency responder system 104, a network 106, a first external device 108, a second external device 114, a third external device 128, and an external device database 140. While the emergency response system 100 of FIG. 1 has been illustrated using three external devices, it is contemplated that the emergency response system 100 could instead use 1, 2, 4, 10, 2,000, or any other number of external devices. The external devices 108, 114, 128 (or more) provide sensor data so that an emergency can be corroborated from multiple, independent sources.

The dispatch center 102 may be connected via the network 106 to the emergency responder system 104, the first external device 108, the second external device 114, the third external device 128, and the external device database 140. As will be described in further detail below, a computer device of the dispatch center 102 may receive external sensor data from one or more of the first external device 108, the second external device 114, and/or the third external device 128 (and/or other external devices) and determine, using that external sensor data, data values to be used to confirm the likelihood of the type of emergency, emergency priority level, determinant code, and/or chief complaint of an information provider.

The emergency responder system 104 may use any one of various systems, services, application tools or the like to dispatch, track, and/or allocate emergency response resources. In one embodiment, the emergency responder system 104 may provide an interface directly with an emergency response service such as police, firefighters, ambulance services, and the like. As such, dispatch instructions may be sent directly over the network from the dispatch center to any emergency responder system 104. The emergency responder system 104 may include any one of a number of IOT devices capable of interfacing with the network 106. Indeed, an emergency responder may be equipped with a smartphone and a suitable application to enable receipt of dispatch instructions such as the type of emergency, priority level, determinant code, and/or chief complaint.

In one embodiment, the emergency responder system 104 may include a CAD system to manage dispatcher tools for processing emergency calls, including, but not limited to, emergency dispatch protocols (such as the emergency dispatch protocol 210 discussed below), communication resources (e.g., radio system, alpha pager), mapping tools (e.g., global positioning system (GPS) technology, geographic information systems (GIS)), and vehicle location systems (e.g., automatic vehicle location (AVL)). Information used in this task may include location information of both the incident and units, unit availability, and the type of incident. CAD systems may use third-party solutions, such as E-911, vehicle location transponders, and mobile data terminals for automating the location and availability tasks. The emergency response may utilize personnel with appropriate training and a service vehicle with support equipment and medicines on board. The CAD system may match emergency response vehicles and/or trained personnel to the type of emergency that is reported by the dispatch center 102. For example, in emergencies involving injury or other danger to a victim, the victim may be matched by the CAD system with a suitably equipped vehicle and appropriately trained personnel (if the resources are available).

The emergency responder system 104 may receive a determinant code from the dispatch center 102 via the network 106 to generate an emergency response. While the dispatch center 102 and the emergency responder system 104 have been illustrated separately in the embodiment of FIG. 1, it is anticipated that in other embodiments the dispatch center 102 may include the emergency responder system 104.

An external device of the emergency response system 100 may be any data-gathering device located outside of the dispatch center 102. An external device may include components such as controller(s), processor(s), memory, network interface(s), etc. that may allow the respective external device to operate, connect to, control, and/or capture data from each of the one or more external sensors included in that external device. These (and/or further) components may allow each respective external device to connect to, identify on, and/or communicate data across a communications network to and/or from another device. For example, each of the first external device 108, the second external device 114, and/or the third external device 128 may respectively include components (e.g., processors/controllers 142, 144, 146, network interfaces 148, 150, 152 and memories 154, 156, 158) that may allow the respective external device to operate, connect to, control, and/or capture data from each of the one or more external sensors included in that external device and/or connect to, identify on, and/or communicate data across a communications network to and/or from another device of the network 106. Among other things, each of the first external device 108, the second external device 114, and/or the third external device 128 may thereby communicate with the dispatch center 102 via the network 106 in order to send external sensor data to the dispatch center 102.

An external device may include one or more sensors for capturing data and may be capable of transmitting that captured data to the dispatch center 102. For example, as will be described in more detail below, the first external device 108, the second external device 114, and/or the third external device 128 may each include one or more sensors of one or more types.

An external device may (additionally, or alternatively) include user data about a person with which the external device is associated. For example, the first external device 108, the second external device 114, and/or the third external device 128 may each respectively include user data 160, 162, 164 which includes information (e.g., static physiological information) about a user of the first external device 108.

As will be described in more detail below, an external device (e.g., the first external device 108, the second external device 114, and/or the third external device 128) may be capable of identifying itself via the network 106 to other devices (including, e.g., the external device database 140, a computer device of the dispatch center 102, and/or other external devices). This identification may include the communication of a network address of the external device to the other device. This identification may further include the communication of a physical location of the external device to the other device. This identification may further include the communication of the types of sensor(s) present at the external device, the type of data that can be gathered by the sensor(s) present at the external device, the quality of the data that can be gathered by the sensor(s) present at the external device, and/or the format of the sensor data that the external device can provide to the other device via the network. This identification may further include an identification of or other information about a person associated with the external device (e.g., an owner or current user of the external device) as taken from the user data.

It is contemplated that the specific physical form of an external device of the emergency response system 100 may vary greatly. For example, an external device of the emergency response system 100 may include 0, 1, 2, 4, 7, 10, or any other number of sensors. An external device of the emergency response system 100 may be a mobile device (e.g., a cellular telephone or a smartphone), a wearable device (e.g., smart glasses or a smartwatch), or a stationary device (e.g., a security platform, a surveillance camera (which may be part of, or separate from, the security platform), or an environmental platform).

It is contemplated that an external device may communicate with sensors that may be included with the external device in a wide variety of ways. An external device according to the emergency response system 100 may physically integrate all or part of an included sensor into itself. In these cases, it may be that the data output from the included sensor is provided to the external device via a direct physical connection. Alternatively, it is contemplated that an external device according to the emergency response system 100 may include sensors that are physically remote from the external device and which are controlled and/or from which data is received at the external device through a communications network (including the network 106).

It is contemplated that many types of data may be collected by the various sensors of one or more external devices according to an emergency response system 100. For example, the types of data collected may be dynamic physiological data (e.g., a person's heart rate, breathing rate, body temperature), location data, visual data, audio data, and/or weather data (wind speed, barometric pressure, etc.). It is contemplated that these or any other type(s) of data that may be collected by a sensor and that could be related to an emergency may be used with the emergency response system 100.

An external device according to the emergency response system 100 may provide its sensor data to another device (e.g., a computer device of the dispatch center 102, or another external device) via the network. This data may be provided to the other device in any format. For example, an external device may receive raw sensor data from one of its included sensors and may provide that raw data to the other device without changing said raw data. Alternatively, an external device may receive raw data from one of its included sensors and then format the raw data to a shared format type (e.g., a standard format type associated with that type of data) before providing the data to the other device.

An external device according to the emergency response system 100 may provide its sensor data to another device (e.g., a computer device of the dispatch center 102, or another external device) automatically or upon request. For example, it may be that an external device is aware of the other device and has been configured to automatically provide all sensor and/or user data to the other device via a network (e.g., the network 106). Alternatively, it may be that an external device is aware of the other device and has been configured to automatically provide external sensor data from one or more of its external sensors to the other device when abnormal conditions are detected (e.g., sensor readings taken at a certain time, or sensor readings that fall outside of a normal range). Alternatively (or additionally), it may be that an external device is programmed to provide its external sensor data to the other device upon receiving a request (e.g., via the network 106) from the other device. In these cases, it may be that an external device requires authorization credentials from the other device before it will provide its external sensor data. An external device according to the emergency response system 100 may provide any user data to another device in the same manner.

Examples of various types of external sensor data that may be sent from an external device to the dispatch center 102 will now be detailed. While examples of sensors provided in the first external device 108, the second external device 114, and the third external device 128 will be discussed, it is contemplated that many other types of sensors may be useable with the emergency response system 100.

The first external device 108 may include an image sensor 110. The image sensor 110 may be capable of capturing and providing raw video data to the first external device 108. Said raw video data may be optionally formatted and then communicated via the network 106 to the dispatch center 102. The image sensor 110 may be capable of capturing and providing raw still image data to the first external device 108. Said raw still image data may be optionally formatted and then communicated via the network 106 to the dispatch center 102.

The first external device 108 may include a microphone 112. The microphone 112 may be capable of capturing and providing raw audio data to the first external device 108. Said raw audio data may be optionally formatted and then communicated via the network 106 to the dispatch center 102.

The second external device 114 may include a GPS sensor 116. The GPS sensor 116 may be capable of capturing and providing raw location data to the second external device 114. Said raw location data may be optionally formatted and then communicated via the network 106 to the dispatch center 102.

The second external device 114 may include a breathing rate sensor 118. The breathing rate sensor 118 may be capable of capturing and providing raw respiration data to the second external device 114. Said raw respiration data may be optionally formatted and then communicated via the network 106 to the dispatch center 102.

The second external device 114 may include a heart rate sensor 120. The heart rate sensor 120 may be capable of capturing and providing raw heart rate data to the second external device 114. Said raw heart rate data may be optionally formatted and then communicated via the network 106 to the dispatch center 102.

The second external device 114 may include a body temperature sensor 122. The body temperature sensor 122 may be capable of capturing and providing raw body temperature data to the second external device 114. Said raw body temperature data may be optionally formatted and then communicated via the network 106 to the dispatch center 102.

The second external device 114 may include an accelerometer 124. The accelerometer 124 may be capable of capturing and providing raw acceleration data to the second external device 114. Said raw acceleration data may be optionally formatted and then communicated via the network 106 to the dispatch center 102.

The second external device 114 may include a contraction sensor 126. The contraction sensor 126 may be capable of capturing and providing raw contraction data to the second external device 114. Said raw contraction data may be optionally formatted and then communicated via the network 106 to the dispatch center 102. The contraction data captured and provided by the contraction sensor 126 may include the rate of contractions and/or the strength of one or more contractions.

The third external device 128 may include a thermometer 130. The thermometer 130 may be capable of capturing and providing raw temperature data to the third external device 128. Said raw temperature data may be optionally formatted and then communicated via the network 106 to the dispatch center 102.

The third external device 128 may include a motion sensor 132. The motion sensor 132 may be capable of capturing and providing raw motion data to the third external device 128. Said raw motion data may be optionally formatted and then communicated via the network 106 to the dispatch center 102.

The third external device 128 may include an anemometer 134. The anemometer 134 may be capable of capturing and providing raw wind speed data to the third external device 128. Said raw wind speed data may be optionally formatted and then communicated via the network 106 to the dispatch center 102.

The third external device 128 may include a barometer 136. The barometer 136 may be capable of capturing and providing raw barometric pressure data to the third external device 128. Said raw barometric pressure data may be optionally formatted and then communicated via the network 106 to the dispatch center 102.

The third external device 128 may include a seismometer 138. The seismometer 138 may be capable of capturing and providing raw seismic data to the third external device 128. Said raw seismic data may be optionally formatted and then communicated via the network 106 to the dispatch center 102.

The external devices 108, 114, 128 are multiple sources of different and independent sensor data to confirm an emergency situation. Thus, no one external device determines an emergency situation, but rather a compilation of independent sensor data is used for determination. Further, information provider answers may not determine an emergency situation alone. The information provider answers are used in combination with sensor data that is provided independent of the information provider. As will be explained further, the sensor data may be used to determine an emergency type, priority level, determinant code, and/or a chief complaint.

The external device database 140 may include data useful to help the dispatch center 102 locate external devices (e.g., the first external device 108, the second external device 114, and the third external device 128). The external device database 140 may include, for example, information about the geographic location of one or more external devices. This location information may be provided to the external device database 140 upon the addition of the external device to the external device database 140. Further, for external devices that are mobile (smartphones, smartwatches, etc.), the external device itself may provide updates of its location to the external device database 140 from time to time.

The external device database 140 may include information about an association between a person and an external device (e.g., a username of a person associated with a device). The external device database 140 may also include information about a unique external device identifier (see below) associated with each of one or more external devices. The external device database 140 may also include information about the type(s), format(s), and/or quality(ies) of external sensor data that may be provided by the external device.

An external device (and its related information as described) may be added to the external device database 140 manually by an operator of the external device database 140. It is further contemplated that in other embodiments, an external device will add itself, along with its related information, to the external device database 140 automatically by communicating with the external device database 140 via the network 106 and/or periodically update its information (e.g., location information, as described above) in the external device database 140 automatically by communicating with the external device database 140 via the network 106.

Figure 2:
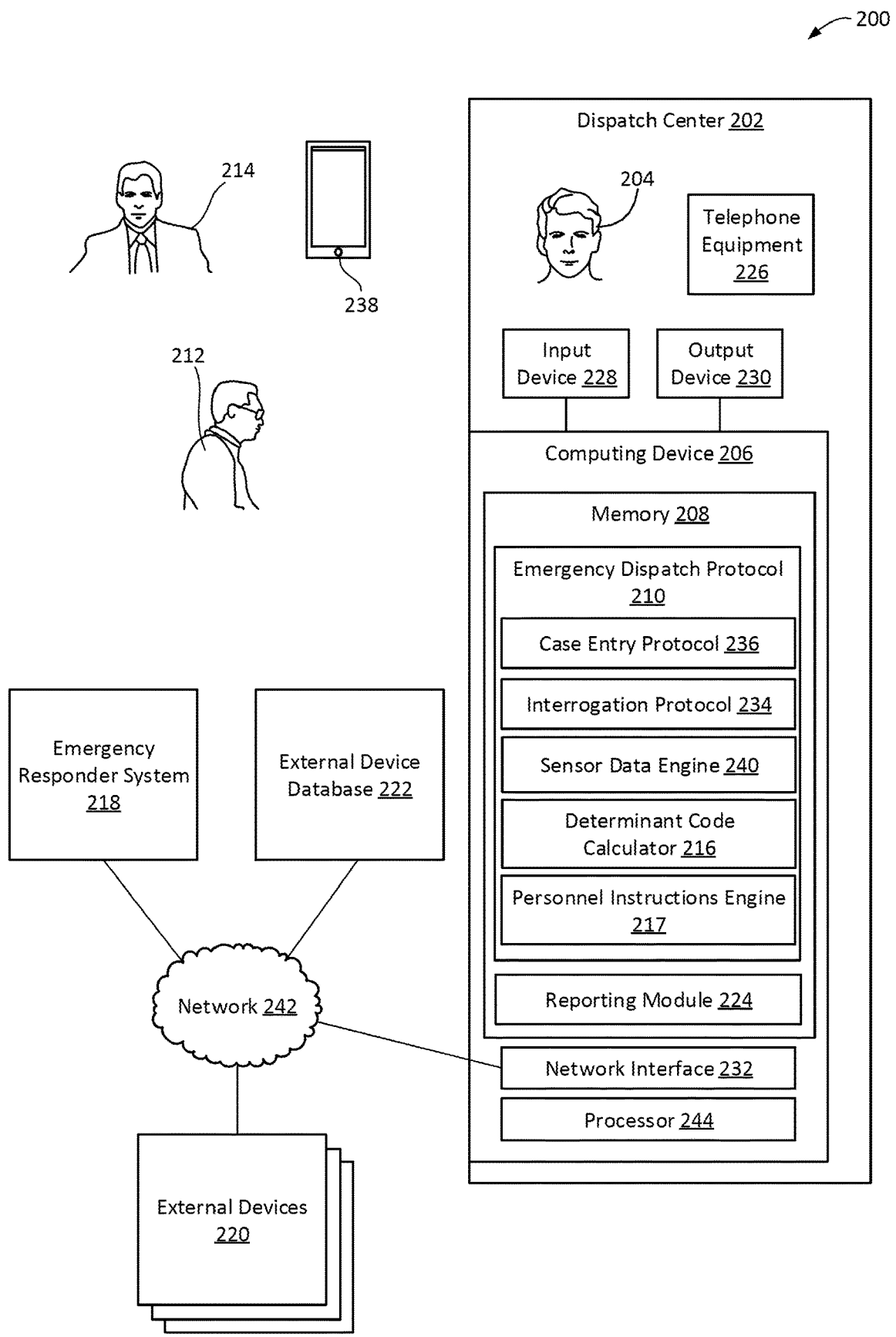
FIG. 2 illustrates an emergency response system in accordance with one embodiment.

FIG. 2 illustrates an emergency response system 200 in accordance with one embodiment. The emergency response system 200 includes a dispatch center 202. At the dispatch center 202, a dispatcher 204 operates a computer device 206 having a processor 244, a memory 208, and a network interface 232. The memory 208 may be provided with an emergency dispatch protocol 210 at least partially stored thereon to enable the dispatcher 204 to rapidly and consistently perform their duties in dispatching an emergency response. In identifying the emergency, the dispatcher 204 asks a series of questions; while some questions are intuitive, some protocol questions may be missed if the dispatcher 204 is not guided. The emergency dispatch protocol 210 accordingly provides instructions that are expertly drafted to assist a (potentially) untrained information provider 214 in determining pertinent needs and conditions to thereby allow for a suitable emergency response. The emergency dispatch protocol 210 may also provide expertly drafted first aid instructions to assist the information provider 214 prior to the arrival of emergency responders.

The dispatch center 202 further includes telephone equipment 226, an input device 228, and an output device 230 to respond to calls and interface with the computer device 206. The dispatcher 204 receives calls on the telephone equipment 226, identifies a call as requiring an emergency response and initiates the emergency dispatch protocol 210. A communication coming into the dispatch center 202 may be a verbal report from, for example, an emergency line (e.g., through the use of the phone 238). A verbal report may alternatively be received in another way, for example, by an administration line or through radio. In other cases, the emergency dispatch protocol 210 may be initiated when the computer device 206 receives information (other than a verbal report) from an information provider 214, such as a text message. In some cases, the information provider 214 may report the acute effects of the emergency on one or more victims, such as the victim 212. In some instances, the victim 212 may call or send information on their own behalf (in which case the victim 212 may be said to also be acting as the information provider 214). In other cases, an information provider 214 may communicate with the dispatch center 202 regarding an emergency that does not involve an acute effect on a victim 212 (e.g., an emergency affecting only the safety of property).

The emergency dispatch protocol 210 provides a logic tree with questions, possible responses from the information provider 214, possible data values gathered by the sensor data engine 240, and possible instructions to the information provider 214. The questions of the emergency dispatch protocol 210 may be asked by the dispatcher 204 to the information provider 214. This process may be verbal (e.g., via the telephone equipment 226), or it may be nonverbal (e.g., via text message). The information provider 214 responses in some cases lead to subsequent questions and/or instructions to the information provider 214. The responses and data values are processed according to pre-determined logic to determine a determinant code to provide an emergency response. During the emergency dispatch protocol 210, the dispatcher 204 and/or the emergency dispatch protocol 210 will gather, inter alia, conditions and circumstances of the emergency that are as presented, as discovered through interrogation, and/or as reflected in data values determined from external sensor data in order to dispatch an appropriate emergency response. The emergency dispatch protocol 210 facilitates uniform and consistent gathering of information relating to the emergency. The dispatch of an appropriate emergency response may be determined, in part, through a system of logically assigning determinant codes as the protocol progresses (i.e., traverses) through the logic tree. The logic tree of the emergency dispatch protocol 210 may be provided across multiple sub-components of the emergency dispatch protocol 210, including, but not limited to, a case entry protocol 236, an interrogation protocol 234, a sensor data engine 240, a determinant code calculator 216, and/or a personnel instructions engine 217.

Exemplary embodiments of dispatch protocols with logic trees are disclosed in U.S. Pat. Nos. 5,857,966, 5,989,187, 6,004,266, 6,010,451, 6,053,864, 6,076,065, 6,078,894, 6,106,459, 6,607,481, 7,106,835, 7,645,234, 8,066,638, 8,103,523, 8,294,570, 8,335,298, 8,355,483, 8,396,191, 8,488,748, 8,670,526, 8,712,020, 8,873,719, 8,971,501, 9,319,859, 9,491,605, and 9,516,166, which are incorporated herein by reference.

The emergency dispatch protocol 210 decision points deal directly with life-and-death decisions, and, accordingly, the protocols and/or engines discussed herein pass a rigorous review by experts in the relevant emergency response fields of medical, police and/or fire dispatch.

The computer device 206 may include the case entry protocol 236 which may act to collect initial information that is relevant to many types of emergencies to which the dispatch center 202 may need to respond. The case entry protocol 236 may be useful to aid the dispatcher 204 and/or the computer device 206 in determining the type of emergency, priority level, determinant code, and/or chief complaint of the information provider 214. An embodiment of the case entry protocol 236 given in terms of its corresponding graphical user interface (GUI) is discussed in more detail in FIG. 3 below.

The computer device 206 may further include an interrogation protocol 234. The interrogation protocol 234 may include pre-programmed inquiries that the dispatcher 204 may ask the information provider 214 in order to receive relevant information about a perceived emergency. The interrogation protocol 234 may be one of many possible interrogation protocols, and may be selected based on its relation to the type of emergency or a chief complaint of the information provider 214. An embodiment of the interrogation protocol 234 given in terms of its corresponding GUI is discussed in more detail in FIGS. 4A-4E below.

The computer device 206 may further include a sensor data engine 240. The sensor data engine 240 may be used by the emergency dispatch protocol 210 to communicate with and receive external sensor data from the one or more external devices 220. Examples of some external devices have been previously given as external devices 108, 114, and 128. This external sensor data may be used by the emergency dispatch protocol 210 for corroboration to improve the accuracy and/or speed of a dispatch decision. The external sensor data originates from separate and independent external devices to confirm an emergency. Furthermore, the external sensor data may include data from different types of sensors to capture different types of data such as audio, video, thermal, physiological, speed, and the like. An embodiment of the interrogation protocol 234 given in terms of its corresponding GUI is discussed in more detail in FIGS. 5A-5D below.

The emergency dispatch protocol 210 includes and operates a determinant code calculator 216 to calculate a determinant code from the answers of the information provider 214 to pre-programmed inquiries and input from the sensor data engine 240. As described further herein, the sensor data engine 240 communicates with the determinant code calculator 216 to augment and corroborate the answers from the information provider 214. The determinant code calculator 216 may also determine the likelihood that the type of emergency or the chief complaint of the information provider 214 is accurate. The determinant code calculator 216 may calculate a determinant code that indicates a priority of a response that should be dispatched. The determinant code calculator 216 may calculate a determinant code that indicates the type of the emergency. The determinant code calculator 216 may calculate a determinant code that indicates a priority of a response that should be dispatched and the type of the emergency. As the determinant code may indicate priority and type of emergency, the determinant code is more specific and useful than a generic alarm that provides little to no description. An embodiment of a determinant code calculator 216 given in terms of its corresponding GUI is discussed in more detail in FIG. 6 below.

The emergency dispatch protocol 210 includes and operates a personnel instructions engine 217 to provide instructions that are appropriate to instruct the personnel that are part of the dispatch on how to appropriately respond to the emergency. As described below, these instructions may be based on information about the emergency from either and/or both of the determinant code calculator 216 and the sensor data engine 240 and delivered to the personnel that are to arrive as part of the dispatched response to the emergency.

The computer device 206 may include a reporting module 224 to statistically measure the performance of individual staff and overall performance of the dispatch center 202. The statistics may include compliance rates, communication processing statistics, and peer measurements. Once the communication with the information provider 214 is complete, the dispatcher 204 may close the case, and a case summary may be saved. The case summary may be retrieved later by the reporting module 224 for review and/or analysis. The reporting module 224 may determine statistics from the case summaries and/or while the cases are open.

The network interface 232 of the computer device 206 may be connected to a network 242. The computer device 206 may use the network interface 232 to send information to and receive information from one or more devices that may be other than the computer device 206, such as other devices of the dispatch center 202 (e.g., the telephone equipment 226) and/or devices outside the dispatch center 202 that are accessible on the network 242 (e.g., an Emergency Responder or CAD system 218, the phone 238, or other device, such as a laptop computer, used by the information provider 214, the one or more external devices 220, and/or the external device database 222). Examples of possible networks include the Internet and/or a Local Area Network (LAN) associated with the dispatch center 202 in order to facilitate information transfer between the computer device 206 and these other devices.

By way of example, the network 242 may facilitate information transfer between the computer device 206 and one or more external devices 220. This information may include external sensor data (whether raw or formatted) that is being transferred from one or more of the external devices 220 to the computer device 206. This information may include requests from the computer device 206 to one or more of the external devices 220 for the one or more external devices 220 to provide external sensor data to the computer device 206.

As another example, the network 242 may facilitate information transfer between the computer device 206, the Emergency Responder or CAD system 218, and one or more service vehicles and/or other units that may be dispatched to the location of an incident. The CAD system 218 may be used by the dispatcher 204 to track and allocate emergency response resources, in the manner discussed in relation to FIG. 1 above. The CAD system 218 may operate in whole or in part on a separate computer in communication with the computer device 206.

As another example, the network 242 may facilitate information transfer between the computer device 206 and the external device database 222. Information that may be transferred by the external device database 222 to the computer device 206 includes information about the geographic location of one or more of the external devices 220, information about an association between a person and one or more of the external devices 220, an external device identifier associated with one or more of the external devices 220, and information about the type(s), format(s), and/or quality(ies) of external sensor data that may be provided by one or more of the external devices 220.

Figure 3:
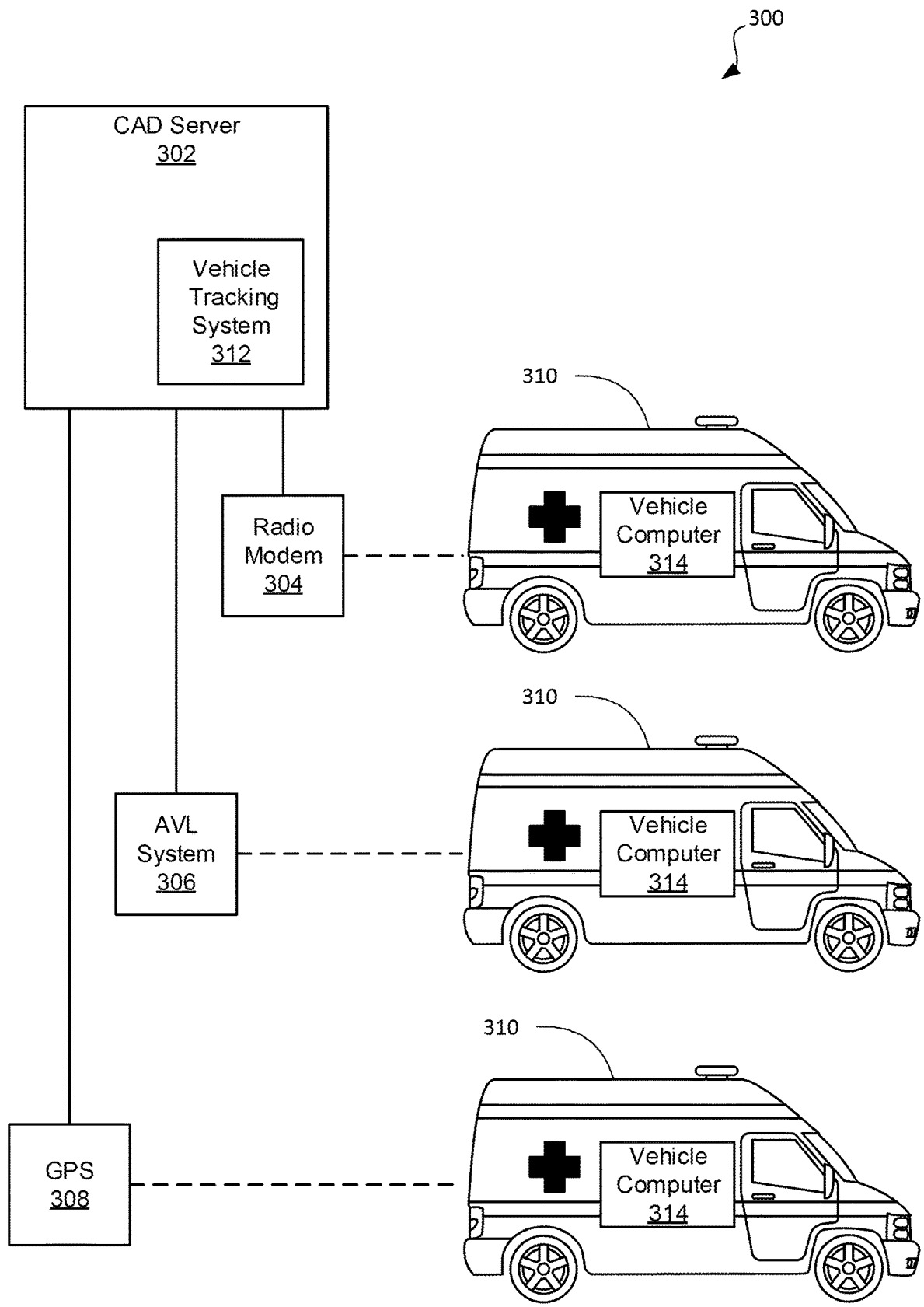
FIG. 3 illustrates a computer-aided dispatch system in accordance with one embodiment.

Referring to FIG. 3, an embodiment of a CAD system 300 for use with the systems disclosed herein is illustrated. The CAD system 300 may include one or more CAD servers 302 that are in electrical communication with the computing device 206. A CAD server 302 may be physically located in a dispatch center 202 or located remotely. The CAD server 302 may maintain a record of every emergency dispatch that is supported by the CAD server 302.

The CAD system 300 may include a radio modem 304, AVL system 306, and/or a GPS 308 (collectively referred to herein as "vehicle tracker devices") to wirelessly communicate with emergency vehicles 310. Although the GPS 308 is shown as a device separate from the AVL system 306, the AVL system 306 may utilize GPS signals in operation. One of skill in the art will appreciate that other wireless navigation systems, such as GLONASS, may also be incorporated into the system 300. The vehicle tracker devices are capable of receiving vehicle location information and determining the geographic location of emergency vehicles 310. The vehicle tracker devices may communicate with the emergency vehicles 310 through use of SMS, GPRS, satellite radio, terrestrial radio, and the like.

The CAD server 302 may include a vehicle tracking system 312 which includes software functionality to utilize vehicle location information and tracks all emergency response vehicles 310 communicating with the CAD server 302. The vehicle tracking system 312 may generate a comprehensive view of emergency vehicle locations. The vehicle tracking system 312 may generate a graphical user interface to display emergency vehicle locations.

Each emergency response vehicle 310 includes a vehicle computer 314 that wirelessly communicates with a vehicle tracker device. In one embodiment, the vehicle computer 314 may include a mobile data terminal or mobile digital computer to enable communication with the CAD server 302. A vehicle computer 314 may include a ruggedized laptop computer or tablet with a Wide-Area Wireless IP communication device and/or a radio interface. A vehicle computer 314 may be a dumb terminal, customized computer, general purpose computer and the like. As can be appreciated, the vehicle computer 314 may be anchored to the vehicle 310 for security and safety. The vehicle computer 314 may include one or more peripheral devices or built-in configuration for SMS. WAN, WLAN, GPS, and/or radio communication.

Monitoring the location, current dispatch assignments, equipment, and personnel of emergency response vehicles 310 informs the CAD server 302 and dispatch center 202 which vehicles 310 are available, suitably equipped, and in proximity to the emergency based on priority. An high priority emergency may require the closest suitable emergency response vehicle 310. A low priority emergency may allow for suitable emergency response vehicles that are farther away. Further, the priority may determine whether the emergency response vehicle proceeds with normal traffic or lights-and-siren. Conventionally, an emergency response vehicle 310 may be selected based on availability and proximity, but not based on a determinant code generated from, at least in part, external sensor data. The determinant code, as disclosed herein, confirms the type of emergency and the priority so that a suitable emergency response vehicle 310 is selected. Thus, an appropriate emergency response vehicle 310 with the right equipment, trained personnel, and suitable distance may be selected. Further, the emergency response vehicle 310 selection is automated to thereby reduce human error, reduce dispatch time, and reduce stress on the dispatcher. Increasing dispatch time by even mere moments can mean the difference between life and death. Quickly and accurately generating a determinant code from external sensor data provides a significant improvement to conventional systems.

Figure 4:
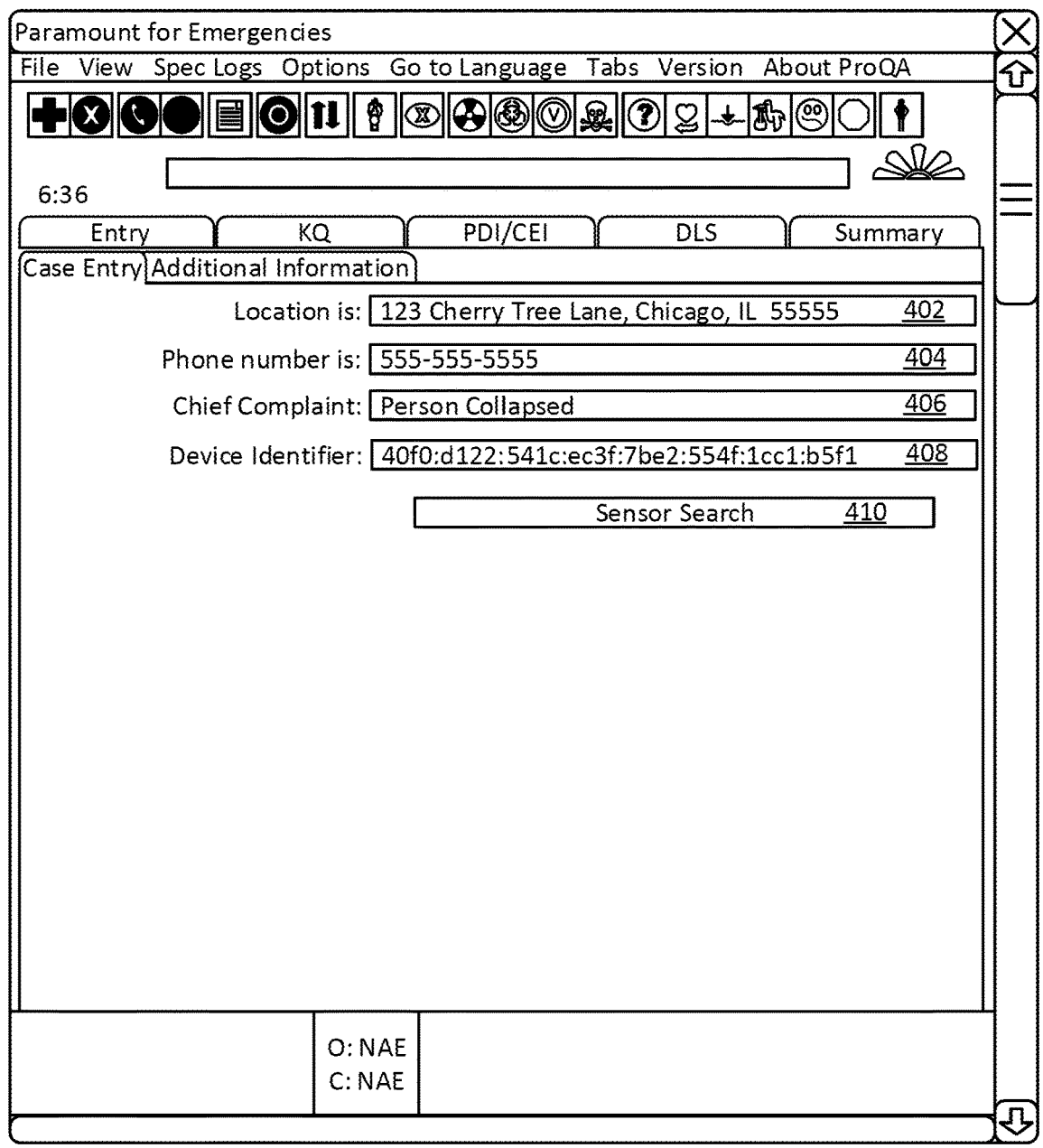
FIG. 4 illustrates a user interface in accordance with one embodiment.

FIG. 4 illustrates a user interface 400 of a case entry protocol of an emergency dispatch protocol, according to an embodiment. The emergency dispatch protocol may be, for example, the emergency dispatch protocol 210. The user interface 400 may correspond to the case entry protocol 236 of FIG. 2. The user interface 400 may operate on a computing device of a dispatch center (e.g., the computing device 206 of the dispatch center 202). The user interface 400 includes a location field 402, a phone number field 404, an emergency description field 406, an external device identifier field 408, and a sensor search button 410. The user interface 400 may be used by a dispatcher of a dispatch center (e.g., the dispatcher 204 of the dispatch center 202) when communicating with an information provider (e.g., the information provider 214).

The location field 402 may be filled manually by a dispatcher 204. A dispatcher 204 may ask an information provider 214 about their current location. Alternatively, the dispatcher 204 may ask an information provider 214 to provide the location of the emergency being reported by the information provider 214. In either case, the dispatcher 204 may then enter this information into the user interface 400 (for example, by using an input device (e.g., input device 228)).

The location field 402 may instead be automatically filled during the call (or other communication) with the information provider 214. For example, the call (or other communication) may arrive at the dispatch center 102 along with location information (e.g., GPS data that arrives with a communication from a smartphone). The location information may be automatically populated into the location field 402. A dispatcher 204 using user interface 400 may have the ability to override this data using an input device (e.g., in the event that the information is incorrect or the information provider 214 is reporting a location that is different than the automatically received information).

The location field 402 may accept location information in the form of text. The text may reflect, for example, GPS coordinates, a street address, or any other appropriate form of identifying a location. The computing device operating user interface 400 (or another computing device in network communication with such computer device) may be able to analyze this text and identify a location consistent with a common location scheme, as needed (e.g., to provide common location information to devices in communication with the computing device 206 of the dispatch center 202).

The phone number field 404 may be filled manually by a dispatcher 204 in response to inquiry of the information provider 214. Alternatively, the phone number field 404 may be automatically filled during the communication with the information provider 214 with information that arrives at the dispatch center 202 automatically along with the communication.

The chief complaint field 406 may be entered manually by the dispatcher 204 in response to inquiry of the information provider 214. One aim of the case entry protocol 236 may be to obtain sufficient information from the caller to permit identification by the dispatcher 204 of the chief complaint of the information provider 214. As part of the case entry protocol 236, the dispatcher 204 may ask the information provider 214 for a description of the incident, and may then fill the chief complaint field 406 with an indication of a corresponding chief complaint that best represents such description. The indication of the chief complaint may be, e.g., text based, such as "PERSON COLLAPSED," "BURGLARY IN PROGRESS" or "STRUCTURE ON FIRE." In some embodiments, the indication of the chief complaint may be a number that is assigned to (and known by the dispatcher and/or the computing device to be assigned to) a certain chief complaint corresponding to these or other ideas. The chief complaint (as reflected by the contents of the chief complaint field 406) may be used by the computing device 206 to determine, for example, which particular embodiment (of multiple possible embodiments) of an interrogation protocol (e.g., a particular embodiment of the interrogation protocol 234) should be used as the emergency dispatch protocol 210 proceeds. The specific embodiment of the interrogation protocol 234 selected may be selected because it includes pre-programmed inquiries (described below) that are related to the chief complaint indicated by the contents of the chief complaint field 406.

Alternatively, the chief complaint field 406 may be populated automatically by the interrogation protocol 234 based on answers to the pre-programmed inquiries. The chief complaint may also be populated automatically based on answers to the pre-programmed inquiries and the external sensor data. The chief complaint may also be referred to as an emergency and the emergency may be determined in the same manner as the chief complaint. Thus, a chief complaint or emergency may be manually entered or manually selected by a dispatcher 204 based on the dispatcher 204 receiving answers to pre-programmed inquiries. The dispatcher 204 may also view external sensor data in deciding the chief complaint or emergency. The chief complaint or emergency may also be automatically selected by the interrogation protocol 234 and/or the sensor data engine 240 based on the received answers to the pre-programmed inquiries, the external sensor data, or both.

The external device identifier field 408 may be filled automatically during a communication with the information provider 214 with information that arrives at the dispatch center 202 along with the communication. The contents of the external device identifier field 408 may include an external device identifier (as described below) for the device that is being used to communicate with the dispatcher 204.

The sensor search button 410 may be used to immediately pull up a GUI of a sensor data engine (e.g., the sensor data engine 240). Alternatively, as described below, the sensor search button 410 may cause a sensor data engine 240 to run in the background automatically without GUI interaction with the dispatcher 204. The operation of a sensor data engine 240 will be described in more detail below.

FIGS. 5A-5E illustrate various screens of a user interface 500 of an interrogation protocol of an emergency dispatch protocol, according to an embodiment. The emergency dispatch protocol may be, for example, the emergency dispatch protocol 210. The user interface 500 may correspond to the interrogation protocol 234 of FIG. 2. The user interface 500 may operate on a computing device of a dispatch center (e.g., the computing device 206 of the dispatch center 202). The user interface 500 may be used by a dispatcher of a dispatch center (e.g., the dispatcher 204 of the dispatch center 202) when communicating with an information provider (e.g., the information provider 214). As will be described, each screen of the user interface 500 may include a sensor search button 512, which may be used to immediately pull up a GUI of a sensor data engine (e.g., the sensor data engine 240). Alternatively, as described below, the sensor search button 512 may case a sensor data engine 240 to run in the background automatically without GUI interaction with the dispatcher 204. The operation of a sensor data engine 240 will be described in more detail below.

Figure 5A:
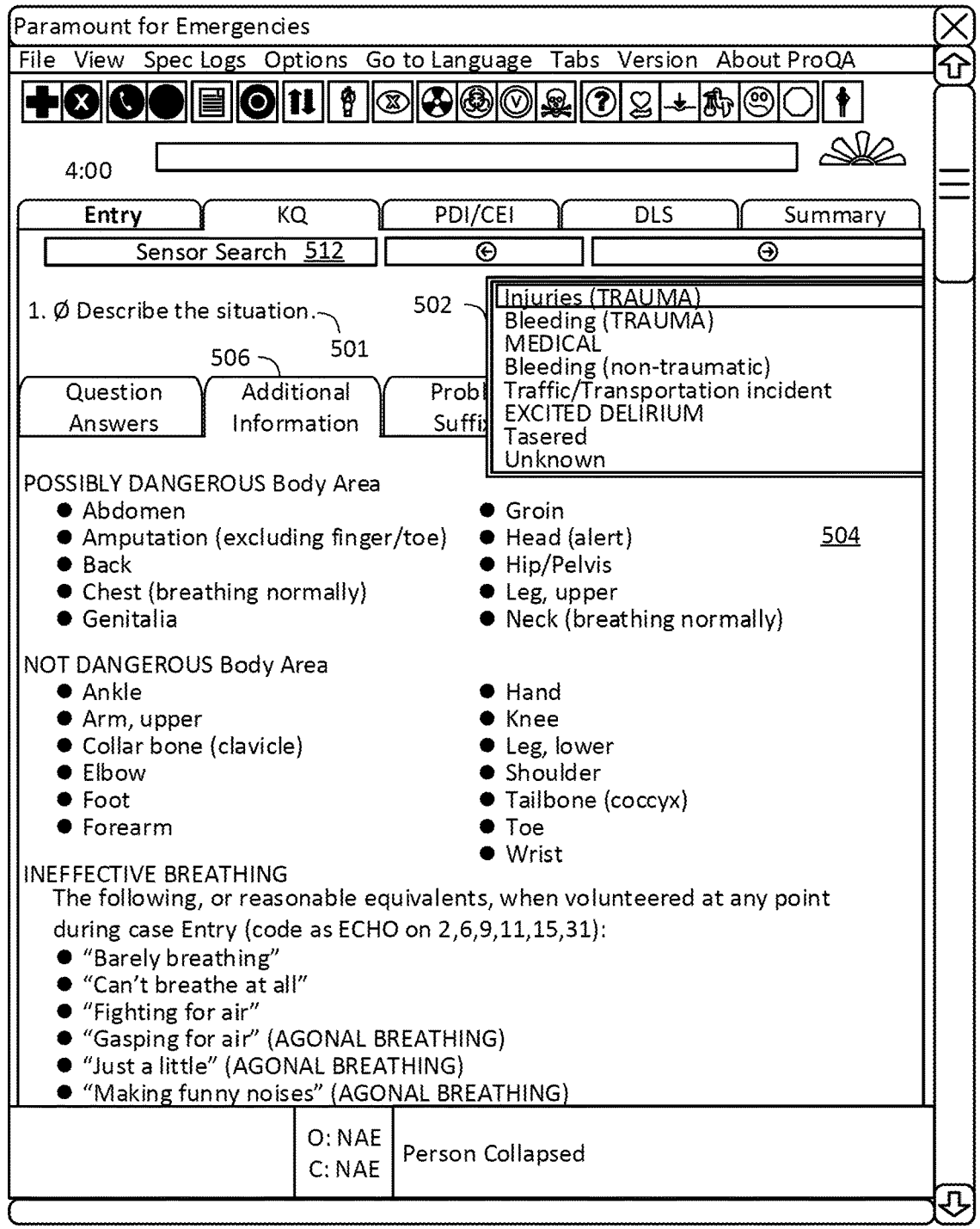
FIGS. 5A-5E illustrate a user interface in accordance with one embodiment.

In FIG. 5A, the user interface 500 prompts the dispatcher 204 to receive the main problem or incident type by conveying the pre-programmed inquiry "Describe the situation" 501 to the information provider 214 and receiving a corresponding response. The user interface 500 may provide a list 502 that includes problem categories such as "Injuries (TRAUMA)," "Bleeding (TRAUMA)," "MEDICAL," "Bleeding (non-traumatic)," "Traffic/Transportation incident," "EXCITED DELIRIUM," "Tasered," or "Unknown." Each of these problem categories may have been placed in the list 502 of the user interface 500 of the interrogation protocol 234 because of initial information provided in an emergency description field of a GUI of a case entry protocol (e.g., the chief complaint or emergency description field 406 of the user interface 400). Accordingly, the specific selection and arrangement of the categories as shown in the list 502 at this stage are given by way of example and not by way of limitation. Other lists with categories or items other than what has been expressly presented herein (e.g., that are related to an entirely different type of emergency other than injury to a person) are contemplated. The categories found in the list 502 may correspond to initial information indicating that the information provider 214 is reporting that they have come across a victim 212 who has apparently collapsed.

The dispatcher 204 may highlight and select any one of the problem categories found in the list 502. This selection may be based on information acquired from interrogating the information provider 214 that is communicating with the dispatcher 204. In FIG. 5A, the problem category selected is "Injuries (TRAUMA)."

FIG. 5A shows an embodiment of the contents of the "Additional Information" field 504. The "Additional Information" field 504 may contain information to help the dispatcher 204 appropriately respond to queries that may be presented by the user interface 500. The "Additional Information" field 504 may be displayed by default prior to the selection of, for example, the problem category by the dispatcher 204 (or by default prior to input by the dispatcher 204). Alternatively, the dispatcher 204 may have previously selected the associated "Additional Information" tab 506 in order to display the "Additional Information" field 504. This screen of the user interface 500 may further include a sensor search button 512, which may be used to immediately activate a GUI of a sensor data engine (e.g., the sensor data engine 240).

Figure 5B:
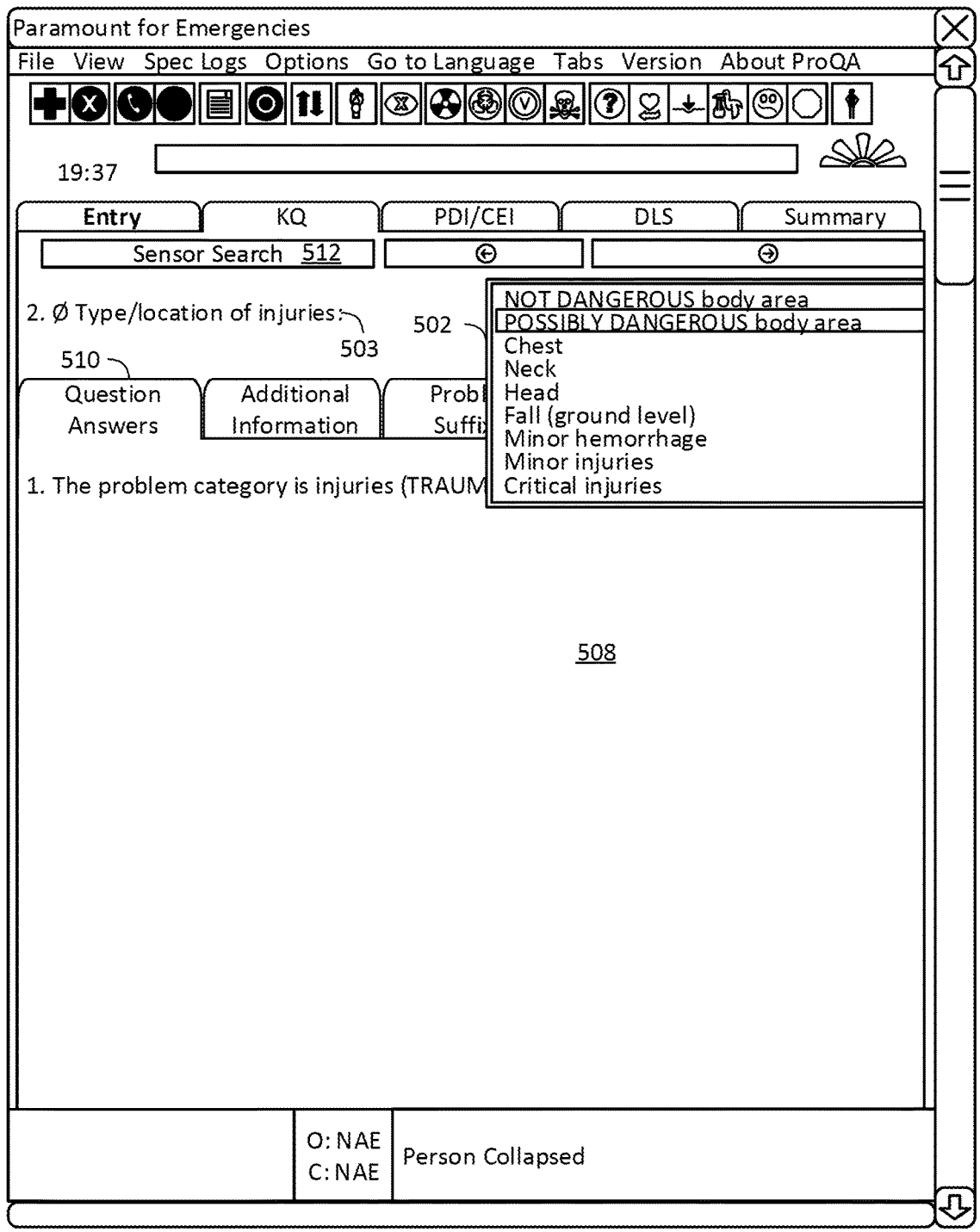

In FIG. 5B, the user interface 500 modifies the list 502 to prompt the dispatcher 204 to receive the type of injuries/incident by conveying the pre-programmed inquiry "Type/location of injuries" 503 to the information provider 214 and receiving a corresponding response. The list 502 may provide an option to select "NOT DANGEROUS body area," "POSSIBLY DANGEROUS body area," "Chest," "Neck," "Head," "Fall (ground level)," "Minor hemorrhage," "Minor injuries," or "Critical injuries." As indicated, "POSSIBLY DANGEROUS body area" is selected by the dispatcher 204. This selection may be based on information acquired from interrogating the information provider 214 that is communicating with the dispatcher 204.

FIG. 5B shows an embodiment of a "Question Answers" field 508. The "Question Answers" field 508 may be displayed automatically in response to the selection of the main problem category (or other selections described herein) by the dispatcher 204, as described relative to FIG. 5A above. Alternatively, the dispatcher 204 may have selected the associated "Question Answers" tab 510 in order to display the "Question Answers" field 508. The "Question Answers" field 508 is updated with the answer to the previous prompt as the interrogation protocol 234 proceeds. This screen of the user interface 500 may further include the sensor search button 512.

Figure 5C:
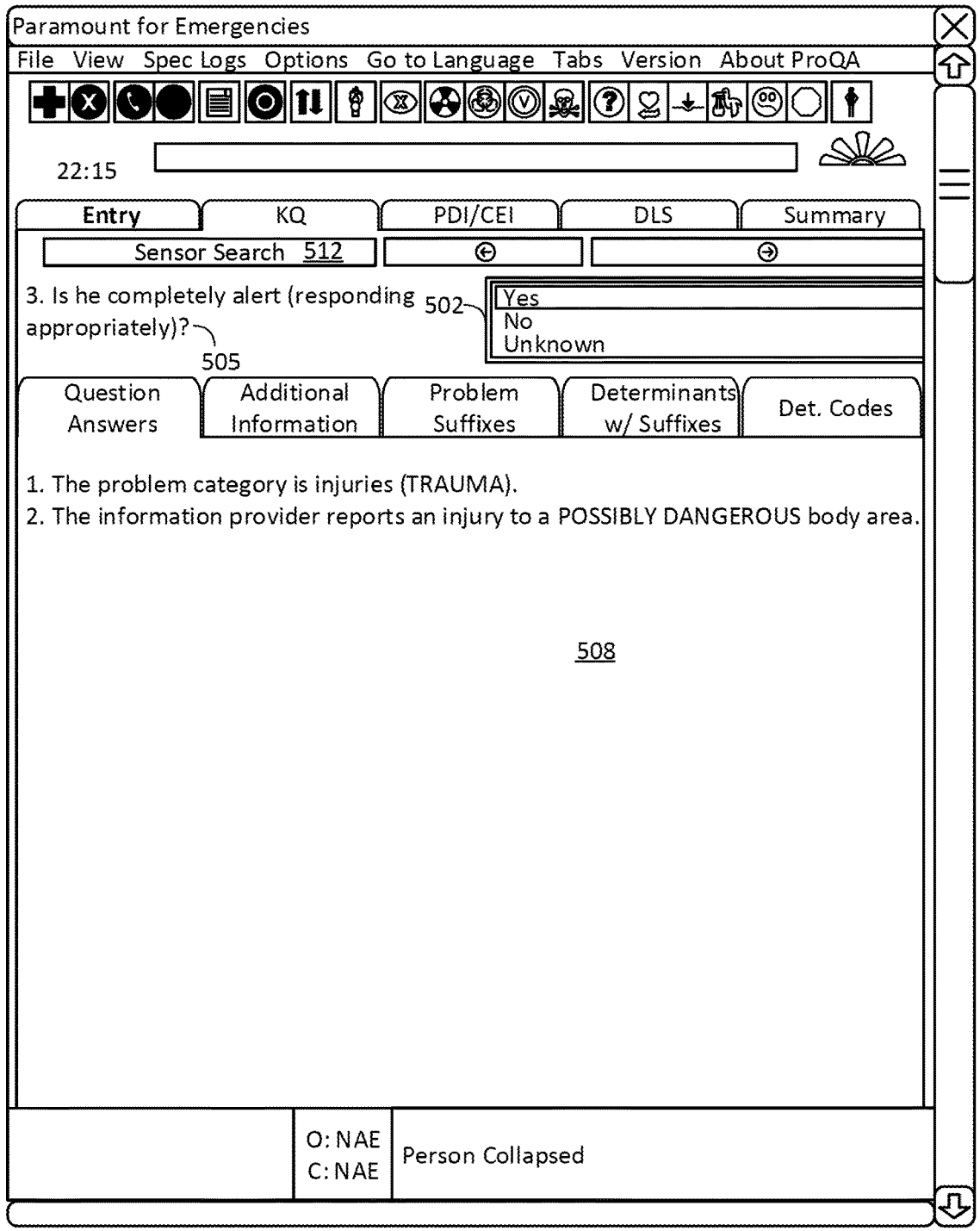

In FIG. 5C, the user interface 500 prompts the dispatcher 204 to determine whether the victim 212 is completely alert by conveying the pre-programmed inquiry "Is he completely alert (responding appropriately)?" 505 to the information provider 214 and receiving a corresponding response. The list 502 may provide an option to select "Yes," "No," or "Unknown." As indicated, "Yes" is selected. This selection may be based on information acquired from interrogating the information provider 214 that is communicating with the dispatcher 204. The user interface 500 may provide a "Question Answers" field 508 to list previously entered answers. This provides a visual indicator to the dispatcher 204 and will be saved as a record. As indicated, the problem category is "injuries (TRAUMA)" and the information provider reports that the injury is to a "POSSIBLY DANGEROUS body area." As shown, the "Question Answers" field 508 is updated with the answer to the previous prompt as the interrogation protocol 234 proceeds. This screen of the user interface 500 may further include the sensor search button 512.

Figure 5D:
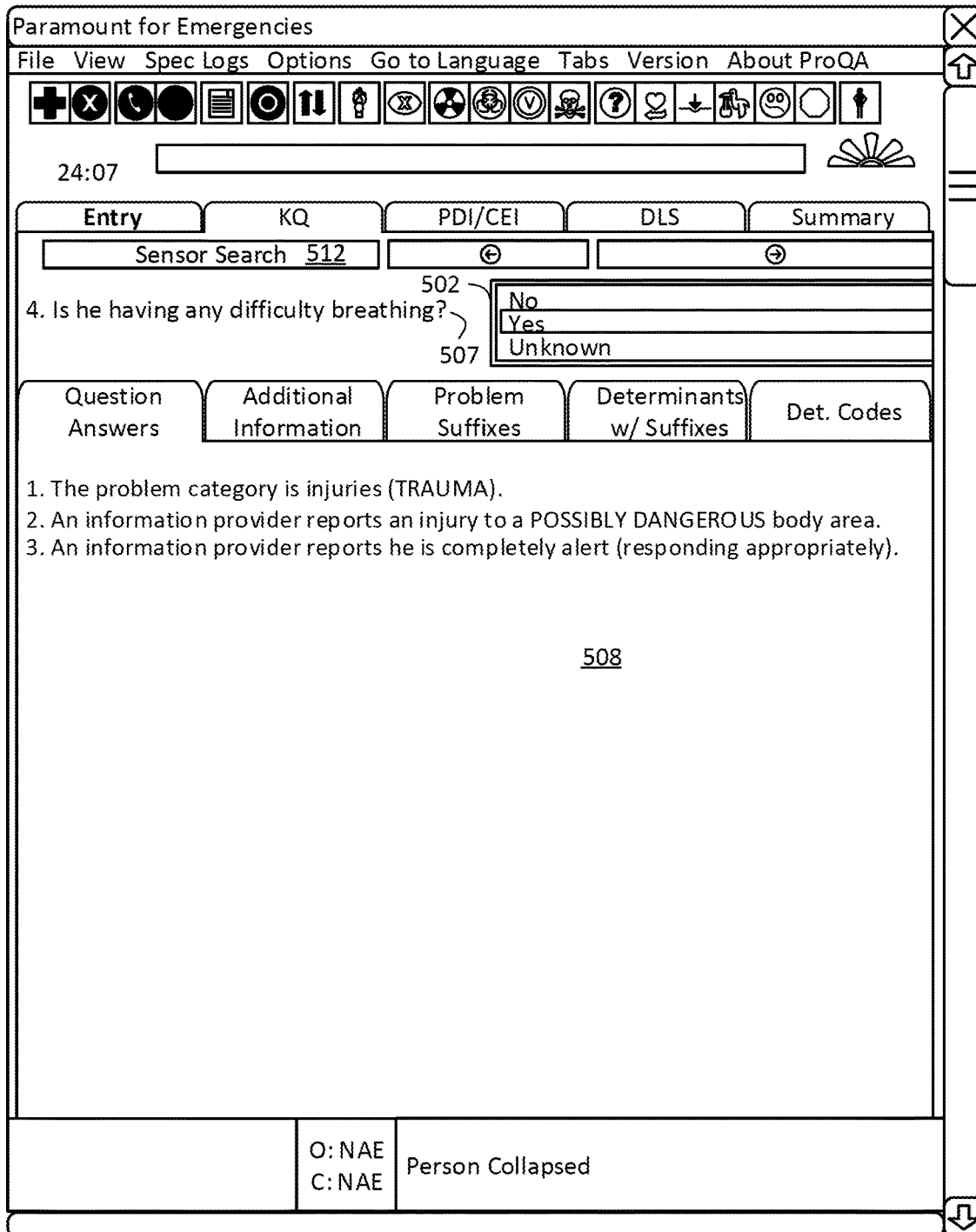

In FIG. 5D, the user interface 500 prompts the dispatcher 204 to determine whether the victim 212 is having difficulty breathing by conveying the pre-programmed inquiry "Is he having any difficulty breathing?" 507 to the information provider 214 and receiving a corresponding response. The list 502 may provide an option to select "No," "Yes," or "Unknown." As indicated, "Yes" is selected. This selection may be based on information acquired from interrogating the information provider 214 that is communicating with the dispatcher 204. As shown, the "Question Answers" field 508 is updated with the answer to the previous prompt as the interrogation protocol 234 proceeds. This screen of the user interface 500 may further include the sensor search button 512.

Figure 5E:
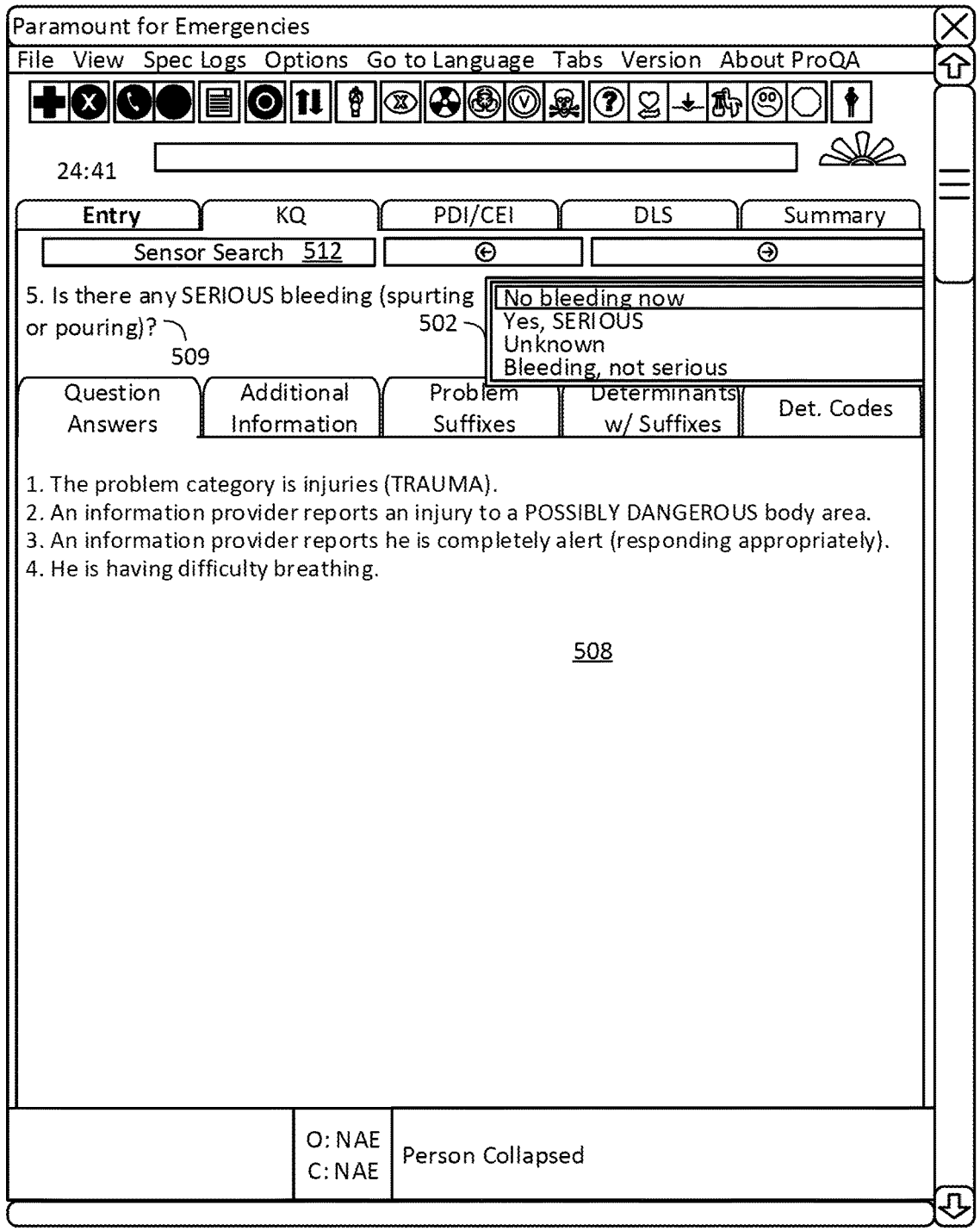

In FIG. 5E, the user interface 500 prompts the dispatcher to determine whether the victim 212 is seriously bleeding by conveying the pre-programmed inquiry "Is there any SERIOUS bleeding (spurting or pouring)?" 509 to the information provider 214 and receiving a corresponding response. The user interface 500 may provide an option to select "No bleeding now," "Yes, SERIOUS," "Unknown," or "Bleeding, not serious." As indicated, "No bleeding now" is selected. This selection may be based on information acquired from interrogating the information provider 214 that is communicating with the dispatcher 204. As shown, the "Question Answers" field 508 is updated with the answer to the previous prompt as the interrogation protocol 234 proceeds. This screen of the user interface 500 may further include the sensor search button 512.

FIGS. 6A-6D illustrate various screens of a user interface 600 corresponding to a sensor data engine of an emergency dispatch protocol, according to an embodiment. The emergency dispatch protocol may be, for example, the emergency dispatch protocol 210. The user interface 600 may correspond to the sensor data engine 240 of FIG. 2. The user interface 600 may operate on a computing device of a dispatch center (e.g., the computing device 206 of the dispatch center 202). The user interface 600 may be used by a dispatcher of a dispatch center (e.g., the dispatcher 204 of the dispatch center 202) when communicating with an information provider (e.g., the information provider 214). The user interface 600 may have been invoked during any other portion of the emergency dispatch protocol 210 (e.g., automatically, or in response to the dispatcher 204 using a sensor search button associated with another part of the emergency dispatch protocol 210).

While the processes shown in FIGS. 6A-6D will be shown in the context of the GUI user interface 600, it should be understood that (as discussed below) these processes may each instead be automatically performed by an appropriately programmed computing device 206 of a dispatch center 202. In these cases, it may be that the user interface 600 is not used by the computing device 206 and/or presented to the dispatcher 204 and that the processes of the sensor data engine 240 as described in relation to FIGS. 6A-6D are performed in the background for the dispatcher 204 when the sensor data engine 240 runs. This may allow the dispatcher 204 to continue to, for example, receive answers to pre-programmed inquiries of an interrogation protocol (e.g., the interrogation protocol 234) at the same time the system is automatically performing the processes corresponding to a sensor data engine 240 (e.g., receiving sensor data, calculating data values, etc., as discussed below). In some embodiments, the sensor data engine 240 may run automatically and/or in the background upon receipt of a location and/or identification data from the phone 238 of the information provider 214, as will be described in further detail below.

The user interface 600 may include a location field 602, a location search button 604, a name/user identification field 606, and an identification search button 608. The user interface 600 may further include a search results field 610, a sensor readings field 612, and an add sensor data button 614. The user interface 600 may further include a collected results field 616, a chief complaint likelihood field 618, a determinant code field 620, and a confirm and return button 622.

Figure 6A:
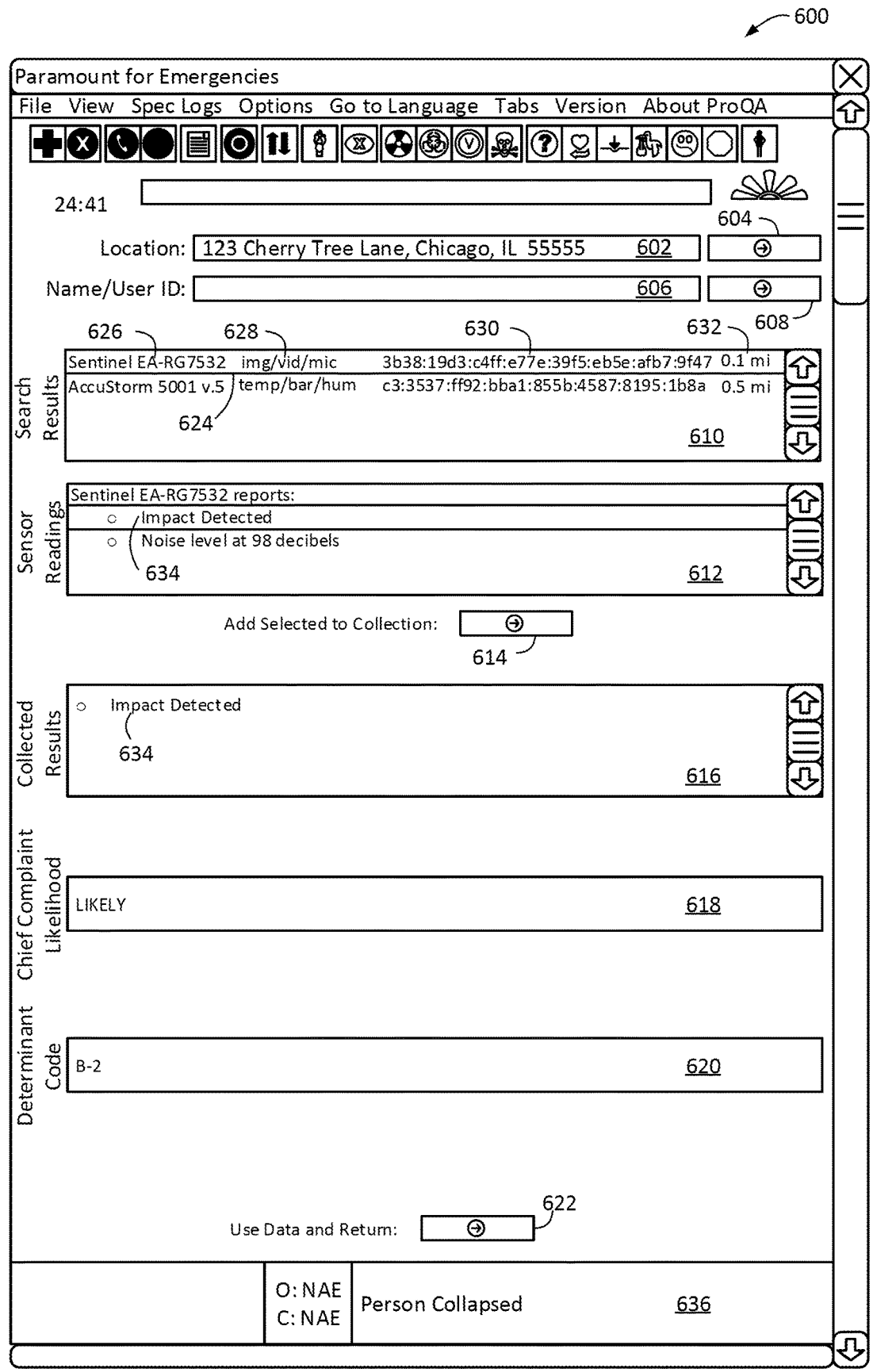

In FIG. 6A the location field 602 has been filled with an address. This may have occurred automatically (e.g., the address may have been retrieved from a case entry protocol 236 and/or an interrogation protocol 234 of the emergency dispatch protocol 210). Alternatively, the address may have been entered manually by the dispatcher 204. The address may correspond to a location at or near the location of an emergency, and may have been provided to the dispatcher 204 by the information provider 214 (or automatically) as described above. In alternative embodiments, other location information (e.g., a set of GPS coordinates) may appear in the location field 602 instead of (or in addition to) an address. Any location information that can be used by a computer system to determine a relevant area of the emergency may be used in the location field 602. The case entry protocol 236 may include a search feature to confirm the incident address from one or more external devices 220. For example, the incident address may be received from a smartphone of the information provider 214, a nearby security sensor, a medical sensor carried by a victim/patient or the information provider 214, a vehicle sensor, and the like. Any one of the external devices 220 may include a GPS or any other known location service.

The dispatcher 204 then presses the location search button 604 to perform a search for devices with external sensors present in one or more external devices 220 that exist in the area of the identified location (alternatively, this search may occur automatically). In response, the computing device 206 of the dispatch center 202 may communicate with an external device database (e.g., the external device database 222 of FIG. 2) and present this location information to the external device database 222. It may be that the computing device 206 of the dispatch center 202, the external device database 222, or another computing device 206 (e.g., one accessed via the network 242) may have previously transformed the location information from the location field 602 to a format recognizable to the external device database 222. The external device database 222 may receive this location information and reply with a list of results containing details about external devices in the area that are capable of providing data to the computing device 206 of the dispatch center 202.

This list of capable external devices 220 may be presented in the search results field 610. As shown, results corresponding to external devices 220 in vicinity to the location are displayed in the search results field 610. A first external device 624 (and/or any other external device in this list) may be displayed with an external device name 626. The external device name 626 may be a name that was set by a manufacturer, installer, owner, or user of the external device name 626.

The first external device 624 (and/or any other external device in this list) may include an external device sensor list 628. This external device sensor list 628 may describe the types of sensors and sensor readings that may be provided by the first external device 624.

A first external device 624 (and/or any other external device in this list) may include an external device identifier 630. This external device identifier 630 may be a unique external device identifier associated with the first external device 624. In the example of FIG. 6A, Internet Protocol Version 6 (IPv6) addresses are used as external device identifiers; however, other examples of external device identifiers (Internet Protocol Version 4 (IPv4) addresses, Media Access Control (MAC) addresses, etc.) are also contemplated.

A result corresponding to the first external device 624 (and/or any other external device in this list) may include a distance 632 of the first external device 624 from the location of the emergency/incident. This distance may have been calculated by the computing device 206 of the dispatch center 202 based on absolute location details about the external device 624 provided in the response from the external device database 222.

The dispatcher 204 may select a result corresponding to one of the external devices 220 displayed in the search results field 610. Alternatively, the computing device 206 of the dispatch center 202 may be programmed to make a selection of one of the external devices 220 automatically. The dispatcher 204 and/or the computing device 206 may make a selection of an external device 220 based on the location of the external device 220 (e.g., an external device 220 that is closest to the location of the emergency). The dispatcher 204 and/or the computing device 206 may make a selection of an external device 220 based on the type of external sensor data to be provided by the external device 220. This decision may be made based on the facts reported by the information provider 214 (e.g., the selection of an external device 220 that can provide ambient temperature data may be based on the fact that the information provider 214 has reported a fire in the area). This decision may be made based on answers to the pre-programmed inquiries received from the information provider 214 (e.g., the selection of an external device 220 that can provide respiration data may be based on an answer to a pre-programmed inquiry that indicates that a victim 212 of an emergency may not be breathing).

As illustrated, a first external device 624 has been selected by the dispatcher (or, alternatively, has been automatically selected by the computing device 206). Once the dispatcher 204 and/or the computing device 206 selects the first external device 624, the computing device 206 of the dispatch center 202 may request sensor data from the selected external device 624 via the network 242. This request may be facilitated by the use of the external device identifier 630 of the first external device 624 in the request. The first external device 624 may then reply with its external sensor data in the manner described above in relation to FIG. 1. In some embodiments, the first external device 624 may first require the computing device 206 of the dispatch center 202 to provide authorization credentials to verify that the request is indeed coming from the dispatch center 202 (and therefore the external sensor data will presumably be used for legitimate dispatching purposes).

Once the external sensor data from the first external device 624 is received, the sensor readings field 612 may populate with one or more data value(s) associated with that external sensor data. These data value(s) may be determined directly from external sensor data in the case that such external sensor data provides information in data value form. For example, a data value that is a decibel level may be determined directly from external sensor data that reports audio levels in terms of decibel values.

In other cases, these data values must be determined from the external sensor data by analyzing that same external sensor data at the sensor data engine 240 of the emergency dispatch protocol 210. To do this, the sensor data engine 240 may be programmed to look for certain relevant facts that may be anticipated to potentially be shown by external sensor data of a given type. For example, the sensor data engine 240 may be programmed to determine an impact or collision based on the received audio level including the decibel values. In the embodiment of FIG. 6A, the sensor data engine 240 has analyzed the audio feed data from the first external device 624 and has determined that there is an impact. A data value and/or an analysis is reported to the dispatcher 204 in the sensor readings field 612.

A data value may be a number (a temperature, a number of people, a heart rate, etc.). Alternatively, a data value may be a binary indication (an indication of whether a person is breathing, an indication of whether it is raining, etc.).

The sensor readings field 612 illustrates a data value of 98 decibels and an analysis that an impact is detected. The dispatcher 204 may review data values and/or data analyses and select one or more of them to provide to the rest of the emergency dispatch protocol 210. Alternatively, the computing device 206 may be programmed to automatically pick out one or more of the data values and analyses to provide to the rest of the emergency dispatch protocol 210. It is contemplated that in some embodiments, all of the data values and analyses associated with the external sensor data are selected to be provided to the rest of the emergency dispatch protocol 210.

The first external device 624 may also capture video data and, in addition to audio, list a video data value in the sensor readings field 612. The video data value may be listed as "movement detected" or "abrupt movement detected." In one embodiment, an icon may be provided next to either video or audio data values, listed in the sensor readings field 612, which allows a dispatcher 204 to play the corresponding video or audio data. Alternatively, or in addition, the sensor data engine 240 may make an analysis of the video and list the analysis in the sensor readings field 612. A video analysis may list a vehicle or individual collision, or in the given example, that a human body has collapsed. One skilled in the art will appreciate that video analysis logic is capable of identifying such events.

In the example of FIG. 6A, the dispatcher 204 has selected the first data value 634 regarding a detected impact from the first external device 624. The dispatcher 204 then presses the add sensor data button 614, which causes the first data value 634 to be added to the collected results field 616. Alternatively, the computing device 206 may add the first data value 634 to the collected results field 616 automatically. As will be described below, the collected results field 616 may contain one or more such data values.

The dispatcher 204 and/or the computing device 206 may then perform another search using, e.g., the location field 602, the location search button 604, the identification field 606, and/or the identification search button 608. Alternatively, the dispatcher 204 may use the confirm and return button 622 to confirm the results in the collected results field 616 for use with the emergency dispatch protocol 210 and return to the emergency dispatch protocol 210 when the user interface 600 corresponding to the sensor data engine 240 was invoked (or the computing device 206 may confirm the selection(s) in the collected results field 616 automatically).

The chief complaint likelihood field 618 may present the result of an analysis performed by the sensor data engine 240 of the likelihood that the chief complaint or emergency is accurate in light of the data values found in the collected results field 616. The chief complaint, which may also be referred to as the emergency, may be listed in the chief complaint field 636 which may be automatically populated from the case entry of FIG. 4. Alternatively, the chief complaint or emergency may be manually entered or selected by the dispatcher 204. The independent detection of an impact by the first external device 624 corroborates the information provided by the information provider 214. In the example of FIG. 6A, the first data value 634 located in the collected results field 616 indicates that an impact is detected. The sensor data engine 240 may calculate that this information is consistent with the chief complaint of "Person Collapsed." The sensor data engine 240 accordingly may modify the chief complaint likelihood field 618 to reflect a calculated "LIKELY" likelihood.

As discussed above, the sensor data engine 240 communicates the sensor data to the determinant code calculator 216. Accurate calculation of a determinant code, indicative of emergency type and priority, is a primary purpose of the present disclosure. Conventionally, a single sensor may generate a signal indicative of a specific emergency. For example, a dedicated fire alarm generates a fire alarm signal responsive to smoke and/or heat. A door alarm generates a signal indicative of intrusion. However, a single alarm is known to generate false alarms and is incapable of establishing an accurate priority. Multiple sensors generating multiple sensor data allows data compilation, as discussed herein, to accurately calculate a specific determinant code and associated emergency type and priority. In this way, multiple data points from multiple sources improve the accuracy and reliability of an emergency priority.

The determinant code field 620 displays a determinant code, in this case B-2. In the given example, a medical emergency of a moderately high priority is determined. The determinant code, representative of a type of emergency and emergency priority, is the result of an analysis performed by the determinant code calculator 216 based on the external sensor data.

As will be described below, it is possible that any number of data values associated with any variety of sensors may appear in the collected results field 616. In some cases, it may be that some or all of the data values may be consistent with the determinant code, emergency type, priority level, or chief complaint. These data values may be used to weigh in favor of finding a higher likelihood that the determinant code, emergency type, priority level, and/or chief complaint is accurate. For example, in a case where the determinant code, emergency type, priority level, and/or chief complaint indicates that there has been an earthquake, and one or more data values in the collected results field 616 report recent seismic activity of magnitude 8, the chief complaint likelihood field 618 may return a value of "LIKELY" or "HIGHLY LIKELY" (due to the fact that the chief complaint is corroborated by the one or more data values).

In some cases, it may be that some data values may be inconsistent with the determinant code, emergency type, priority level, and/or chief complaint. These data values may be used to weigh against the likelihood that the determinant code, emergency type, priority level and/or chief complaint is accurate. For example, in a case where the determinant code, emergency type, priority level, and/or chief complaint indicates that there has been a fire, but one or more data values in the collected results field 616 report temperatures between 68 and 75 degrees in all buildings near the information provider 214, the chief complaint likelihood field 618 may return a value of "UNLIKELY" likelihood or "HIGHLY UNLIKELY" likelihood (due to the fact that the chief complaint is not corroborated by the one or more data values).

In some cases, it may be that not every data value in the collected results field 616 is relevant to a determination about the likelihood of the determinant code, emergency type, and/or chief complaint. These may be ignored when calculating the likelihood of the determinant code, emergency type, and/or chief complaint. In cases where there are no data values in the collected results field 616 that are relevant to a determination about the likelihood of the determinant code, emergency type, priority level, and/or chief complaint, the likelihood value in the chief complaint likelihood field 618 may return a value of "UNKNOWN" likelihood.

In some cases, it may be that multiple data values in the collected results field 616 are equally (and oppositely) weighted in relation to the determinant code, emergency type, and/or chief complaint. In these cases, the data values may "cancel" each other out and the chief complaint likelihood field 618 may return a value of "UNKNOWN."

In some cases, the sensor data engine 240 runs prior to a determination of the determinant code, emergency type, priority level, and/or chief complaint. In these cases, it may be that a likelihood is not calculated, and the likelihood value in the chief complaint likelihood field 618 may return a value of "UNKNOWN" likelihood. In these cases, it may be that the likelihood value in the chief complaint likelihood field 618 may be updated by the sensor data engine (either manually or automatically) at any later time if/when a chief complaint is determined.

Figure 6B:
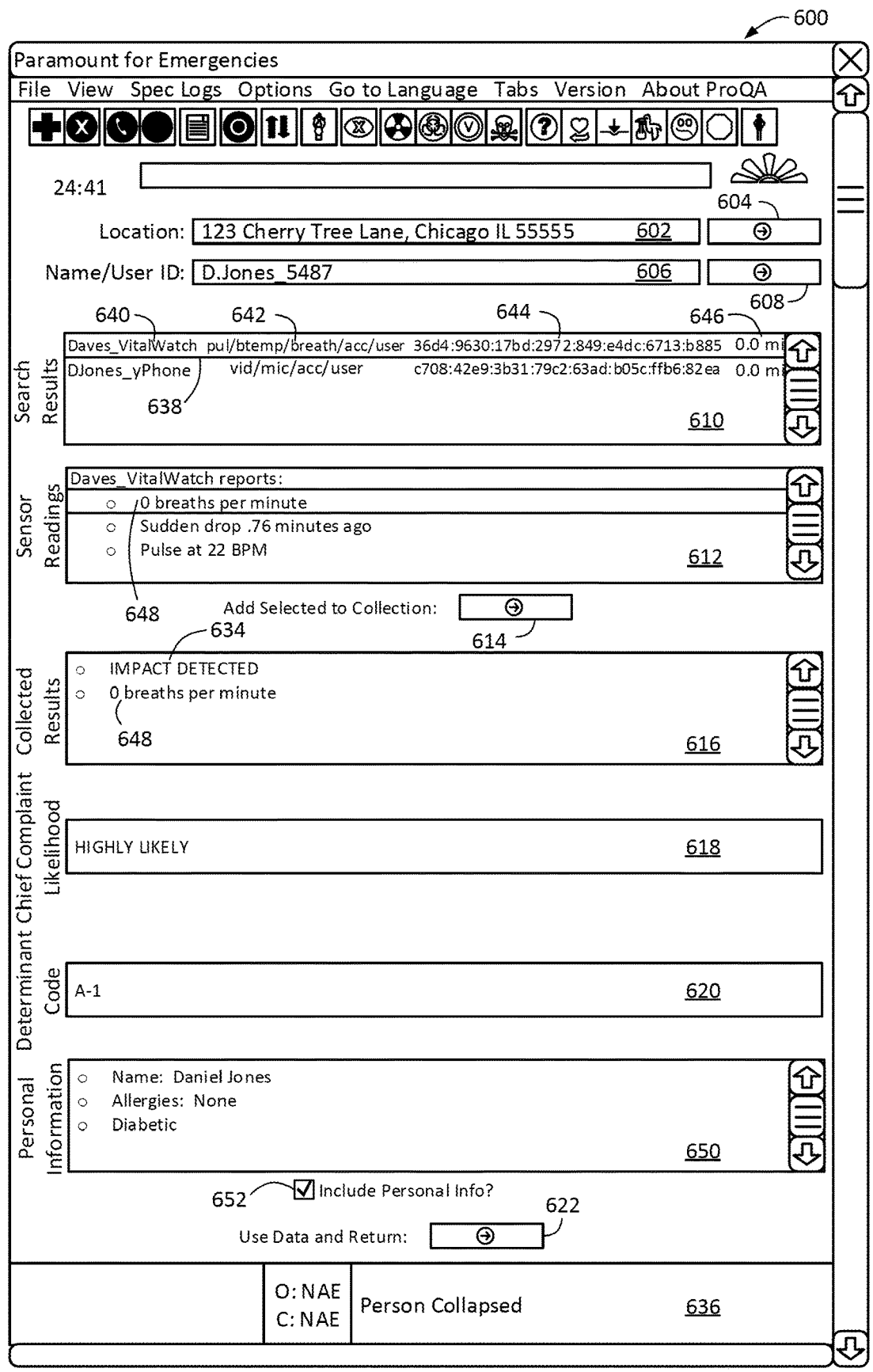

In FIG. 6B the identification field 606 has been filled with a username. This may have occurred automatically (e.g., the username may have been retrieved from a device that made the phone call to the dispatch center 202). Alternatively, the username may have been entered manually by the dispatcher 204 in response to information provided by the information provider 214. The username may be associated with the device that made the phone call to the dispatch center 202. Alternatively, the username may be associated with another device, such username having been discovered by the device that made the phone call to the dispatch center via, for example, Bluetooth and/or NFC communications. The username may correspond to a victim 212 who is a victim of an accident, who may or may not be the information provider 214. Alternatively, the username may correspond to a person who is not a victim but who is an information provider 214.

The dispatcher 204 presses the identification search button 608 to perform a search for external devices 220 with external sensors that are associated with the given username (or this search may occur automatically). In response, the computing device 206 of the dispatch center 202 may communicate with an external device database (e.g., the external device database 222 of FIG. 2) and present this username information to the external device database 222. The external device database 222 may have access to information regarding the external device identifiers of devices associated with a given username. The external device database 222 may receive this username information and reply with a list of external devices 220 associated with that username information that are capable of providing data to the computing device 206 of the dispatch center 202.

The list of capable external devices may be presented in the search results field 610. The search results field 610 may also list external devices previously selected, such as that in FIG. 6A. As illustrated in FIG. 6B, a second external device 638 has been selected by the dispatcher 204. Alternatively, the computing device 206 of the dispatch center 202 may be programmed to make a selection of one of the external devices 220 automatically. As shown, a result corresponding to the second external device 638 may have an external device name 640, an external device sensor list 642, an external device identifier 644, and a distance 646, similar to the description of FIG. 6A.

Once the dispatcher 204 selects the second external device 638 (as illustrated or, alternatively, once the second external device 638 is automatically selected by the computing device), the computing device 206 of the dispatch center 202 may request sensor data from the second external device 638 via the network 242 and receive external sensor data in reply, in the manner described above.

Once the external sensor data from the second external device 638 is received, the sensor readings field 612 may populate with data values associated with that external sensor data. In the given example, the second external device 638 includes physiological sensors to measure vitals of a human body. As before, these data values may be determined directly from external sensor data that was provided as a value in the external sensor data. For example, a data value that is breaths-per-minute may be determined directly from external sensor data that reports breathing data in terms of breaths per minute.

In other cases, these data values must be determined from the external sensor data by analyzing that same external sensor data at the sensor data engine of the emergency dispatch protocol 210. To do this, the sensor data engine 240 may be programmed to analyze raw external sensor data and convert it to a data value. For example, the sensor data engine 240 may be programmed to receive a signal from an external data sensor corresponding to a single detected heartbeat of a person wearing the sensor of an external device 220. In the embodiment of FIG. 6B, the sensor data engine 240 has analyzed this type of heartbeat data from the second external device 638 and has determined that the current heart rate is 22 beats per minute (BPM). This piece of information is reported as a data value to the dispatcher 204 in the sensor readings field 612.

The dispatcher 204 may review these data values and select one or more of them to provide to the rest of the emergency dispatch protocol 210. Alternatively, the computing device 206 may be programmed to automatically pick out one or more of these data values to provide to the rest of the emergency dispatch protocol 210. It is contemplated that in some embodiments, all of the data values associated with the external sensor data are selected to be provided to the rest of the emergency dispatch protocol 210. In the example of FIG. 6B, the dispatcher 204 has selected a second data value 648 regarding the breaths per minute as determined from the external data received from the second external device 638.

The dispatcher 204 then presses the add sensor data button 622, which causes the second data value 648 to be added to the collected results field 616. Alternatively, the computing device 206 may add the second data value 648 to the collected results field 616 automatically. As illustrated, the collected results field 616 contains both the second data value 648 and the first data value 634, which remained in the collected results field 616 after the activities described in relation to FIG. 6A.

In the example of FIG. 6B, the first data value 634 located in the collected results field 616 indicates that an impact is detected, and the second data value 648 located in the collected results field 616 indicates a reading of zero breaths per minute. The determinant code calculator may modify the determinant code list in the determinant code field 620 to indicate the existence of a specific medical emergency.

The impact and breathe rate is used by the determinant code calculator to confirm the accuracy of the determinant code of A-1 in the determinant code field 620. The sensor data engine 240 further determines that this information is consistent with the chief complaint of "PERSON COLLAPSED." The sensor data engine 240 accordingly may modify the chief complaint likelihood field 618 to reflect a "HIGHLY LIKELY" likelihood. The use of the "HIGHLY LIKELY" likelihood may reflect the fact that there are multiple data values consistent with the chief complaint.

FIG. 6B includes a personal data field 650. The personal data field 650 may have appeared in the user interface 600 in response to the fact that the second external device 638 has indicated to the sensor data engine 240 that personal information is available. The personal data field 650 may include one or more pieces of user data such as name, known allergies, known medical conditions, etc. The dispatcher 204 may click the personal information checkbox 652 if they desire to provide this information to the rest of the emergency dispatch protocol 210 (alternatively, the computing device 206 may determine to provide this information to the rest of the emergency dispatch protocol 210). This information may then be used to, e.g., inform and/or tailor instructions for personnel responding to an emergency that is a medical emergency involving the person, as described below. The dispatcher 204 (or alternatively, the computing device 206) may choose not to provide this information to the rest of the emergency dispatch protocol 210 if it is not relevant (e.g., if the emergency being reported is not a medical emergency of such user).

The dispatcher 204 and/or the computing device 206 may then perform another search using, e.g., the location field 602, the location search button 604, the identification field 606, and/or the identification search button 608. Alternatively, the dispatcher 204 may use the confirm and return button 622 to confirm the results in the collected results field 616 for use with the emergency dispatch protocol 210 and return to where they left off in the emergency dispatch protocol 210 when the user interface 600 corresponding to the sensor data engine 240 was invoked (or the computing device 206 may confirm the selection(s) in the collected results field 616 automatically).

Figure 6C:
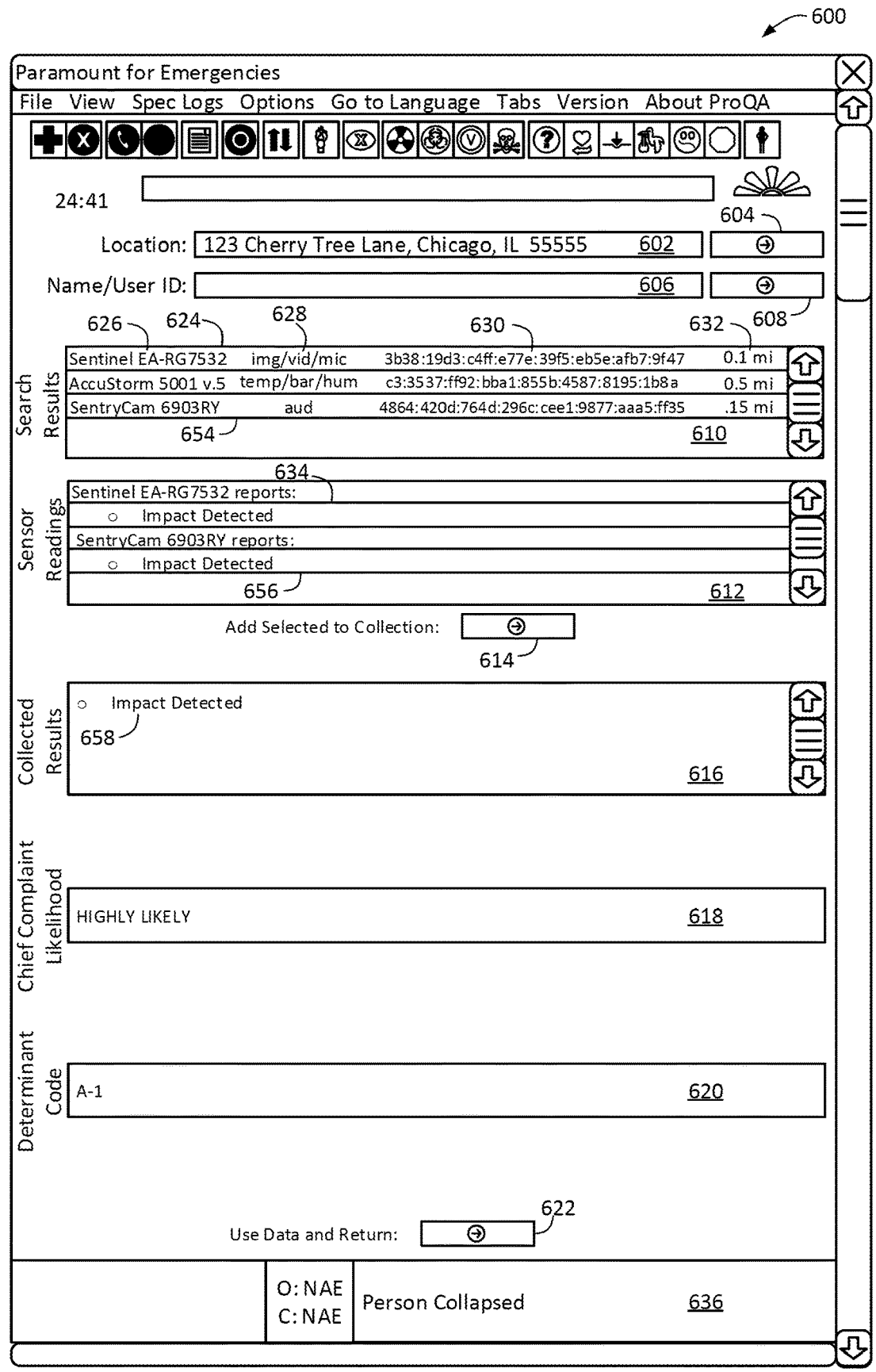

FIG. 6C illustrates that in some embodiments, it may be possible to use the external sensor data collected from two or more external sensors to determine a single data value for use in the emergency dispatch protocol 210. In the example of FIG. 6C, the process of FIG. 6A has been followed up to the filling of the search results field 610. In FIG. 6C, the search results field 610 also shows a third external device 654. The dispatcher 204 (or alternatively, the computing device 206) has recognized that both the first external device 624 and the third external device 654 are capable of providing audio data, and has selected both of these external devices 624, 654. The sensor readings field 612 then fills with both the first data value 634 (corresponding to the first external device 624) and the third data value 656 (calculated using data from the third external device 654). It may be that the dispatcher 204 and/or the computing device 206 select both of the first data value 634 and the third data value 656. The data values 634, 656 are both weighted and produced a result which is listed in the collected results field 616. The data values 634, 656 may confirm a result or the sensor data engine 240 may be programmed to resolve the difference between the two separate data values (e.g., by finding the average value) and move forward with that value. It is anticipated that 2, 3, 5, 19, or any other number of data values from any number of external devices 220 may be consolidated into a single data value in this way.

In the example of FIG. 6C, the consolidated data value 658 located in the collected results field 616 indicates that an impact is detected. The determinant code calculator may determine that the determinant code displayed in the determinant code field 620 is accurate or may modify the determinant code. The sensor data engine 240 determines that this information is consistent with the chief complaint of "Person Collapsed." The sensor data engine 240 accordingly may modify the chief complaint likelihood field 618 to reflect a "HIGHLY LIKELY" likelihood. The use of the "HIGHLY LIKELY" likelihood may reflect the fact that there are multiple data values consistent with the chief complaint (even though they are represented by only a single consolidated value).

FIG. 6D illustrates an alternative embodiment wherein the computing device 206 and the sensor data engine 240 operate to receive and process external device data and generate a confirmation without dispatcher 204 input. The determinant code calculator 216 also utilizes the eternal device data to confirm or modify the determinant code shown in the determinant code field 620. The user interface 680 includes many of the same fields previously discussed in reference to FIGS. 6A-6C, however dispatcher selection and input of detected external devices 220 and sensor data are not needed as the computing device 206 processes the external device data automatically. The user interface 680 may include a location field 602, an identification field 606, a search results field 610, a sensor readings field 612, a collected results field 616, a chief complaint likelihood field 618, a determinant code field 620, a chief complaint field 636, and a personal data field 650. The location field 602 and identification field 606 are populated automatically from sensor data and/or from the user interfaces 300, 400. Accordingly, the location search button 604 and identification search button 608 are not needed.

The sensor data engine 240 automatically identifies external devices 220 in the vicinity of the incident and populates the search results field 610. The external device information displayed in the search results field may be similar to or the same as that previously discussed. The dispatcher 204 does not select an external device 220. Thus, the external device 220 selection may be based on vicinity and whether the device is currently receiving relevant data. The sensor data engine 240 automatically lists the sensor data in the sensor readings field 612. The sensor data engine 240 then lists the collected results in the collected results field 616. As in previous embodiments, the chief complaint likelihood field 618 may indicate the likelihood of the chief complaint or emergency being confirmed. The determinant code field 620 may indicate a specific determinant code for emergency dispatch. The fields 610, 612, 616 may be provided in order to display the information to a dispatcher 204 or the fields 610, 612, 616 may be eliminated in part or in whole. Indeed, too much displayed information may be overwhelming to a dispatcher 204 and the dispatcher 204 may simply be provided with the results of a determinant code and a likelihood of the chief complaint or emergency being confirmed. In some embodiments, the chief complaint likelihood field 618 may also be eliminated as the emergency dispatch primarily relies on a determinant code. An accurate determinant code inherently reflects the likelihood of a chief complaint or emergency. Thus, the embodiment of FIG. 6D may provide for dispatcher interrogation of an information provider 214, but all external sensor data compilation and calculated results are performed automatically, without user intervention.

The personal information field 650 may be populated with information from a medical file that may be accessible to the computing device 206. The medical file may be resident on a portable electronic device carried by the victim or on an external database. In one embodiment, the personal information may be used by the sensor data engine 240 to determine the likelihood of a chief complaint or emergency. Thus, if the victim has a condition that renders the victim susceptible to falls, an increased probability of a fall is included when an impact is detected. As can be appreciated, access to the medical file is in compliance with governing regulations for patient privacy. The personal information may be sent automatically to emergency responders in conjunction with the emergency dispatch.

As disclosed herein, the computing device 206, and more specifically the sensor data engine 240, gathers multiple data sets from external devices 220 to arrive at a determinant code. The data sets may represent different types of received data. The determinant code expresses priority and a type of an emergency and is therefore distinguished from a generic alarm. As can be appreciated, the various data sets and determinant code provide a more sophisticated and reliable system than a conventional fire alarm that generates a generic alarm when a single metric threshold is reached.

FIG. 7 illustrates a user interface 700 corresponding to a determinant code calculator of an emergency dispatch protocol, according to an embodiment. The emergency dispatch protocol may be, for example, the emergency dispatch protocol 210. The user interface 700 may correspond to the determinant code calculator 216 of FIG. 2. The user interface 700 may operate on a computing device of a dispatch center (e.g., the computing device 206 of the dispatch center 202). The user interface 700 may be used by a dispatcher of a dispatch center (e.g., the dispatcher 204 of the dispatch center 202) when communicating with an information provider (e.g., the information provider 214).

The user interface 700 provides a summary field 702 that lists the answers to the pre-programmed inquiries as received by the dispatcher 204 (e.g., during the interrogation protocol 234).

The user interface 700 further provides a sensor data field 704 that displays the data values collected by the sensor data engine, in the manner described above in relation to FIGS. 6A-6D.

The user interface 700 further provides a send field 706 to send a determinant code to, for example, a CAD system, and a determinants field 708 which displays various determinant codes. The determinants field 708 lists various medical emergencies. Thus, the determinant code may indicate priority and a type of emergency, such as a medical emergency in the illustrated example. The determinant code is generated by a determinant code calculator 216 based on the answers to the pre-programmed inquiries, shown in the summary field 702 and the sensor data displayed in the sensor data field 704. Thus, in the given embodiment, the determinant code calculator 216 relies on both the responses by a caller and the external sensor data. The external sensor data used by the determinant code calculator 216 is listed in the sensor data field 704. The sensor data field 704 indicates that a victim is not breathing and this data may be received from a portable electronic device, such as a smartphone, smartwatch, or the like, carried by the victim. The sensor data field 704 also indicates that 33 people are in the area and this data may be received from a surveillance camera or the like.

The user interface 700 may further provide a chief complaint field 710. This field may present a deduced chief complaint in view of the data values found in the sensor data field 704. This likelihood may be/have been calculated by a sensor data engine (e.g., the sensor data engine 240), as described above.

In some embodiments, the likelihood of the chief complaint listed in field 710 (e.g., as calculated by the sensor data engine 240) may be used by the determinant code calculator 216 in determining a type of the emergency and/or a priority of a response. In some cases, if the likelihood of the chief complaint is "HIGHLY LIKELY" and/or "LIKELY," a type of the emergency and/or priority of the response that is consistent with the chief complaint and/or the answers to the pre-programmed inquiries from the summary field 702 may be determined. This may be because the likelihood of the chief complaint means that the dispatcher 204 can be confident that an emergency corresponding to the chief complaint is really occurring and/or that the embodiment of the interrogation protocol 234 used based on that chief complaint has, in all probability, gathered relevant information about the emergency.

Alternatively, if the likelihood of the chief complaint is "UNLIKELY" and/or "VERY UNLIKELY," a different type of emergency and/or priority of response (other than the type of emergency and/or priority of response that would be used based only on the chief complaint and/or the answers to the pre-programmed inquiries from the summary field 702) may be determined by the determinant code calculator 216. Once the potential unlikelihood of the chief complaint is established, the determinant code calculator 216 may analyze specific data values in the sensor data field 704 in order to determine a type of the emergency and/or priority of the response.

In some instances, the calculated likelihood of the chief complaint may mean that there is low confidence that the embodiment of the interrogation protocol 234 used has gathered relevant information about an emergency. For example, in a case where the chief complaint indicates that a person has a broken bone, but one or more data values in the sensor data field 704 report zero breaths per minute, the chief complaint likelihood field 710 may contain a value of "VERY UNLIKELY" (due to the fact that the chief complaint does not reflect any issues with breathing, which is more serious than a simple broken bone). In this case, the determinant code calculator 216 may determine the type of the emergency to be different and/or the priority of the response to be higher than it would otherwise be because of the data value from the sensor data field 704 that indicates that the person is not currently breathing.

In some instances, the calculated likelihood of the chief complaint may mean that there is low confidence that an emergency is actually occurring. For example, in a case where the chief complaint indicates that a person is viewing a riot in progress at a given location, but one or more data values in the sensor data field 704 report zero people at the relevant location, the chief complaint likelihood field 710 may contain a value of "VERY UNLIKELY" (due to the fact that the data values in the sensor data field 704 contradict the chief complaint). In this case, the determinant code calculator 216 may determine the type of the emergency to be different and/or the priority of the response to be lower than it would otherwise be because of the data value(s) in affirmative contradiction with the chief complaint.

In some instances, if the likelihood of the chief complaint is "UNKNOWN" (e.g., in cases where a chief complaint was never established or the collected data values were not useful to make a determination one way or the other), the determinant code calculator 216 may take into account only the answers to the pre-programmed inquiries from the summary field 702 in order to make a determination of a type of the emergency and/or a priority of a response.

After processing this information as described above, the determinant code calculator 216 generates a determinant code that indicates the priority of the response to the emergency and/or the type of the emergency. As can be expected, the data indicating that the victim is not breathing, sensor data field 704, will elevate the urgency and priority of the determinant code. Typically, a victim who is not breathing will take a determinant code to its highest level. Further, a crowd or numerous bystanders may also elevate a determinant code. In the given example, the sensor data field 704 indicates that there are 33 people nearby which may actually reduce the priority of the emergency.

The determinant codes may include priority values which may range, for example, from DELTA, for generally very serious emergencies, to ALPHA, for generally less serious emergencies (e.g., ALPHA—A, BRAVO—B, CHARLIE—C, and DELTA—D).

The determinant codes may include one or more type values which indicate the type of the emergency and which may be, for example, one or more numbers within a given range which are provided in the determinant code.

The determinant code may be provided to a CAD system (e.g., the CAD system 218) for processing. As shown in the send field 706, the user interface 700 lists the determinant code as 38-D-7. The dispatcher 204 may then click the send field 706, which acts as a confirmation to generate an emergency response. The computing device 206 of the emergency response system (e.g., the emergency response system 200) may then send the determinant code to the CAD system 218 to generate an emergency dispatch response according to the priority value and/or the type value found in the determinant code. In other words, when the determinant code is received by the CAD system 218, the response configuration (e.g., the vehicles, equipment, and personnel involved and/or the mode of response) may be dispatched as corresponding to the one or both of a priority value and/or a type value found in the determinant code.

As many reported incidents differ in their risks to life and/or property, emergency responses may be prioritized by the CAD system 218 according to need and available resources. Reported emergencies of a higher priority may accordingly be assigned a more immediate evaluation and response by the CAD system 218. If the emergency is of a low priority, then a lights-and-siren response may not be needed and may not be used, thereby increasing the safety of all those on the road and in the emergency vehicles. If the emergency dispatch protocol 210 determines that the emergency is not urgent and/or is not an event that merits an emergency response, a request may be sent to a non-emergency provider instead of dispatching an emergency response vehicle.

While many emergencies are not urgent, all responses can benefit from evaluation and the appropriate provision of post-dispatch or pre-arrival instructions. In some embodiments, prior to the arrival of the response, the emergency dispatch protocol 210 may provide instructions that are appropriate to instruct an information provider (e.g., the information provider 214) as to how they should respond to the emergency prior to the arrival of a dispatched response, such as to monitor the physical condition of a victim (e.g., the victim 212), to monitor the mental condition of a victim, to monitor any property damage that continues to occur, to stay on the line to be able to provide updates, etc. These instructions may be delivered from the dispatcher 204 to the information provider 214 using any of the communication methods (phone call, text message, etc.) described above.

In some embodiments, prior to the arrival of the response, the emergency dispatch protocol 210 may provide instructions that are appropriate to instruct the personnel that are part of the dispatched response on how to appropriately respond to the emergency. These instructions may be generated by the personnel instructions engine 217 (or another separate system) of the emergency dispatch protocol 210 and delivered to the personnel (e.g., via communication through the CAD system 218) that are to arrive as part of the dispatched response to the emergency. These instructions may be based on the type of the emergency and/or priority of the response that was calculated by the determinant code calculator 216. For example, if the type of the emergency is a choking emergency, instructions regarding how to perform the Heimlich maneuver (or other choking treatment) may be provided. As another example, if the priority of the emergency is high, a lights-and-sirens response may be instructed.

It is further contemplated that these instructions may further include instructions for the personnel that are part of the dispatched response that are based specifically on the gathered sensor data. For example, if the sensor data indicates that there are many people in the area where the response is needed, the instructions may include an instruction to reduce a speed of a vehicle to be used to effectuate the response once the vehicle arrives at the scene. As another example, if the sensor data indicates that a victim has no heartbeat, the instructions may include a method for performing CPR.

In some embodiments (e.g., involving a medical emergency of a victim 212), it is further contemplated that the determinant code calculator 216 may have received user data about the victim 212 (e.g., from the sensor data engine 240, in the manner described in FIG. 6B above). This information may be used to generate information and/or instructions specific to the victim 212 that are provided to the personnel that are being dispatched to respond to the emergency. Information about the victim 212 such as name, allergies, physiological characteristics, and known medical conditions and/or instructions on how to use/consider that information during the emergency response may help these personnel to more appropriately treat the victim 212 on site.

Figure 8:
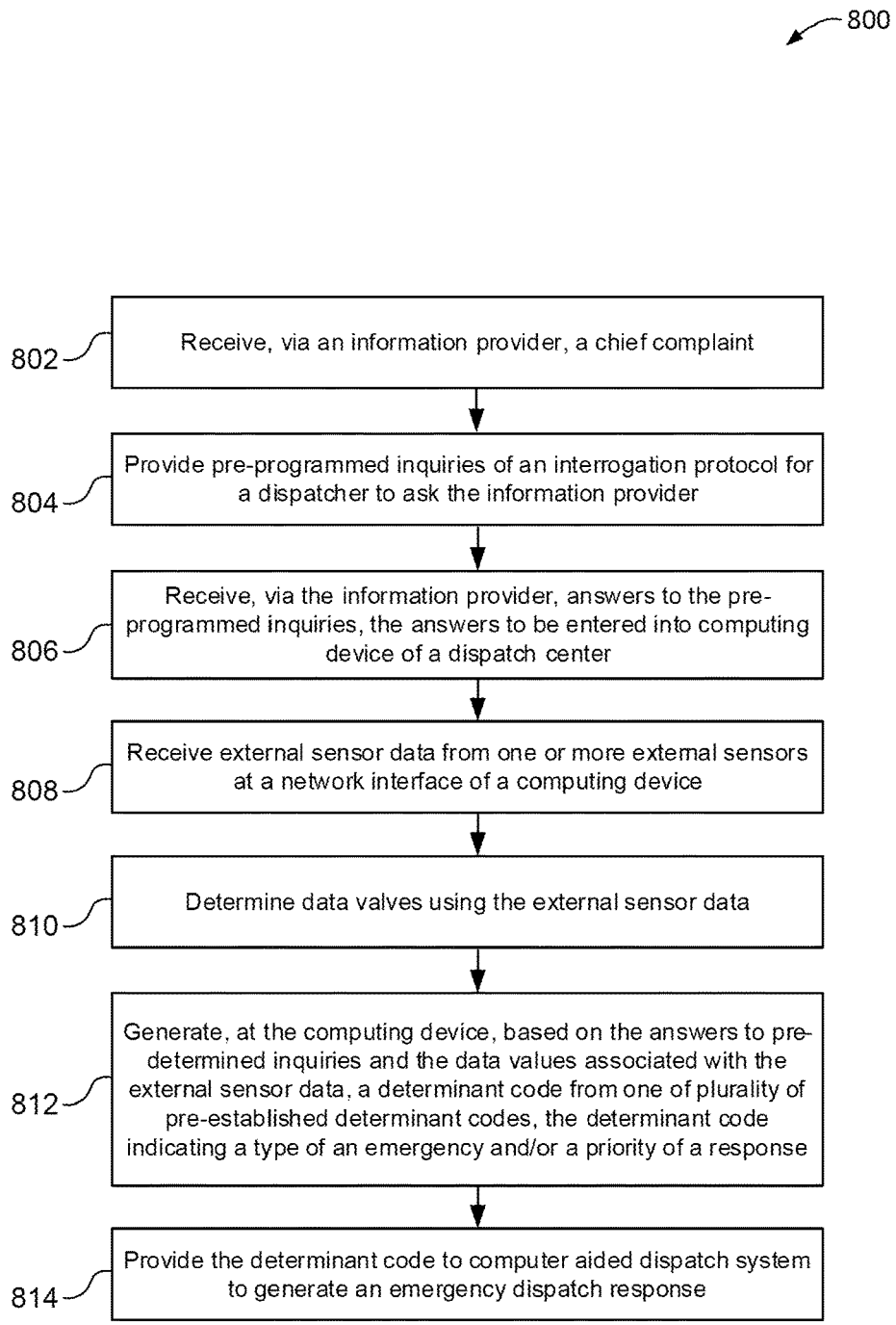
FIG. 8 illustrates a method to assist a dispatcher in responding to an emergency being reported by an information provider, according to an embodiment.

FIG. 8 illustrates a method 800 to assist a dispatcher in responding to an emergency being reported by an information provider, according to an embodiment. The method 800 includes receiving 802, via an information provider, a chief complaint.

The method 800 further includes providing 804 pre-programmed inquiries of an interrogation protocol for a dispatcher to ask the information provider.

The method 800 further includes receiving 806, via the information provider, answers to the pre-programmed inquiries, the answers to be entered into a computing device of a dispatch center.

The method 800 further includes receiving 808 external sensor data from one or more external sensors at a network interface of the computing device.

The method 800 further includes determining 810, at the computing device, using the external sensor data, data values associated with the external sensor data.

The method 800 further includes generating 812, at the computing device, based on the answers to the pre-programmed inquiries and the data values associated with the external sensor data, a determinant code from one of a plurality of pre-established determinant codes. The determinant code indicates a type of an emergency and a priority of a response. Thus, combining multiple data values from different types of sensors generates a priority for the response.

The method 800 further includes providing 814 the determinant code to a CAD system to generate an emergency dispatch response.

Figure 9A:
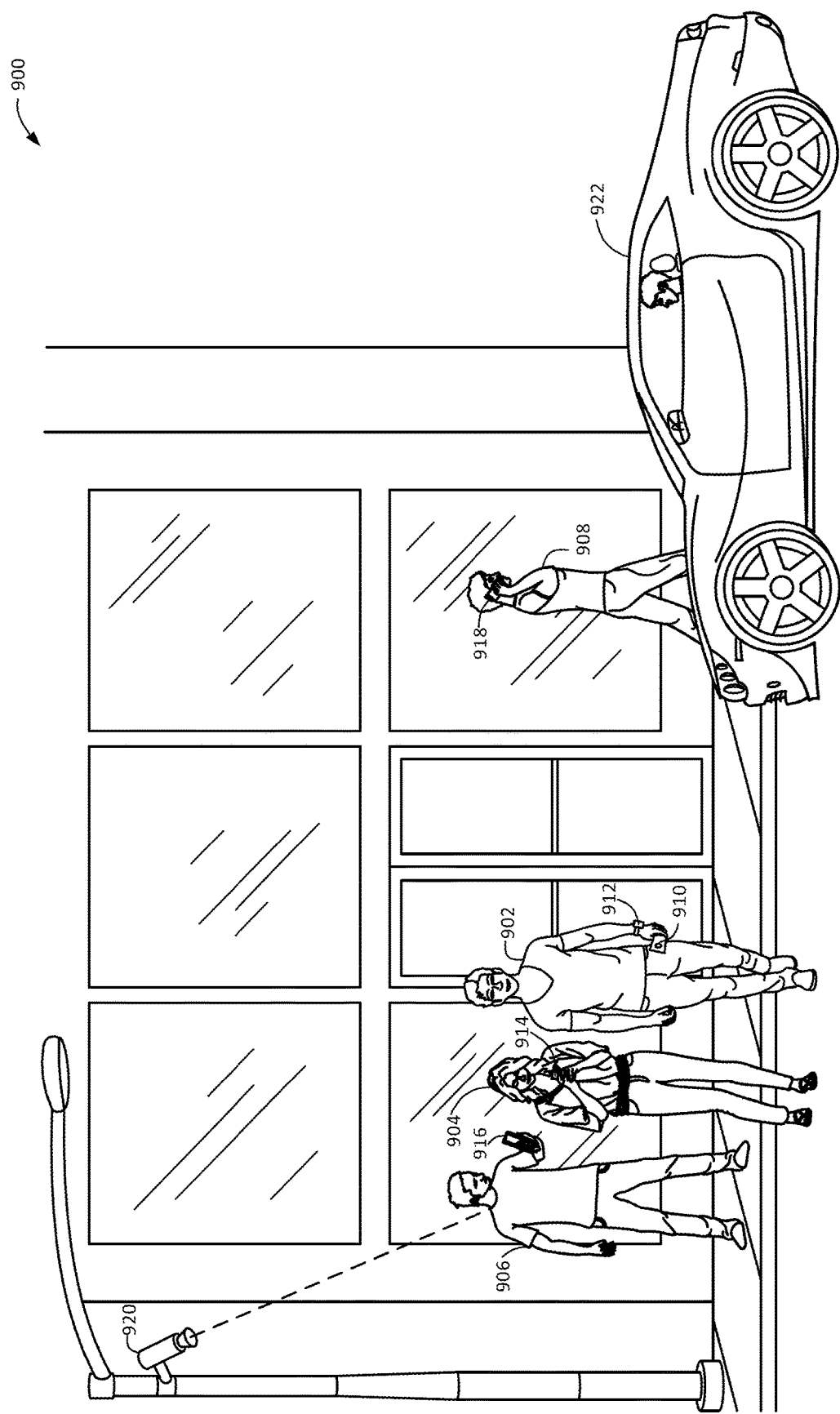

FIGS. 9A-9B illustrate a scenario 900 in which the systems and methods associated with an emergency dispatch protocol may be employed. The scenario 900 includes a victim 902, an information provider 904, a first bystander 906, and a second bystander 908. The victim 902 may be the user of a first smartphone 910 and a smartwatch 912. The information provider 904 may be the user of a second smartphone 914. The first bystander 906 may be the user of a third smartphone 916. The second bystander 908 may be the user of a fourth smartphone 918. The scenario 900 may further include a camera 920 and a motor vehicle 922. FIG. 9A illustrates a first portion of the scenario 900, where the victim 902 has yet to experience a medical incident.

FIG. 9B illustrates a second portion of the scenario 900, where the victim 902 has now experienced a medical incident. It may be, for example, that the victim 902 has experienced a cardiac arrest as they were crossing the street and has fallen to the ground. The information provider 904 is in the process of communicating with a dispatcher of a dispatch center (e.g., the dispatcher 204 of the dispatch center 202 of FIG. 2 via a phone call placed using the second smartphone 914).

This phone call may have arrived at the dispatch center 202 along with current location information and an external device identifier for the second smartphone 914. The dispatcher 204 may have already inquired of the information provider 904 as to the general nature of the incident in order to determine a chief complaint of the information provider 904, and accordingly filled in a chief complaint field, as described above. The dispatcher 204 may now be communicating pre-programmed inquiries of an interrogation protocol (e.g., the interrogation protocol 234) of an emergency dispatch protocol (e.g., the emergency dispatch protocol 210) to the information provider 904, and the information provider 904 may be communicating answers to those pre-programmed inquiries back to the dispatcher 204, who is entering them into a computing device (e.g., the computing device 206 of the dispatch center 202) in the manner described above.

It may also be that after the information provider 904 began communication with the dispatcher 204, the dispatcher 204 (or, alternatively, the computing device 206) engaged the sensor data engine 240. The sensor data engine 240 may query the second smartphone 914 using the external device identifier that was provided to the computing device 206 along with the call data, as described above. In response to this query, the second smartphone 914 may provide the computing device 206 of the dispatch center 202 with accelerometer data indicating that the second smartphone 914 is currently not moving.

The sensor data engine 240 may also communicate with an external device database (e.g., the external device database 222) in order to identify external devices other than the second smartphone 914 from which relevant sensor data may be retrieved. For example, a username of the victim 902 that is associated with the first smartphone 910 and/or the smartwatch 912 may be provided to the computing device 206. It may be that the information provider 904 was aware of this username and was able to relay it to the dispatcher 204. Alternatively, the username of the victim 902 may have been determined at the second smartphone 914 by communication (e.g., Bluetooth, NFC) between the second smartphone 914 and either of the first smartphone 910 and/or the smartwatch 912 of the victim 902, and subsequently sent from the second smartphone 914 to the computing device 206. The username of the victim 902 may be sent by the computing device 206 of the dispatch center 202 to the external device database 222 in order to retrieve the external device identifiers of the external devices associated with that username (including the first smartphone 910 and/or the smartwatch 912). Alternatively, location-based methods (described elsewhere) may be used to identify the external device identifiers of the first smartphone 910 and/or the smartwatch 912.

The sensor data engine 240 may query the first smartphone 910 and/or the smartwatch 912 using these external device identifiers. In response to a query to the first smartphone 910, the first smartphone 910 may provide the computing device 206 of the dispatch center 202 with accelerometer data indicating that the first smartphone 910 has recently undergone a sudden downward movement of a range between three and four feet. In response to a query to the smartwatch 912, the smartwatch 912 may provide the computing device 206 of the dispatch center 202 with heart rate data indicating that a detected heart rate of the victim 902 is at zero BPM.

Either of the first smartphone 910 and/or the smartwatch 912 may provide the sensor data engine 240 with the option to also retrieve and use user data about the victim 902 that may have been stored within those devices (see FIG. 5B and related discussion).

The sensor data engine 240 may continue to communicate with the external device database 222 in order to identify further, additional external devices. A location relevant to the emergency may be provided to the computing device 206 of the dispatch center 202. For example, the location data from the second smartphone 914 (the smartphone being used by the information provider 904) may be present at the computing device 206, as discussed above. Alternatively, the information provider 904 may provide relevant location data for the dispatcher 204 to manually enter into the computing device 206. The location relevant to the victim 902 may be sent by the computing device 206 of the dispatch center 202 to the external device database 222 in order to retrieve the external device identifiers of any external devices that are near that location. This query may return the external device identifiers of the third smartphone 916, the fourth smartphone 918, the camera 920 and/or the motor vehicle 922.

The sensor data engine 240 may then query the third smartphone 916, the fourth smartphone 918, the camera 920 and/or the motor vehicle 922 using these external device identifiers. In response to a query to the third smartphone 916, the third smartphone 916 may provide the computing device 206 of the dispatch center 202 with still image data that the sensor data engine 240 subsequently analyzes. This analysis may allow the sensor data engine 240 to determine that the still image data indicates that there is one person lying on the ground near the location. In response to a query to the fourth smartphone 918, the fourth smartphone 918 may provide the computing device 206 of the dispatch center 202 with raw audio data that the sensor data engine 240 subsequently analyzes. This analysis may allow the sensor data engine 240 to determine that the raw audio data indicates that there is a noise level of greater than 80 decibels near the location. In response to a query to the camera 920, the camera 920 may provide the computing device 206 of the dispatch center 202 with formatted video data that the sensor data engine 240 subsequently analyzes. This analysis may allow the sensor data engine 240 to determine that the video data indicates that there is a grouping of four people near the location. In response to a query to the motor vehicle 922, the motor vehicle 922 may provide the computing device 206 of the dispatch center 202 with speed history data, which the sensor data engine 240 subsequently analyzes. This analysis may allow the sensor data engine 240 to determine that the speed history data is consistent with a binary indication to the affirmative that a recent sharp deceleration has occurred.

In addition to or in the alternative, the smartwatch 912 or the first smartphone 910 may sense the fall or change in the victim's breathing. As such, the smartwatch 912 and/or the first smartphone 910, in combination or independently, are configured with biosensors to receive physiological data from a victim 902. The smartwatch 912 or first smartphone 910 may automatically initiate communication with the computing device 206 independent of user operation. Thus, communication of the smartwatch 912 and first smartphone 910 with the computing device 206 does not depend on the smartphones 914, 916. The smartwatch 912 and first smartphone 910 may provide data values sufficient to indicate that the victim 902 has collapsed and that the victim 902 may have physiological impairment such as agonal breathing, irregular heartbeat, etc. Thus, the smartwatch 912 and first smartphone 910 may provide data values to enable generation of a determinant code and an emergency dispatch.

The sensor data engine 240 may use these data values in the manner described above and provide the data values to the determinant code calculator 216. The determinant code calculator 216 then determines a determinant code indicative of the emergency level and priority.

Figure 10:
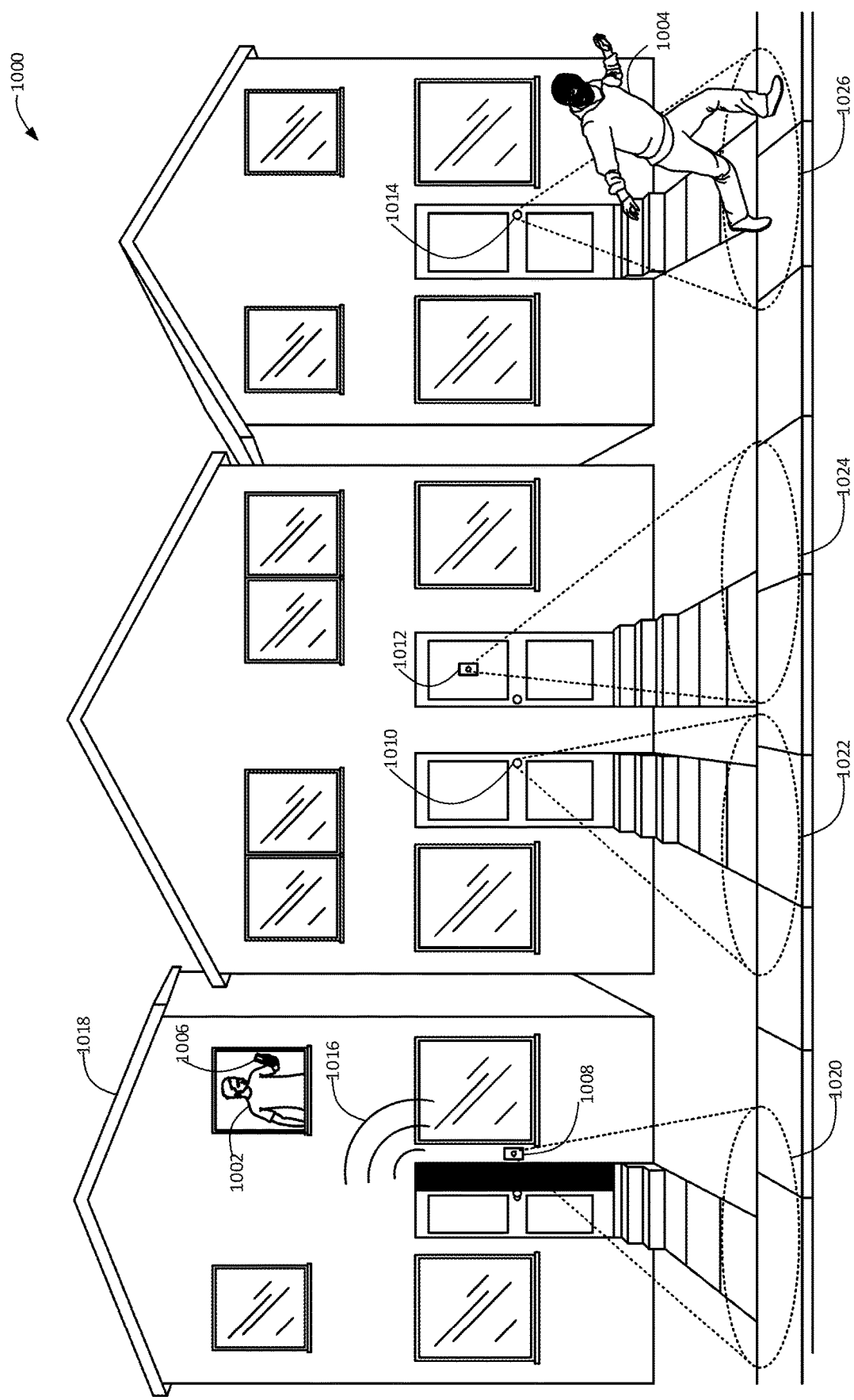
FIG. 10 illustrates a scenario in which the systems and methods associated with an emergency response system may be employed.

FIG. 10 illustrates a scenario 1000 in which the systems and methods associated with an emergency dispatch protocol may be employed. The scenario 1000 includes an information provider 1002 and a suspect 1004. The information provider 1002 may be the user of a first smartphone 1006. The scenario 1000 may further include the first security platform 1008, the second security platform 1010, the third security platform 1012, and the fourth security platform 1014. In the scenario 1000, the suspect 1004 has inadvertently made a loud noise 1016 within the dwelling 1018 while trespassing therein and has subsequently escaped from the dwelling 1018 and passed through the various monitoring regions 1020-1026, each respectively associated with the security platforms 1008-1014.

In response to the noise 1016, the information provider 1002 has initiated communication with a dispatcher (e.g., the dispatcher 204 of FIG. 2) at a dispatch center via a text message (e.g., the dispatch center 202, including all its components as described above). The text message may be received at the dispatch center 202 along with location information and an external device identifier for the first smartphone 1006, as described above. The receipt of this text message may cause the dispatcher 204 to enter into a case entry protocol and ask as to the general nature of the incident, and accordingly indicate a chief complaint in the computing device 206, as described above. Once this is complete, the dispatcher 204 may proceed to an interrogation protocol (e.g., an interrogation protocol 234) in order to pose and receive answers to pre-programmed inquiries from the information provider 1002, as described above.

The sensor data engine 240 may be automatically engaged by the computing device 206 of the dispatch center 202. The sensor data engine 240 may immediately query the first smartphone 1006 for any data (sensor data, user data) it may have using the external device identifier provided with the incoming text message. In response to this query, the first smartphone 1006 may provide the computing device 206 of the dispatch center 202 with audio data including a binary indication that a loud noise was recently detected by the smartphone 1006.

Further, the computing device 206 may also have immediately sent the location of the first smartphone 1006 to an external device database (e.g., the external device database 222) in order to retrieve the external device identifiers of any external devices that are near that location. This query may return the external device identifiers of the first security platform 1008, the second security platform 1010, the third security platform 1012, and/or the fourth security platform 1014. The sensor data engine 240 may then query the first security platform 1008, the second security platform 1010, the third security platform 1012, and/or the fourth security platform 1014 using their external device identifiers. Each of these queries may return motion sensor data in the form of a binary indication that they have detected large amounts of motion within the last few minutes.

The sensor data engine 240 may use received data values in combination to enhance the communication from the information provider 1002 to the dispatcher. The sensor data engine 240 may recognize that the various binary indications from multiple security platforms 1008-1014 corroborate each other. The determinant code calculator 216 may take the data values, binary indications, and corroboration in determining a determinant code indicative of an emergency level and priority. The sensor data engine 240 may also compile the received data values from the security platforms 1008-1014 and determine a direction of the suspect 1004. This information may be provided to the dispatcher and the emergency responders.

While the information provider 1002 may initiate communication, the security platforms 1008-1014 may also automatically initiate the first communication with the computing device 206 and send data values to the sensor data engine 240. The data values may enhance a communication subsequently received from the information provider 1002.

The sensor data engine 240 may receive various types of data values to determine the priority of an emergency. Data values may indicate trouble with several victim/patient vitals such as breathing, circulation, oxygen saturation, heart rate, blood pressure, pulse, etc. Based on these data values, a determinant code and/or multiple chief complaints may be apparent or likely. The sensor data engine 240 may prioritize the likely emergency based on urgency in order to stabilize the vitals and optimize life preservation. For example, data values may indicate a slow heart rate and also agonal breathing. While the sensor data engine 240 may determine that there are multiple emergencies or chief complaints, the sensor data engine 240 will prioritize the agonal breathing and identify this as the chief complaint. In another example, a caller may indicate that a victim is having abdominal pains. However, data values from a physiological sensor may indicate that the victim has extreme blood circulation trouble. The chief complaint may rather be prioritized as a blood circulation emergency. The prioritized chief complaint may be determinative in sending an appropriate emergency response unit that includes trained personnel and equipment.

The sensor data engine 240 may also conclude that there are chief complaints of a different emergency nature, such as fire, medical, and/or police in the same vicinity. For example, data values from a smartphone may indicate that a person has fallen. However, the interrogation protocol 234 indicates that the person is alert and breathing. At the same time, data values from a thermal sensor may indicate that there is a fire nearby. The sensor data engine 240 may prioritize the chief complaint as a fire emergency rather than a medical emergency.

In another example, data values from security sensors may indicate a break-in of a commercial or residential building and theft. Data values from a thermal sensor may also indicate that the building is on fire. The sensor data engine 240 may prioritize the chief complaint as a fire emergency rather than a police emergency. A fire emergency prioritization may be even more likely depending on the time elapsed from the possible break-in.

In yet another example, the sensor data engine 240 may receive data values indicative of a car theft and an accident of the same car. Based on the severity of the accident, the sensor data engine 240 may determine that the chief complaint is a medical emergency rather than a police emergency. Nevertheless, both complaints may be indicated and appropriate emergency responders dispatched.

As another example, the sensor data engine 240 may receive data values from one or more security sensors of an armed assailant. The data values may indicate a break-in and a gunshot. At the same time, the sensor data engine 240 may receive data values indicative of a victim falling and victim blood loss. The sensor data engine 240 may prioritize the chief complaint or emergency as a police emergency rather than a medical emergency. This is even more likely if the data values from security sensors indicate that the armed assailant is still nearby. As can be appreciated, both complaints may still be indicated and appropriate emergency responders dispatched.

Besides corroborating the interrogation protocol, the sensor data engine 240 may use the data values to determine the likelihood of contradiction. Thus, while a caller may verbally communicate that a victim/caller is having a heart attack, received data values may indicate otherwise. As an additional example, a caller may state that the caller smells smoke, but all thermal sensors may indicate otherwise. As such, the sensor data engine 240 may provide the emergency dispatch protocol 210 with an indication that the chief complaint is unlikely or highly unlikely. The emergency dispatch protocol 210 may display "UNLIKELY" or "HIGHLY UNLIKELY" in any of the above-mentioned user interfaces to so indicate to the dispatcher 204. The dispatcher 204 may have the option of overriding the chief complaint, continuing with a follow-up protocol to further interrogate the caller, or continuing with the emergency dispatch and inform the emergency dispatch unit that there is a probability of a false emergency.

The sensor data engine 240 may also receive data values from different sensors that both corroborate and contradict a chief complaint and establish a determinant code. The sensor data engine 240 may weigh the data values (equally or otherwise) to determine the likelihood of a chief complaint. For example, multiple thermal sensors in a building may indicate a fire emergency. However, a single thermal sensor, in the same building, may not indicate a fire emergency. Based on the totality of the sensor data, the sensor data engine 240 may determine the likelihood of a fire emergency.

Figure 11:
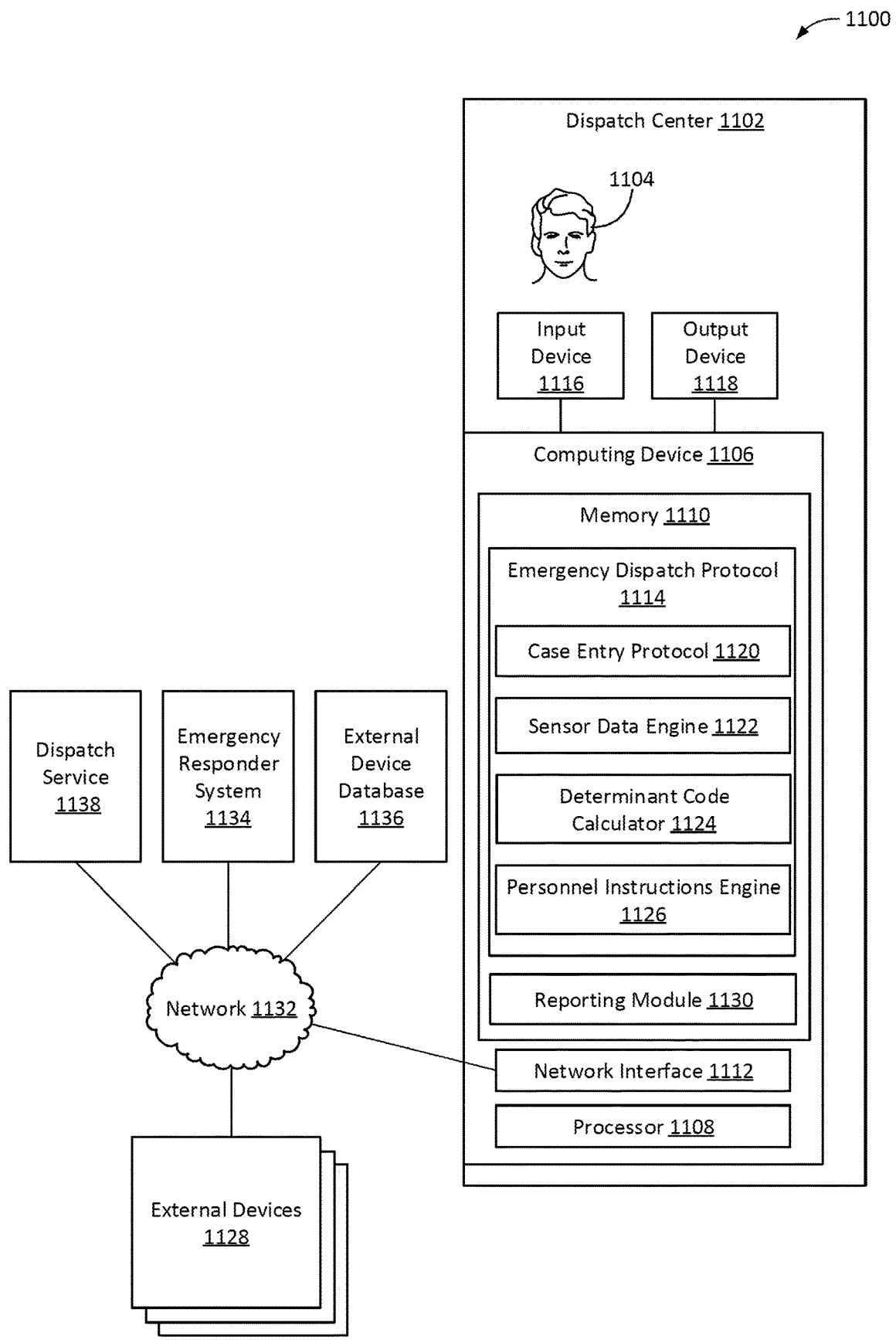
FIG. 11 illustrates an emergency response system in accordance with an alternative embodiment.

FIG. 11 illustrates an alternative embodiment of an emergency response system 1000. The emergency response system 1100 primarily relies on data from IOT devices rather than an information provider conveying information to a dispatcher. The previously discussed emergency response system 200 illustrates a system with a dispatcher that actively engages an information provider with pre-programmed inquiries to arrive at a determinant code. The system 200 receives and analyses data values from external devices to corroborate an emergency and calculate a determinant code. The emergency response system 1100 may receive and analyze data values from external devices and provide a response without a dispatcher actively engaging in dialog with an information provider. In so doing, the emergency response system 1100 confirms the likelihood of an emergency level and a determinant code based on data values from IOT devices.

The emergency response system 1100 includes a dispatch center 1102. A dispatcher 1104 may be present at the dispatch center 1102 to operate or monitor a computing device 1106 having a processor 1108, a memory 1110, and a network interface 1112. The computing device 1106 may also operate without a dispatcher 1104 present or the dispatcher 1104 may work remotely. As such, the dispatcher 1104 may login to access the computing device 1106 from a remote location. As the dispatcher 1104 may not be actively involved in individual emergency response dispatches, the dispatcher 1104 may be alternatively identified as a computer operator. Indeed, a dispatcher/computer operator 1104 may be responsible to monitor a plurality of computing devices either on-site or remotely.

The memory 1110 may be provided with an emergency dispatch protocol 1114 at least partially stored thereon to enable automated emergency response dispatch based only or at least primarily on TOT devices. The computing device 1106 may include an input device 1116 and an output device 1118 to allow a dispatcher 1104 to interface with the computing device 1106. However, the computing device 1106 may operate and generate an emergency response without a dispatcher 1104.

The emergency dispatch protocol 1114 may be initiated when the computing device 1106 receives information from one or more TOT devices. The responses and data values are processed according to pre-determined logic to determine a determinant code to provide an emergency response. The emergency dispatch protocol 1114 facilitates uniform and consistent gathering of information relating to the emergency. The dispatch may be determined, in part, through a system of logically assigning determinant codes as the protocol progresses (i.e., traverses) through the logic tree. The logic tree of the emergency dispatch protocol 1114 may be provided across multiple sub-components of the emergency dispatch protocol 1114, including, but not limited to, a case entry protocol 1120, a sensor data engine 1122, a determinant code calculator 1124, and/or a personnel instructions engine 1126. The computing device 1106 may include the case entry protocol 1120 which initially sets up the case for the emergency event.

The computing device 1106 may further include the sensor data engine 1122. The sensor data engine 1122 may be used by the emergency dispatch protocol 1114 to communicate with and receive external sensor data from the one or more external devices 1128 such as IOT devices. This external sensor data may be used by the emergency dispatch protocol 1114 to confirm the existence of an emergency, the type of emergency, the priority, and the appropriate response. For improved accuracy and reliability, information from more than one external device 1128 may be used. The sensor data engine 1122 may determine, based on the received external sensor data, the likelihood of an actual emergency or a chief complaint.

The sensor data engine 1122 may use data values arriving from multiple external devices to determine the probability of multiple chief complaints and prioritize a chief complaint. For example, physiological sensors may send data values indicative of victim vitals such as breathing, circulation, oxygen saturation, heart rate, blood pressure, pulse, etc. The sensor data engine 1122 may determine that a victim has multiple chief complaints and the complaints may be prioritized in order to stabilize the victim's vitals. For example, data values may indicate obstructed breathing and a rapid heart rate. The sensor data engine 1122 may prioritize the obstructed breathing as the chief complaint. The prioritized chief complaint may be determinative in sending an appropriate emergence response unit including trained personnel and equipment.

As in the embodiment of the emergency response system 200, the sensor data engine 1122 may also conclude that there are chief complaints of different emergency natures, such as fire, medical, and/or police in the same vicinity. The sensor data engine 1122 may indicate that there are multiple complaints but may also prioritize a chief complaint based on a number of factors. For example, sensor data from a security sensor may indicate a break-in, theft, and departure of an assailant. However, sensor data from a physiological sensor may indicate that a victim on the scene is in urgent need of vitals stabilization. The chief complaint may be a medical emergency rather than a police emergency. Nevertheless, both complaints may be indicated and appropriate emergency responders dispatched. Other examples include those previously mentioned in reference to the emergency response system 200.

The sensor data engine 1122 may also receive data values from different sensors that both corroborate and contradict a chief complaint or emergency. The sensor data engine 1122 may weigh the data values based on a number of factors to determine the likelihood of a chief complaint.

The emergency dispatch protocol 1114 includes and operates a determinant code calculator 1124 to calculate a determinant code from the information received from the external devices 1128. The determinant code calculator 1124 may calculate a determinant code that indicates a priority of a response and the type of the emergency.

The emergency dispatch protocol 1114 includes and operates a personnel instructions engine 1126 to provide instructions that are appropriate to instruct the personnel that are part of the dispatch on how to appropriately respond to the emergency. The instructions may be based on information about the emergency from either or both of the determinant code calculator 1124 and the sensor data engine 1122 and delivered to the emergency response personnel.

The computing device 1106 may include a reporting module 1130 to statistically measure the performance of the dispatch center 1102. The statistics may include compliance rates, communication processing statistics, and emergency identification accuracy. Once the dispatch is generated, the emergency dispatch protocol 1114 may close the case, and a case summary may be saved. The case summary may be retrieved later by the reporting module 1130 for review and/or analysis. The reporting module 1130 may determine statistics from the case summaries and/or while the cases are open.

The network interface 1112 of the computing device 1106 may be connected to a network 1132. The computing device 1106 may use the network interface 1112 to send information to and receive information from the external devices 1128, the emergency responder system 1134, an external device database 1136, and a dispatch service 1138.

The network 1132 may facilitate information transfer between the computing device 1106 and one or more external devices 1128. This information may include external sensor data (whether raw or formatted) that is being transferred from one of the external devices 1128 to the computing device 1106.

The network 1132 may facilitate information transfer between the computing device 1106, the emergency responder system 1134, and one or more emergency response vehicles and/or other units that may be dispatched to the location of an incident. The emergency responder system 1134 may be used by the computing device 1106 to initiate, track, and/or allocate emergency response resources. The emergency responder system 1134 may operate in whole or in part on a separate computer in communication with the computing device 1106.

The network 1132 may facilitate information transfer between the computing device 1106 and the external device database 1136. Information that may be transferred by the external device database 1136 to the computing device 1106 includes information about the geographic location of one or more of the external devices 1128, information about an association between a person and one or more of the external devices 1128, an external device identifier associated with one or more of the external devices 1128, and information about the type(s), format(s), and/or quality(ies) of external sensor data that may be provided by one or more of the external devices 1128.

The network 1132 may facilitate information transfer between the computing device 1106 and a dispatch service 1138. The dispatch service 1138 may provide services for less urgent responses. The dispatch service 1138 may communicate with one or more response vehicles and/or other units that may be dispatched to the location of an incident. For example, a low priority medical response may determine that a patient should receive a pandemic test within the next 24 hours. As another example, a medical response may be to transfer a patient to or between medical facilities. Indeed, for patient transfers, the dispatch service 1138 may include services operated by ride share applications commonly known in the art. By way of example, if a patient is in need of non-emergency medical attention, and the patient is unable to drive, then a dispatch service 1138 may send transport to the patient. Indeed, the transport may even be a driverless vehicle.

The emergency responder system 1134 may be used by the computing device 1106 to initiate, track, and/or allocate dispatch resources. The dispatch service 1138 may operate in whole or in part on a separate computer in communication with the computing device 1106.

Figure 12:
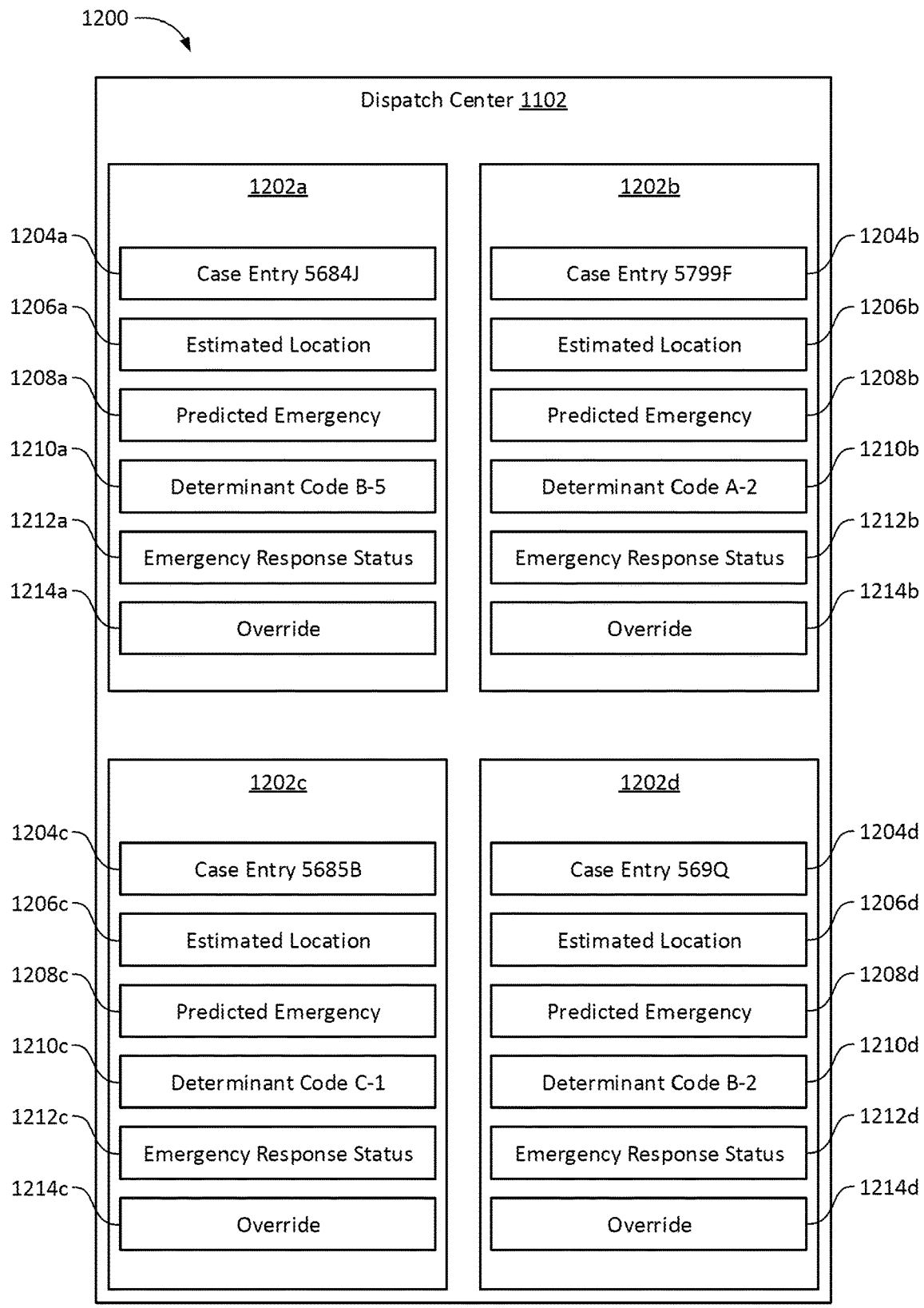
FIG. 12 illustrates a user interface in accordance with the emergency response system of FIG. 11.

FIG. 12 illustrates an embodiment of a user interface 1200 for the emergency dispatch protocol 1014 of the computing device 1106. The user interface 1200 may allow a computer operator 1104 to view the status of one or more emergency dispatches 1202a-d while the dispatches are being processed. One of skill in the art will appreciate that the displayed format may vary substantially based on design preferences and presentation priority.

A dispatch 1202a-d may include a case entry identification 1204a-d that is specific and unique to the corresponding dispatch 1202a-d. All information relating to the dispatch 1202a-d may be linked to the case entry identification 1204a-d. The case entry identification 1204a-d is generated by the case entry protocol 1120 and may include a designation that links the dispatch 1202a-d to the computing device 1106. The reporting module 1130 may rely on the case entry identification 1204a-d for statistical evaluation and storage of the processed dispatch 1202a-d. The exact numbering and/or lettering of the case entry identification 1204a-d may vary according to any desired protocol.

The dispatch 1202a-d may also include an estimated location 1206a-d which may be a graphic illustrated as a tab, icon, or the like. The estimated location 1206a-d may be calculated by the sensor data engine 1122 based on the data received from one or more external devices 1128. An external device 1128 may have a GPS or may be designated a geographical location upon installation. Location data may be sent from the external device 1128 to the computing device 1106 which is then processed and an estimated location is assigned. The estimated location 1206a-d may designate a location directly on the graphic. Alternatively, the graphic may include a clickable link which allows for user selection to then display a graphical location.

The dispatch 1202a-d may include a predicted emergency 1208a-d which is a graphic, such as an icon, which lists an emergency. The emergency nomenclature may vary as desired. The predicted emergency 1208a-d may be calculated by the determinant code calculator 1124 based on the information compiled by the sensor data engine 1122. The predicted emergency 1208a-d may display the emergency or provide a clickable link which then displays the emergency or directs the user to a display with the emergency.

The dispatch 1202a-d may include a determinant code 1210a-d, which displays the determinant code calculated by the determinant code calculator 1124.

The dispatch 1202a-d may further include an emergency response status 1212a-d, which may display one or more graphics indicating the processing of an emergency response. The emergency response status 1212a-d may indicate: the computing device 1106 has just received external sensor data indicative of an emergency; the computing device 1106 is processing the external sensor data; an emergency has been determined; a dispatch request has been sent to the emergency responder system 1134; an emergency response has been dispatched; an emergency response has arrived on the emergency scene; and an emergency response has been completed. The different status stages, designations; and graphics may vary as desired. For example, the graphics may provide color coding or a bar graph to indicate the progress of the dispatch.

The dispatch 1202*a-d* may further include an override 1214*a-d* to allow a computer operator 1104 to intervene in the emergency dispatch process. The override 1214*a-d* may allow a computer operator 1104 to change the estimated location, predicted emergency, or determinant code, or even terminate the entire emergency dispatch process. Upon selecting the override 1214*a-d*, the override 1214*a-d* may provide a prompt as to whether the emergency dispatch process is to be terminated or whether a dispatch value is to be changed. Responsive to the inputted selection, the override 1214*a-d* may then allow the computer operator 1104 to terminate or alter dispatch values. The computer operator 1104 may be able to view one or more dispatches 1202*a-d* on a single screen and override any of the dispatches 1202*a-d* that are in progress.

Figure 13:
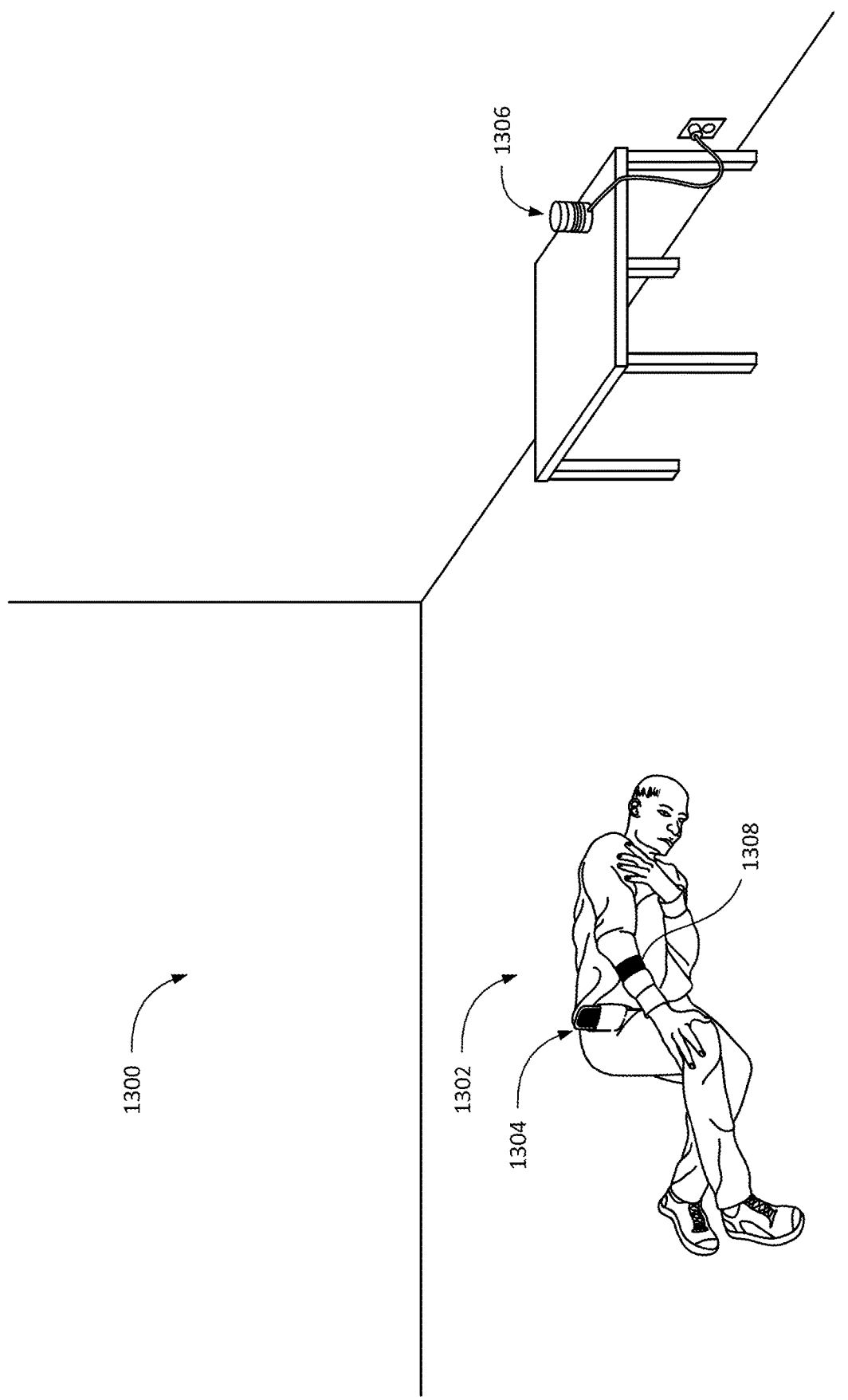
FIG. 13 illustrates a scenario in which the systems and methods associated with an emergency response system may be employed.

FIG. 13 illustrates a scenario 1300 in which the systems and methods associated with an emergency dispatch protocol may be employed. In the given scenario, a human user does not actively provide information to a dispatch center or actively request an emergency response. It is the coordinated data received from the external devices 1128, the automated processing by the computing device 1106, and the interface with the emergency responder system 1134 that provides an emergency response. Thus, no human agent is involved in the accumulation of data relating to the emergency, the determinant value generation, and the instructions to dispatch an emergency response unit that may include human emergency responders.

A user 1302 may have a smartphone 1304 or other portable electronic device on the user's person. The smartphone 1304 may include a dispatch application which is in communication with the computing device 1106. The dispatch application may enable the smartphone 1304 to operate as an external device 1028 to send sensor data to the computing device 1106 for emergency dispatch calculation. The smartphone 1304 may include an accelerometer, among other sensors, to determine the movement of the user 1302. When a user 1302 suddenly falls, the smartphone 1304 may send sensor data indicative of a collapse. An interior sensor 1306, such as an Amazon Echo® or a Google Dot®, may be in proximity to the user 1302 upon the collapse incident and record audio and/or vibration indicative of the collapse.

The emergency dispatch protocol 1114 may receive sensor data from the smartphone 1304 and the interior sensor 1306 to determine an emergency. The sensor data from just the smartphone 1304 may not be sufficient to confirm an emergency. For example, the user 1302 may have simply dropped the smartphone 1304. However, corroborating sensor data provided by the interior sensor 1306 may confirm a body collapse rather than a smartphone 1304 simply hitting the floor. The emergency dispatch protocol 1114 weights the sensor data provided by the smartphone 1304 and interior sensor 1306 and determines the existence of an emergency, and, if present, calculates a determinant code and communicates with the emergency responder system 1134 to generate an emergency response. While urgent, the priority assigned to a user fall may not be as high as other emergency situations, such as agonal breathing or an active assailant. Thus, the determinant value will not be as high.

Emergency calculation and assignment of a determinant code may be further impacted by a user's history. The dispatch application may include user medical data including physiological data, the user's personal medical history, and emergency contact information. The medical history may include user diagnoses, past and present prescriptions, and prior medical emergencies. The prior medical emergencies may include whether the user has had one or more previous collapses. If so, evidence of past events will weight in favor of an emergency incident. Furthermore, past medical events suggesting a likelihood of a user collapse, such as strokes, heart attacks, and the like, will also weight in favor of an emergency incident. As can be appreciated, the user medical data may be stored, in whole or in part, on the external device database 1136, alternative database or server, or on the computing device 1106 itself.

Upon determination of an emergency, the emergency responder system 1134 receives the determinant code and a user location. The user location may be confirmed by both the smartphone 1304 and the interior sensor 1306. The emergency dispatch protocol 1114 may also send a text message, email, or the like to the user's emergency contact provided in the user medical data. Thus, simultaneous with an emergency dispatch, a medical professional, family member, and/or friend may be informed of the emergency. The reporting module 1130 may record the emergency and the associated dispatch, and the emergency may be included in an updated user medical data. Thus, the next time a similar incident occurs, the past incident will factor in the determination of the emergency.

A collapsed user 1302 may be unconscious or otherwise incapacitated and unable to audibly operate the smartphone 1304 or the interior sensor 1306, or communicate with a dispatcher. Thus, the emergency response system 1100 enables emergency dispatch without active human interrogation to thereby expedite the emergency response process.

In an additional embodiment, a user 1302 may also have a biosensor 1308 in proximity or attached to the user 1302 to measure and generate user vital data. The biosensor 1308 may measure certain metrics such as pulse rate, pulse oximetry, and/or cardiac electrical potential waveforms. The generated vital data in conjunction with data from the smartphone 1304 and the interior sensor 1306 greatly improves an accurate prediction of an emergency. Thus, data indicative of a loud sound (generated by the interior sensor 1306), data indicative of a user 1302 not moving for 10 minutes (generated by the smartphone 1304), and data indicative of a user 1302 having a low pulse rate and/or other irregular heart activity (generated by the biosensor 1308), in combination, affirms the likelihood of an emergency far more than a single data indicator. Multiple sensors are employed to independently affirm or deny an emergency to thereby greatly increase the accuracy and reliability of the entire dispatch system.

Figure 14:
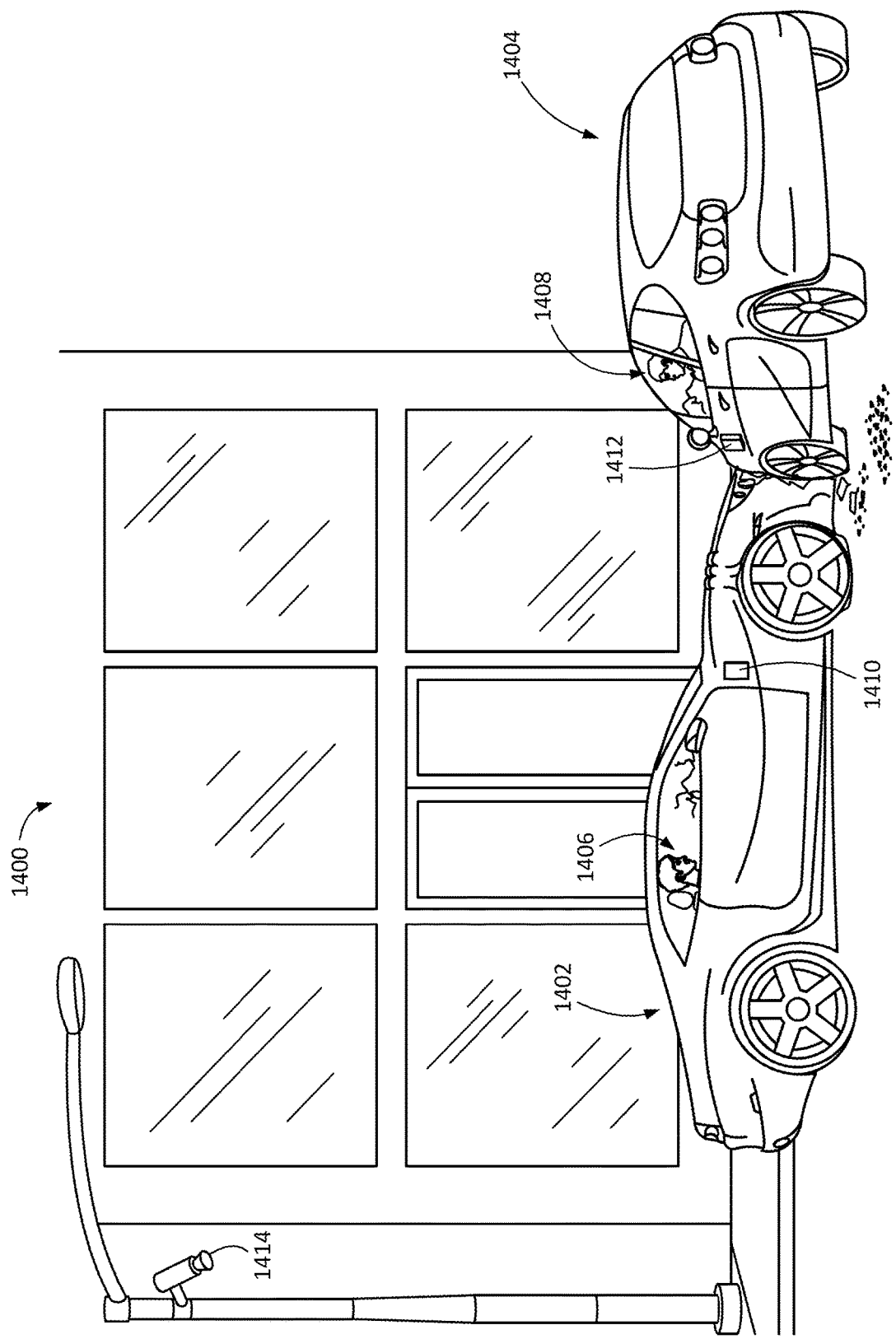
FIG. 14 illustrates a scenario in which the systems and methods associated with an emergency response system may be employed.

FIG. 14 illustrates an alternative scenario 1400 in which the systems and methods associated with an emergency dispatch protocol may be employed. In the given scenario, first and second vehicles 1402, 1404 with corresponding human drivers 1406, 1408 are involved in a traffic accident. Each vehicle 1402, 1404 may include corresponding automobile sensors 1410, 1412 which operate as external devices 1128 and are in communication with the computing device 1106 via the network 1132. The automobile sensors 1410, 1412 monitor and record an abrupt vehicle stop indicative of a collision. The automobile sensors 1410, 1412 may further indicate airbag deployment and location. The combination of an abrupt stop and airbag deployment of two vehicles in close proximity is highly indicative of an emergency.

A traffic camera, surveillance camera, or other type of camera 1414 may also operate as an external device 1128 and provide video and audio data of the accident. Furthermore, driver smartphones (not shown) may also operate as external devices 1128 and provide sensor data indicative of abrupt stops. The sensor data from the automobile sensors 1410, 1412, camera 1414, and smartphones all feed into the computing device 1106. The sensor data engine 1122 receives the data values from different types of external devices 1128. The sensor data engine 1122 weighs the sensor data and determines the likelihood of an accident and the determinant code calculator 1124 determines a determinant code. Thus, the determinant code may be determined, in part, by external devices 1128 other than the automobile sensors 1410, 1412. Indeed, the determinant code may be determined, in part, by an external device 1128, such as the camera 1414, which is external to both automobiles. The camera 1414 is a stationary sensor which provides independent verification of the accident and is an independent factor in calculating the determinant code.

In a traffic accident, driver/passenger injuries may be unknown and difficult to determine based on the aforementioned external devices 1128. Nevertheless, the determinant code calculator 1124 may determine a determinant code and corresponding priority based on a statistical analysis of previous vehicle accidents.

Figure 15:
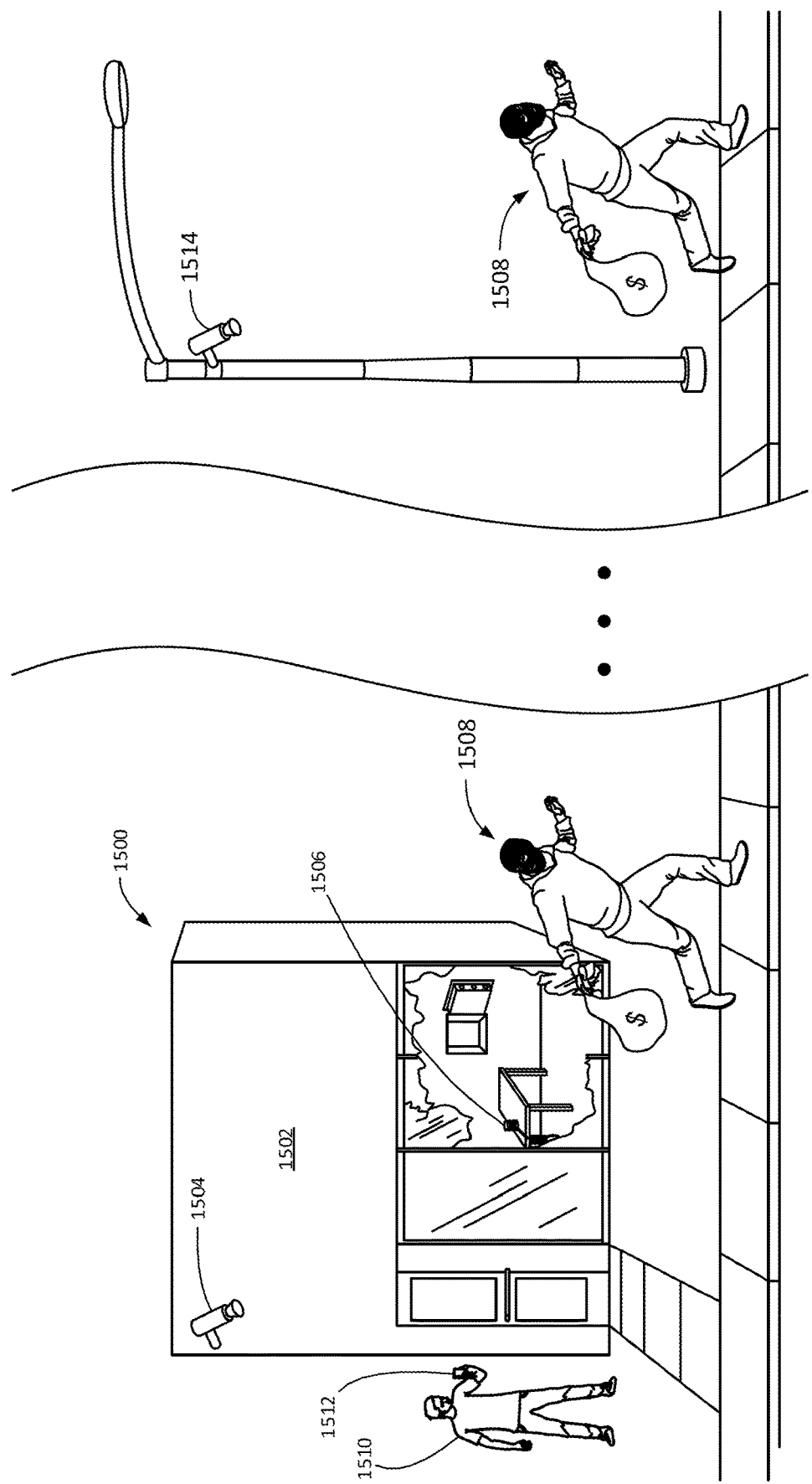
FIG. 15 illustrates a scenario in which the systems and methods associated with an emergency response system may be employed.

FIG. 15 illustrates an alternative scenario 1500 in which the systems and methods associated with an emergency dispatch protocol may be employed. In the given scenario, a break-in occurs in a residence or store front 1502. An exterior surveillance camera 1504 may operate as an external device 1128 and send video and audio data indicative of an emergency. An interior device 1506, inside the residence or store front 1502, may also send video and/or audio data to corroborate the emergency. As previously disclosed, the computing device 1106 makes a determination of an emergency based on the received sensor data. If an emergency is determined, the emergency response is sent to the location of the devices, such as the camera 1504 or interior device 1506.

The surveillance camera 1504 and the interior device 1506 may provide sensor data indicative of a physiological data of a suspect 1508. The physiological data may include facial recognition, body weight, body height, and voice signature. The physiological data may be sent to the computing device 1106 and, if an emergency response is dispatched, to the emergency responders so that the responders have a description of the suspect. The suspect description may be formatted and sent by the personnel instructions engine 1126.

A user 1510 may be in proximity to the residence or store front 1502 and have a smartphone 1512 on the user's person. The smartphone 1512 may also operate as an external device 1128 to record video and/or audio data indicative of break-in. For example, the smartphone 1512 may record audio indicative of broken glass. The smartphone 1512 may include a dispatch application to automatically, without human intervention, capture the audio. The dispatch application may also capture data based on human intervention of a camera. The combined data of the smartphone 1512, surveillance camera 1504, and interior device 1506 is sent to the computing device 1106 to calculate the likelihood of an emergency. The computing device 1106 calculates whether there is an emergency which merits a response without human intervention. Thus, a human emergency response is dispatched based on sensor data and the computing device 1106 to expedite the process.

A second surveillance camera 1514 may capture the suspect 1508 at a second location, remote or distant from the residence or store front 1502. The second surveillance camera 1514 may capture video and/or audio data indicative of a suspect's physiological traits. The physiological traits may include facial recognition, body weight, body height, and voice signature. The emergency dispatch protocol 1114 may conduct a comparison of physiological data received from the first surveillance camera 1504 and the second surveillance camera 1514. Based on the comparison, the computing device 1006 may direct the emergency response to the second location to apprehend the suspect 1508.

Alternatively, or in addition, the user 1510 may operate the smartphone 1512 and call into the dispatch center 202 described in FIG. 2. The user 1510 may communicate with the dispatcher 204, through voice or text, and proceed through an interrogation protocol. The sensor data received from the external devices 1504, 1506, 1514 may serve to corroborate the emergency and assist in generating a determinant code. The dispatch centers 202, 1002 may operate independently or as combined systems and may receive user voice/text calls, user voice/text calls and sensor data, or sensor data only in calculating a determinant code and generating an emergency response.

Figure 16:
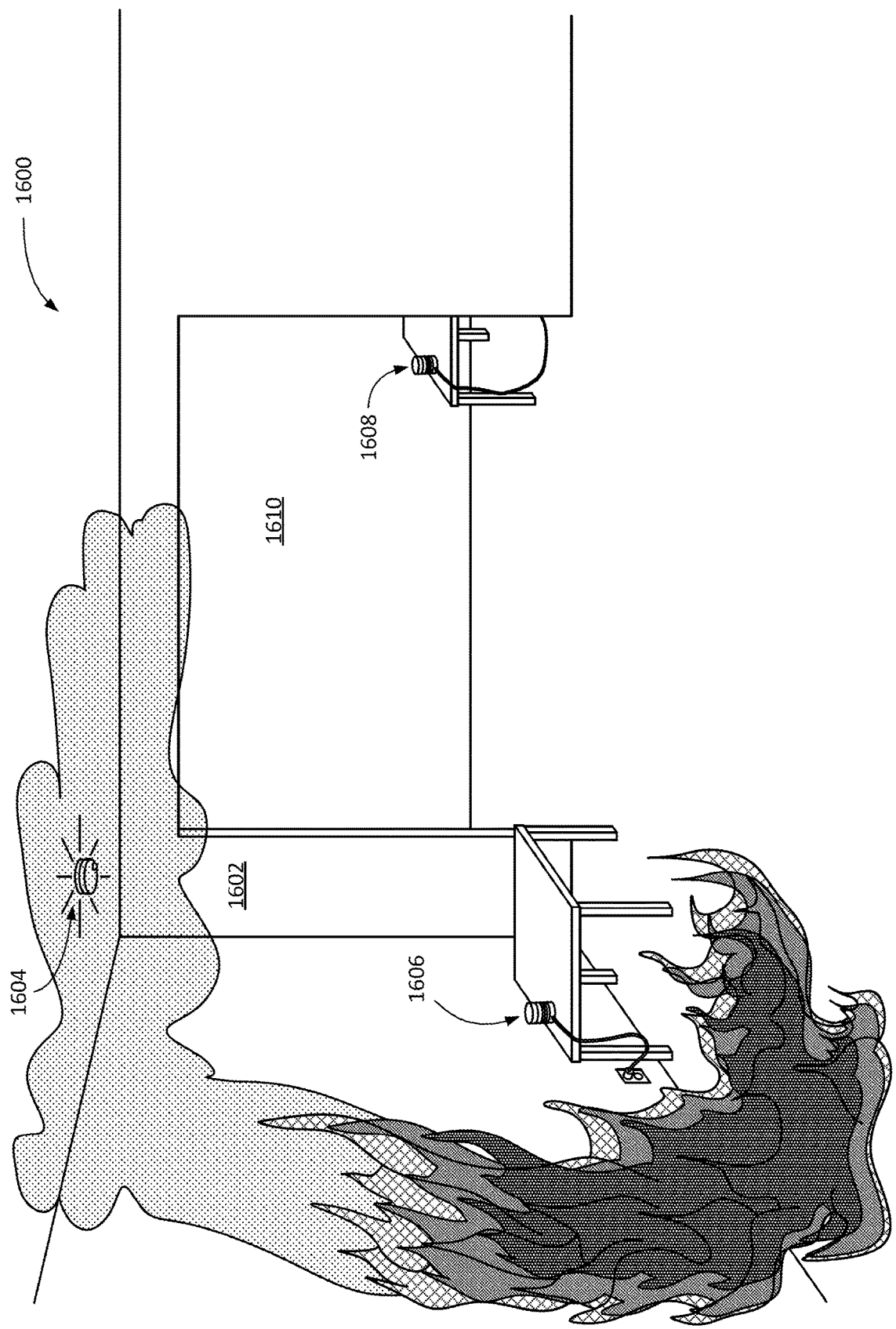
FIG. 16 illustrates a scenario in which the systems and methods associated with an emergency response system may be employed.

FIG. 16 illustrates an alternative scenario 1600 in which the systems and methods associated with an emergency dispatch protocol may be employed. In the given scenario, a fire breaks out in a first room 1602 in a residence. A smoke alarm 1604 initiates an audio alert and may also operate as an external device 1028 to provide sensor data to the computing device 1006. The smoke alarm 1604 sensor data may include data indicative of smoke and temperature. An interior device 1606 may also provide sensor data indicative of video, audio, and/or temperature. The sensor data from the interior device 1606 corroborates the smoke alarm 1604 and reduces the likelihood of a false alarm.

As the fire progresses, the interior device 1606 may record a rise in temperature and a second interior device 1608 in a second room 1610 may also provide sensor data indicative of video, audio, and/or temperature. In the given example, the fire may ultimately render the first interior device 1606 inoperable and the sudden communication break provides an additional factor to the computing device 1106 that a fire is present. Thus, the combined sensor data from the smoke alarm 1604, interior device 1606, and second interior device 1608 confirm the presence of a raging fire. The sensor data may further include a location of the perceived fire as the smoke alarm 1604, interior device 1606, and second interior device 1608 may include GPS or have registered a physical location. Once again, the determinant code calculator 1024 generates a determinant code without active human intervention and without an interrogation. The determinant code is sent to the CAD system to initiate an emergency dispatch.

Figure 17A:
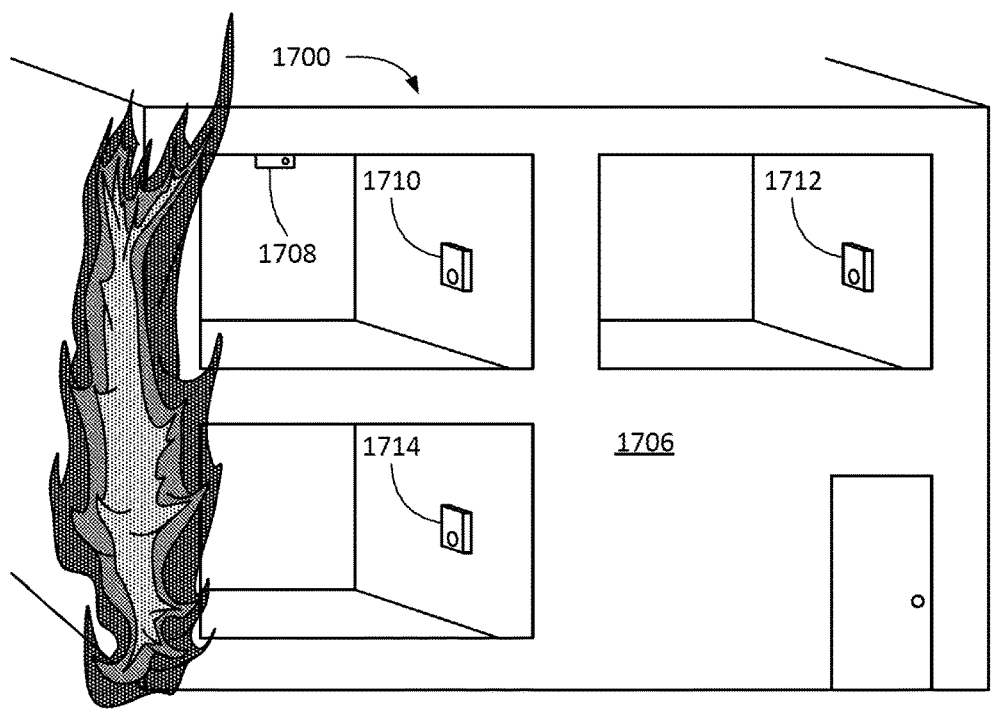
FIGS. 17A-17C illustrate scenarios in which the systems and methods associated with an emergency response system may be employed.
Figure 17B:
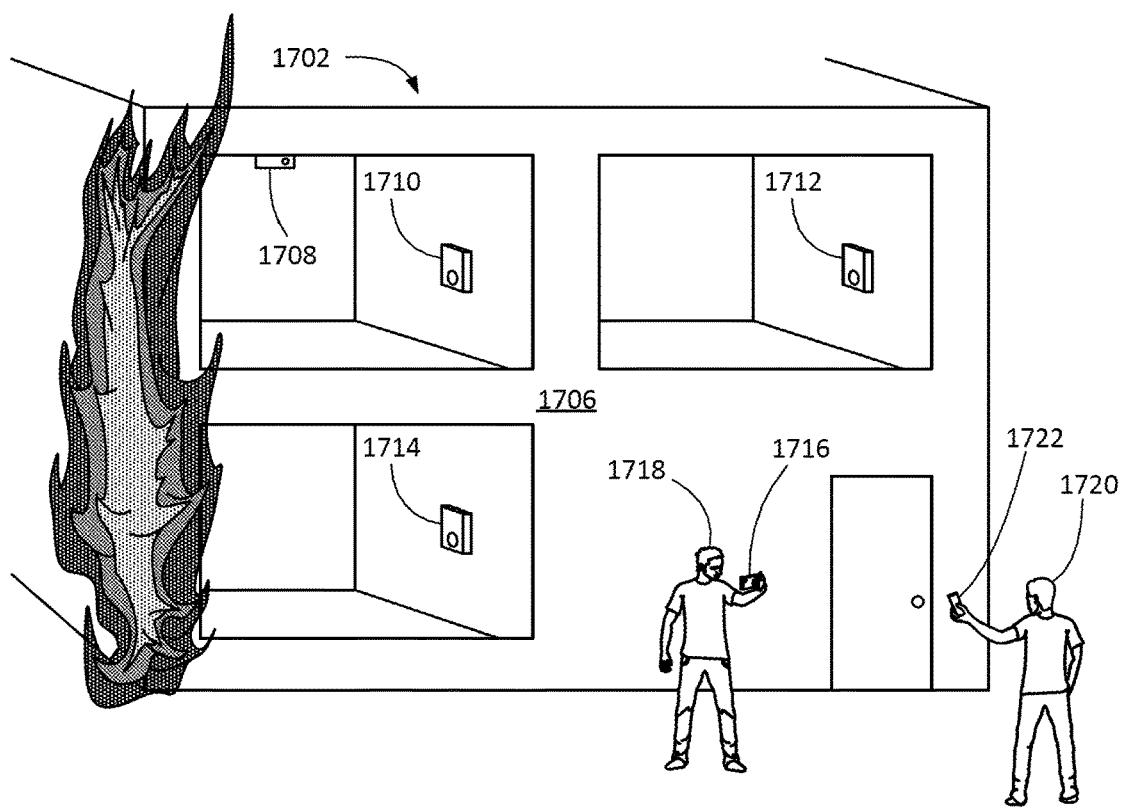
Figure 17C:
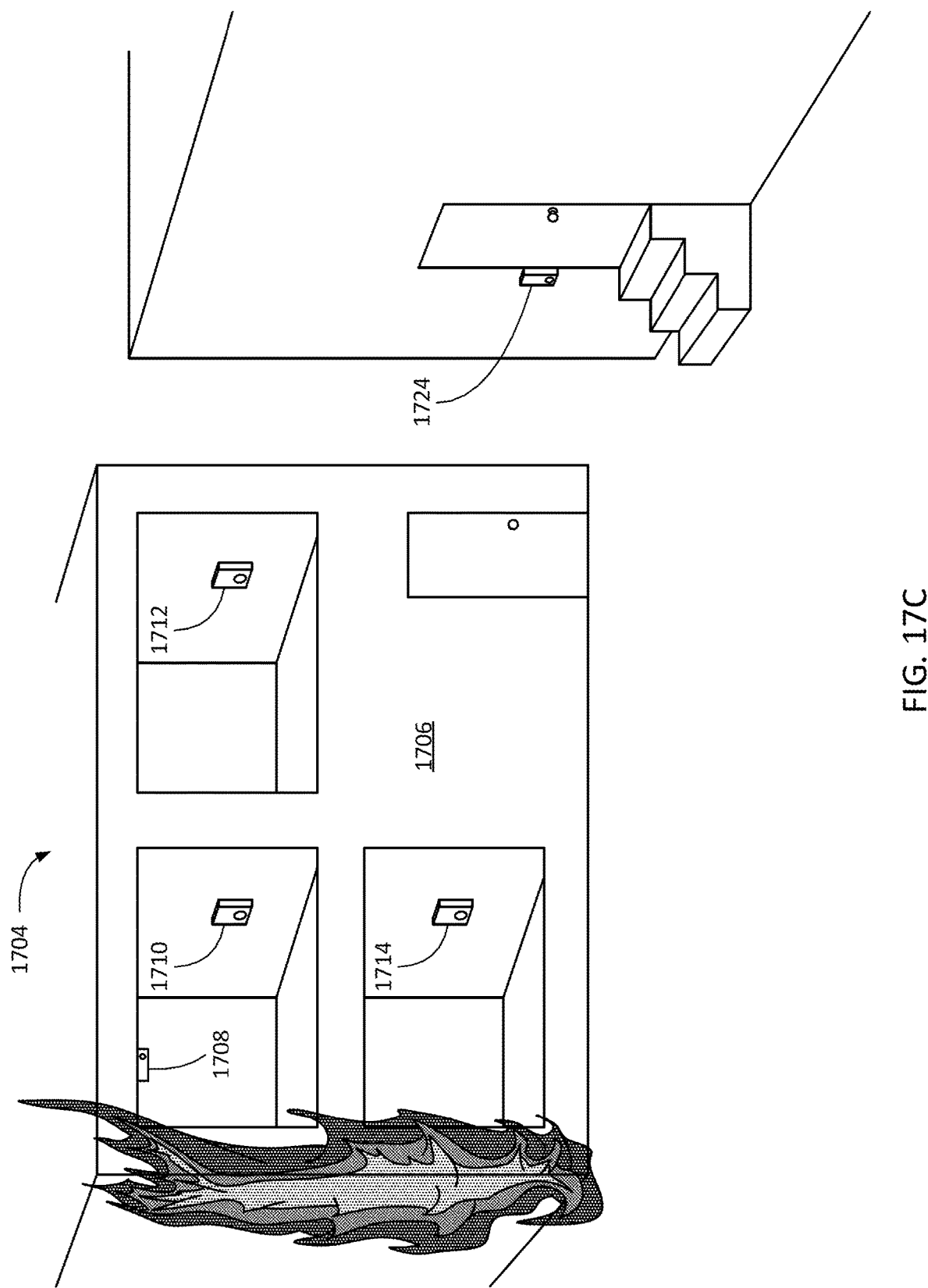

FIGS. 17A-17C illustrate similar scenarios 1700, 1702, 1704 in which the systems and methods associated with an emergency dispatch protocol may be employed. In the given scenarios, a fire has occurred in a building 1706 and different external devices 1128 generate sensor data to identify the emergency.

In FIG. 17A, a fire alarm 1708 and three thermostats 1710, 1712, 1714 function as external devices 1128 and are in electrical communication with the network 1132. The thermostats 1710, 1712, 1714 are Wi-Fi enabled and may be embodied as Nest thermostats. The fire alarm 1708 generates sensor data indicating smoke and heat and the thermostats 1710, 1712, 1714 generate sensor data indicating heat. The disparate sensor data is processed by the computing device 1106 and the determinant code calculator 1124 determines a likelihood of a fire emergency and generates a determinant code indicating the emergency and a priority.

In FIG. 17B, the fire alarm 1708 and three thermostats 1710, 1712, 1714 generate the same sensor data. Furthermore, a smartphone 1716 captures a "selfie" photograph of a user 1718 in front of the building 1706 with smoke pouring out. The photograph is either sent to the computing device 1106 by the user 1718 or posted by the user 1718 to a social media website. The social media website may identify the posted picture, indicate a location, and send the location and picture to the computing device 1106. Alternatively, a data aggregator may identify the posted picture on the social media website and confirm the location.

Alternatively, or in addition, a second user 1720 may take more direct action to reach out to emergency responders. The second user 1720 may operate a smartphone 1722 and call into the dispatch center 202 described in FIG. 2. The second user 1720 may communicate with the dispatcher 204, through voice or text, and proceed through an interrogation protocol. The sensor data received from the external devices 1708-1716, 1722 may serve to corroborate the emergency and assist in generating a determinant code. Thus, a dispatch center 202, 1102 may receive a user communication, a user communication and sensor data, or sensor data only in calculating a determinant code and generating an emergency response.

In FIG. 17C, the fire alarm 1708, and three thermostats 1710, 1712, 1714 generate the same sensor data. Also present is a nearby doorbell sensor 1724, such as a Ring device/doorbell. The doorbell sensor 1724 provides live video feed including any flames and smoke from the building 1706. The live video feed may be processed and the flames and smoke identified as a possible fire emergency. Data confirming a possible fire emergency may be sent to the computing device 1106 which weighs the likelihood of a fire emergency with the sensor data received from the fire alarm 1708 and thermostats 1710, 1712, 1714.

Figure 18:
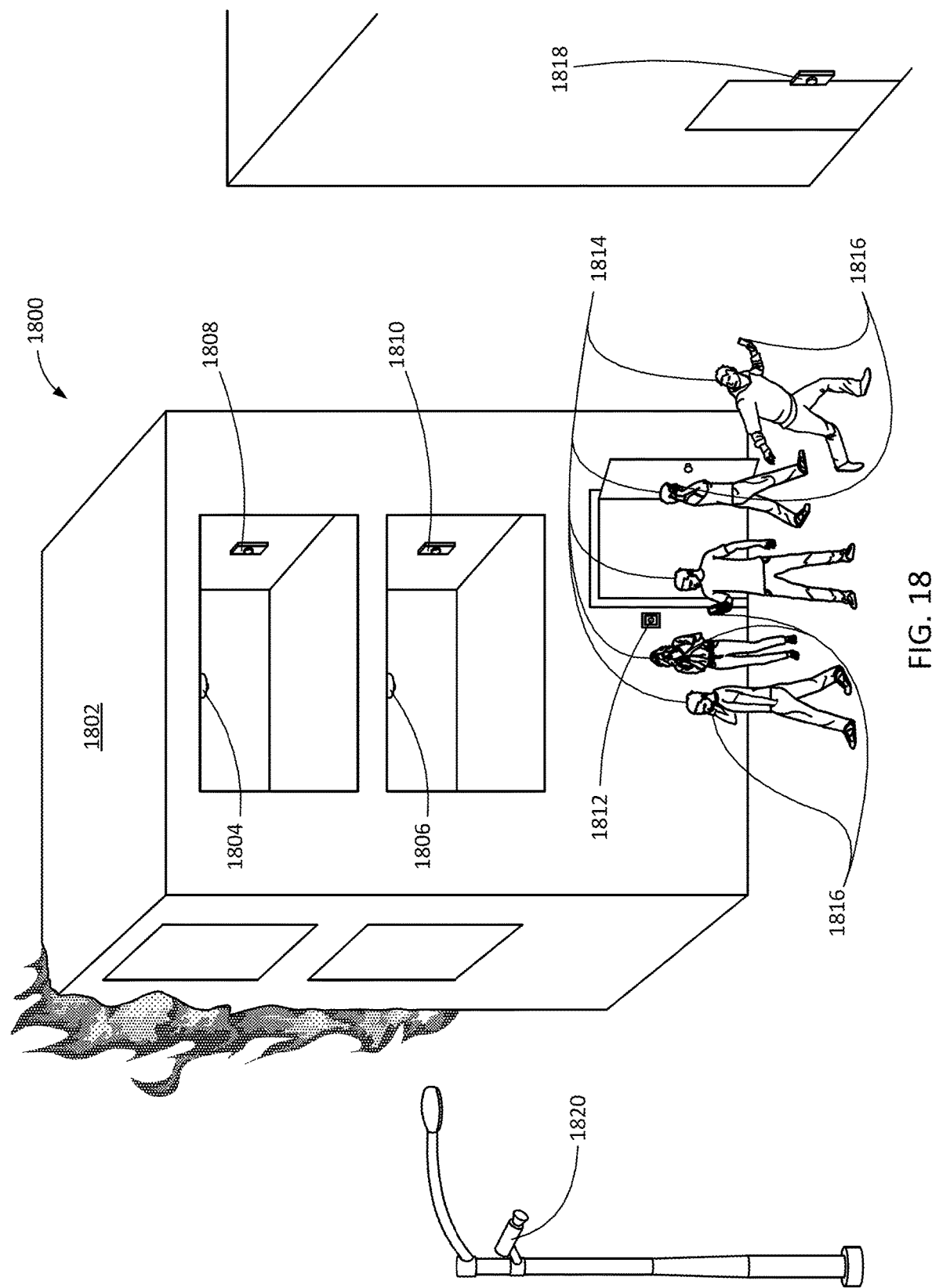
FIG. 18 illustrates a scenario in which the systems and methods associated with an emergency response system may be employed.

FIG. 18 illustrates an alternative scenario 1800 in which the systems and methods associated with an emergency dispatch protocol may be employed. In the given scenario, a fire has occurred in a building 1802 and one or more smoke detectors 1804, 1806 operate as external devices 1128 and generate sensor data to indicate the presence of smoke. One or more thermostats 1808, 1810 operate as external devices 1128 and generate sensor data to indicate elevated temperatures. In one embodiment, the thermostats 1808, 1810 may be Nest thermostats.

A surveillance camera 1812, such as a Ring device, may be attached to the building 1802 and receive activity indicative of a fire emergency. For example, the surveillance camera 1812 may view the flames and/or people 1814 escaping the building. The surveillance camera 1812 generates sensor data indicative of a fire emergency.

Further, smartphones 1816 carried by the fleeing people 1814 indicate rapid movement away from the fire emergency. The smartphones 1816, individually and in combination, generate sensor data to corroborate an emergency in the building being vacated.

Finally, one or more surveillance cameras 1818, 1820, external and unattached to the building 1802, may view the fire and the people 1814 and generate sensor data. A surveillance camera 1818 may be located on a nearby building and may also be a Ring device or any other type of camera. A surveillance camera 1820 may also be a dedicated camera mounted on a nearby fixture.

All of the external devices 1804-1812 and 1816-1820 are in communication with the network 1132 and the computing device 1106 to transmit sensor data to the sensor data engine 1122. The disparate sensor data is processed by the computing device 1106, sensor data engine 1122, and the determinant code calculator 1124 to determine a likelihood of a fire emergency and to generate a determinant code indicating the emergency and a priority.

Referring again to FIG. 2, the dispatch center 202 may operate to receive user voice/text calls as a conventional emergency dispatch system. The dispatch center 202 may also operate to receive user voice/text calls and sensor data from external devices as described in FIGS. 2-10 and the accompanying text. The dispatch center 202 may further operate to receive sensor data only in calculating a determinant value and generating an emergency response as described in FIGS. 11-18 and the accompanying text. Thus, the dispatcher 204 may or may not be involved in an interrogation dialog with a caller. The dispatch center 202 may be configured to proceed with emergency dispatch with an incoming caller communication and no sensor data, with an incoming caller communication and sensor data, or with sensor data alone.

Previous dispatch systems have relied entirely on voice communication between a caller and a dispatcher. As disclosed herein, a dispatch computer system and an emergency response protocol may generate an emergency response based on sensor data and without human interrogation and without human initiation. Thus, a response may be dispatched without a human actively texting, calling, or corresponding with the dispatch computer system. The sensor data may be provided by IOT devices carried by a caller, patient, or victim. The sensor data may be provided by devices in proximity to the emergency and/or carried by third-party users.

Alternatively, a dispatch computer system and an emergency response protocol may generate an emergency response based on human interrogation which is augmented with sensor data. The sensor data may be generated by one or more of any of the IOT devices disclosed herein. All of the disparate data, including voice data in some embodiments, arrives at the dispatch center to accurately generate an appropriate determinant code.

As disclosed herein, a determinant code, including an emergency type and a priority level, is determined by a determinant code calculator based on answers to pre-programmed inquiries, external sensor data, and/or a combination of both. The emergency type and priority level may be chosen from one of a number of pre-selected options. A chief complaint or emergency may be determined based on pre-programmed inquiries, external sensor data, and/or a combination of both. The likelihood of the chief complaint or emergency may be confirmed based on an analysis of the external sensor data.

The system and method disclosed herein automatically generates a determinant code based, in part or completely, on external sensor data. External sensor data indicates detection of an emergency type and location. Determinant code generation based on external sensor data enables faster and more accurate emergency dispatch than with conventional systems.

The system disclosed herein includes external devices with sensors, a dispatch computer, a CAD with a vehicle tracking system, and a plurality of emergency dispatch vehicles with vehicle computers in communication with the CAD. The dispatch computer may include a memory, processor coupled to the memory, display, keyboard, network communicator, touch screen, and the like. The processor is programmed with executable instructions including a sensor data engine to obtain, monitor, analyze, and display the external sensor data. The executable instructions further include a determinant code calculator to generate a determinant code based on the external sensor data. As disclosed herein, the external devices may take the form of microphones, cameras, accelerometers, temperature sensors, climate sensors, smoke sensors, movement sensors, GPS, and the like or other suitable devices to permit emergency monitoring. The external devices include a communication/network interface to enable communication with the dispatch center over a network.

As external sensor data is collected, it may be stored in an external device database so that a record of external device data capture is preserved. The external device database may include pattern recognition logic to identify a possible emergency based on metrics. For example, external sensor data indicating abrupt vehicle stop in a location may, over time, indicate a likely accident. Further, external sensor data indicating a certain temperature in a specific building, such as an industrial factory, may indicate a likely fire. Thus, the external device database may contain logic about numerous possible patterns that are either indicate normal situations or an emergency based on motion, temperature, audio, video, climate, and the like.

The system includes control devices in the form of a dispatch computer, CAD, vehicle tracking system, and vehicle computers that are all in communication with each other to automatically control the dispatch of an emergency dispatch vehicle. The system and method enables automatic monitoring, comparing, and analyzing of collected external sensor data in order to verify whether an emergency is occurring or has occurred as compared to past normal conditions. The dispatch computer may display the analysis results to enable a dispatcher to effectively monitor the prospective emergency or situation.

In operation, the system sends signals to control emergency response vehicle movement based on a detected emergency. The detected emergency is confirmed with generation of a determinant code indicative of an emergency type and priority. If an analysis results indicate a type of emergency in a specific location, then the system can send a signal to an emergency response vehicle to proceed to the specific location with lights-and-siren or regular traffic.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure. Terms, components, and methodologies described herein in reference to one figure and system may also be incorporated with another figure or system. Thus, definitions and descriptions herein are applicable to all embodiments, figures, and systems and are not limited to one embodiment.

What is claimed is:

1. A computing device to assist a dispatcher in responding to an emergency being reported by an information provider, comprising:
    a processor;
    an input device in electrical communication with the processor;
    an output device in electrical communication with the processor;
    a network interface in electrical communication with the processor and a network; and
    a memory in electrical communication with the processor, the memory having stored thereon:
    an interrogation protocol to receive answers from the information provider to pre-programmed inquiries of the interrogation protocol for the dispatcher to ask the information provider, the pre-programmed inquiries of the interrogation protocol to be displayed to the dispatcher on the output device and communicated from the dispatcher to the information provider;
    a sensor data engine configured to receive different types of external sensor data provided at the network interface from a plurality of external devices via the network, the external sensor data comprising at least dynamic physiological data specific to the information provider, dynamic physiological data specific to a person in proximity to the information provider, or a combination thereof;
    a determinant code calculator configured to:
    receive the external sensor data from the sensor data engine, and
    generate, based on the received answers to the pre-programmed inquiries and the external sensor data, a determinant code from one of a plurality of pre-established determinant codes, the determinant code indicating a priority of an emergency response, wherein the computer device provides the determinant code to an emergency responder system to generate an emergency dispatch response; and
    the sensor data engine further configured to determine an accuracy of the determinate code based at least on the external sensor data including the dynamic physiological data, wherein the determination is further based on the external sensor data being weighted such that evidence of a past event will weight in favor of an emergency incident, and wherein the accuracy is indicative of a level of likelihood of the determinate code.

2. The computer device of claim 1, wherein the external sensor data includes the dynamic physiological data specific to the information provider or the person in proximity to the information provider.

3. The computer device of claim 2, wherein the dynamic physiological data includes heart rate data.

4. The computer device of claim 2, wherein the dynamic physiological data includes body temperature data.

5. The computer device of claim 2, wherein the dynamic physiological data includes respiration data.

6. The computer device of claim 1, wherein the external sensor data includes video data.

7. The computer device of claim 1, wherein the external sensor data includes still image data.

8. The computer device of claim 1, wherein the external sensor data includes accelerometer data.

9. The computer device of claim 1, wherein the external sensor data includes global positioning system (GPS) data.

10. The computer device of claim 1, wherein the external sensor data includes ambient temperature data.

11. The computer device of claim 1, wherein the external sensor data includes audio data.

12. The computer device of claim 1, wherein the interrogation protocol is configured to receive dispatcher-entered answers to the pre-programmed inquiries, wherein the sensor data and dispatcher-entered answers are received simultaneously.

13. The computer device of claim 1, wherein the sensor data engine is further configured to display one or more data values associated with the external sensor data to the dispatcher.

14. The computer device of claim 1, wherein the pre-programmed inquiries of the interrogation protocol are to be communicated from the dispatcher to the information provider via text message.

15. The computer device of claim 1, wherein information provider answers to the pre-programmed inquiries are received via text message.

16. The computer device of claim 1, wherein the computer device is configured to generate instructions based on the external sensor data, the instructions to be provided to personnel of the emergency dispatch response.

17. The computer device of claim 1, wherein the interrogation protocol is configured to generate a chief complaint responsive to received answers from the information provider.

18. The computer device of claim 17, wherein the sensor data engine is configured to determine a likelihood of the chief complaint based on the received external sensor data.

19. The computer device of claim 1, wherein the interrogation protocol is configured to receive a chief complaint input from the dispatcher and display a chief complaint.

20. The computer device of claim 19, wherein the sensor data engine is configured to determine a likelihood of the chief complaint based on the received external sensor data.

21. The computer device of claim 1, wherein the interrogation protocol is configured to determine the emergency based on the received answers and the sensor data engine is configured to determine the likelihood that the emergency is accurate based on the external sensor data.

22. A method to assist a dispatcher in responding to an emergency being reported by an information provider, comprising:
providing pre-programmed inquiries of an interrogation protocol for the dispatcher to ask the information provider;
receiving, from the information provider, answers to the pre-programmed inquiries;
a computer device of a dispatch center receiving the answers;
the computer device receiving different types of external sensor data from external devices through a network interface of the computer device, the external sensor data comprising at least dynamic physiological data specific to the information provider, dynamic physiological data specific to a person in proximity to the information provider, or a combination thereof;
the computer device generating a determinant code from one of a plurality of pre-established determinant codes based on the received answers to the pre-programmed inquiries and the external sensor data, the determinant code indicating a priority of an emergency response;
the computer device determining an accuracy of the determinate code based at least on the external sensor data including the dynamic physiological data, wherein the determining is further based on the external sensor data being weighted such that evidence of a past event will weight in favor of an emergency incident, and wherein the accuracy is indicative of a level of likelihood of the determinant code; and
the computer device providing the determinant code to an emergency responder system to generate an emergency dispatch response.

23. The method of claim 22, further comprising sending a request to one of the external devices to provide external sensor data to the computer device.

24. The method of claim 23, wherein the request is sent to the external device based on a location of the external device.

25. The method of claim 23, wherein the request is sent to the external device based on a type of external sensor data to be provided by the external device.

26. The method of claim 25, wherein the type of external sensor data is determined based on the answers to the pre-programmed inquiries received from the information provider.

27. The method of claim 23, wherein the emergency is a medical emergency of a victim, and wherein the request is sent to the external device based on an association between the external device and the victim.

28. The method of claim 23, wherein the request is sent to the external device based on an association between the information provider and the external device.

29. The method of claim 22, wherein the answers to the pre-programmed inquiries are received verbally from the information provider.

30. The method of claim 22, wherein the answers to the pre-programmed inquiries are received by text from the information provider.

31. The method of claim 22, further comprising the computer device generating a chief complaint based on answers received from the information provider.

32. The method of claim 31, further comprising the computer device determining a likelihood of the chief complaint based on the external sensor data.

33. The method of claim 32, further comprising the computer device receiving the chief complaint from the dispatcher.

34. The method of claim 33, further comprising the computer device determining the likelihood of the chief complaint based on the external sensor data.

35. The method of claim 22, further comprising:
generating instructions based on the external sensor data; and
sending the instructions to personnel of the emergency dispatch response.

36. The method of claim 22, further comprising:
determining the emergency based on the received answers to the pre-programmed inquiries; and
determining the likelihood that the emergency is accurate based on the external sensor data.

37. A non-transitory computer-readable storage medium, the computer-readable storage medium including instructions that when executed by a computer device, cause the computer device to:
present pre-programmed inquiries of an interrogation protocol for an emergency;
receive answers to the pre-programmed inquiries of the interrogation protocol;
receive different types of external sensor data from external devices over a network, the external sensor data comprising at least dynamic physiological data specific to the information provider, dynamic physiological data specific to a person in proximity to the information provider, or a combination thereof;
generate a determinant code, based on the received answers from the pre-programmed inquiries and the external sensor data, the determinant code indicating a priority of an emergency response;

determine an accuracy of the determinate code based at least on the external sensor data including the dynamic physiological data, wherein the determination is further based on the external sensor data being weighted such that evidence of a past event will weight in favor of an emergency incident, and wherein the accuracy is indicative of a level of likelihood of the determinate code; and provide the determinant code to an emergency responder system to generate an emergency dispatch response.

38. The non-transitory computer-readable storage medium of claim 37, wherein the instructions further cause the computer device to send a request to one of the external devices to provide a type of external sensor data to the computer device.

39. The non-transitory computer-readable storage medium of claim 38, wherein the type of requested external sensor data is determined based on the received answers to the pre-programmed inquiries.

40. The non-transitory computer-readable storage medium of claim 38, wherein the emergency is a medical emergency of a victim, and wherein the request is sent to the external device based on an association between the external device and a victim.

41. The non-transitory computer-readable storage medium of claim 37, wherein the instructions further cause the computer device to generate a chief complaint based on the received answers to the pre-programmed inquiries.

42. The non-transitory computer-readable storage medium of claim 41, wherein the instructions further cause the computer device to determine the likelihood of the chief complaint based on the external sensor data.

43. The non-transitory computer-readable storage medium of claim 37, wherein the instructions further cause the computer device to receive a chief complaint as an input.

44. The non-transitory computer-readable storage medium of claim 43, wherein the instructions further cause the computer device to determine a likelihood of the chief complaint based on the external sensor data.

45. The non-transitory computer-readable storage medium of claim 37, wherein the instructions further cause the computer device to:

generate instructions based on the external sensor data; and send the instructions to personnel of the emergency dispatch response.

46. The non-transitory computer-readable storage medium of claim method of claim 37, wherein the instructions further cause the computer device to:

determine the emergency based on the received answers; and determine a likelihood that the emergency is accurate based on the external sensor data.

* * * * *